(12) United States Patent
Arnold

(10) Patent No.: US 10,745,749 B2
(45) Date of Patent: Aug. 18, 2020

(54) METHODS FOR DETECTING NUCLEIC ACID SEQUENCE VARIANTS

(71) Applicants: Biocept, Inc., San Diego, CA (US); Aegea Biotechnologies, Poway, CA (US)

(72) Inventor: Lyle Arnold, Poway, CA (US)

(73) Assignees: Biocept, Inc., San Diego, CA (US); Aegea Biotechnologies, Poway, CA (US)

( * ) Notice: Subject to any disclaimer, the term of this patent is extended or adjusted under 35 U.S.C. 154(b) by 0 days.

(21) Appl. No.: 15/796,982

(22) Filed: Oct. 30, 2017

(65) Prior Publication Data

US 2018/0112263 A1 Apr. 26, 2018

Related U.S. Application Data

(63) Continuation of application No. 13/841,842, filed on Mar. 15, 2013, now Pat. No. 9,834,817, which is a continuation-in-part of application No. PCT/US2012/036678, filed on May 4, 2012.

(60) Provisional application No. 61/482,576, filed on May 4, 2011.

(51) Int. Cl.
*C12Q 1/6869* (2018.01)
*C12Q 1/6858* (2018.01)

(52) U.S. Cl.
CPC ......... *C12Q 1/6869* (2013.01); *C12Q 1/6858* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 5,958,700 A | 9/1999 | Nadeau et al. | |
| 6,004,513 A * | 12/1999 | Albagli | B01L 7/52 422/68.1 |
| 6,180,338 B1 | 1/2001 | Adams | |
| 6,379,888 B1 | 4/2002 | Nadeau et al. | |

(Continued)

FOREIGN PATENT DOCUMENTS

| | | |
|---|---|---|
| JP | H11-056380 | 3/1999 |
| JP | 2001-161377 | 6/2001 |

(Continued)

OTHER PUBLICATIONS

Machine translation of JP-2006166808. Generated on Jan. 5, 2019. (Year: 2006).*

(Continued)

*Primary Examiner* — Angela M. Bertagna
(74) *Attorney, Agent, or Firm* — Cooley LLP

(57) ABSTRACT

The present invention provides methods for detecting the presence or absence of a nucleic acid variant in a target region. These methods include amplifying the target region with a forward primer and a reverse primer in the presence of a selector blocker. The selector blocker includes a sequence complementary to the target region in the absence of the nucleic acid variant. The methods further include detecting amplification of the target region where amplification of the target region indicates the presence of the nucleic acid variant in the target region. The nucleic acid variant can include deletions, mutations or insertions.

16 Claims, 51 Drawing Sheets

Specification includes a Sequence Listing.

(56) References Cited

U.S. PATENT DOCUMENTS

| | | | |
|---|---|---|---|
| 6,399,304 B1* | 6/2002 | Kilger | C12O 1/6869 |
| | | | 435/6.12 |
| 8,679,789 B2 | 3/2014 | Arnold, Jr. et al. | |
| 9,243,286 B2 | 1/2016 | Arnold, Jr. et al. | |
| 9,834,817 B2 | 12/2017 | Arnold | |
| 2001/0034048 A1 | 10/2001 | Kurn | |
| 2003/0059786 A1* | 3/2003 | Ward | C12O 1/6816 |
| | | | 435/6.12 |
| 2003/0165888 A1* | 9/2003 | Brown | C07H 21/00 |
| | | | 435/5 |
| 2005/0164184 A1 | 7/2005 | Chun | |
| 2008/0305478 A1 | 12/2008 | Chun | |
| 2009/0047669 A1 | 2/2009 | Zhang et al. | |
| 2010/0009355 A1 | 1/2010 | Kolodney | |
| 2010/0221717 A1 | 9/2010 | Chen et al. | |
| 2010/0227320 A1 | 9/2010 | Fu | |
| 2010/0285478 A1 | 11/2010 | Chen et al. | |
| 2013/0330774 A1* | 12/2013 | De Both | C12N 15/102 |
| | | | 435/91.1 |
| 2014/0335514 A1 | 11/2014 | Arnold | |

FOREIGN PATENT DOCUMENTS

| | | | |
|---|---|---|---|
| JP | 2004-081051 A | | 3/2004 |
| JP | 2006166808 A | * | 6/2006 |
| JP | 2008-086296 A | | 4/2008 |
| JP | 2010-535480 A | | 11/2010 |
| WO | WO 2004/098386 A2 | | 11/2004 |
| WO | WO 2007/106534 A2 | | 9/2007 |
| WO | WO 2008/104794 A2 | | 9/2008 |
| WO | WO 2008/109823 A2 | | 9/2008 |
| WO | WO 2011/018232 A1 | | 2/2011 |
| WO | WO 2011/028041 A2 | | 3/2011 |
| WO | WO 2011/042104 A1 | | 4/2011 |
| WO | WO 2012/151560 A2 | | 11/2012 |

OTHER PUBLICATIONS

Mueckstein et al. BMC Bioinformatics 2010; 11: 35. (Year: 2010).*
International Search Report and Written Opinion for International Application No. PCT/US2012/036678, dated Jan. 23, 2013, 7 pages.
International Preliminary Report on Patentability for International Application No. PCT/US2012/036678, dated Nov. 5, 2013, 5 pages.
Extended European Search Report in EP Application No. 12779445.1 dated Nov. 14, 2014, 7 pages.
Dominguez, P.L. & Kolodney, M.S. "Wild-type blocking polymerase chain reaction for detection of single nucleotide minority mutations from clinical specimens." Oncogene 2005; 24: 6830-6834.
Han, L. et al., "Peptide nucleic acid- mediated one-step PCR assay in detection of K-ras mutation", Academic Journal of Second Military Medical University, 30(7):762-766 (2009) (English Abstract).
Johnson et al. "Locked nucleic acid (LNA) single nucleotide polymorphism (SNP) genotype analysis and validation using real-time PCR." Nucleic Acids Research (2004) 32(6): e55.
Liu, Q. et al., "Pyrophosphorolysis-activated polymerization (PAP): application to allele-specific amplification," BioTechniques, 29(5):1072-1074, 1076, 1078, 1080, 1082-1083 (2000).
Lo et al. "Digital PCR for the molecular detection of fetal chromosomal aneuploidy." Proceedings of the National Academy of Sciences, USA (2007) 104(32): 13116-13121.
Margraf, R.L. et al., "Masking selected sequence variation by incorporating mismatches into melting analysis probes", Human Mutation, 27(3):269-278 (2006).
Milbury, C.A. et al., "PCR-Based Methods for the Enrichment of Minority Alleles and Mutations", Clinical Chemistry, 55(4):632-640 (2009).
Newton, C. R. et al., "Analysis of any point mutation in DNA. The amplification refractory mutation system (ARMS)," Nucleic Acids Research, 17(7):2503-2516 (1989).
Orum et al. "Single base pair mutation analysis by PNA directed PCR clamping." Nucleic Acids Research 1993; 21(23): 5332-5336.
Orum, H. "PCR Clamping." Current Issues in Molecular Biology 2000; 2: 27-30.
Von Wintzingerode et al. "Peptide Nucleic Acid-Mediated PCR Clamping as a Useful Supplement in the Determination of Microbial Diversity." Applied and Environmental Microbiology 2000; 66(2): 549-557.
Yu et al. "Specific inhibition of PCR by non-extendable oligonucleotides using a 5'to 3'exonuclease-deficient DNA polymerase." Biotechniques 1997; 23: 714-720.
Zhou, L. et al., "Rare allele enrichment and detection by allele-specific PCR, competitive probe blocking. And melting analysis", Biotechniques, 50(5):311-318 (2011).
Extended European Search Report in EP Application No. 18172421.2, dated Jun. 22, 2018, 7 pages.

* cited by examiner

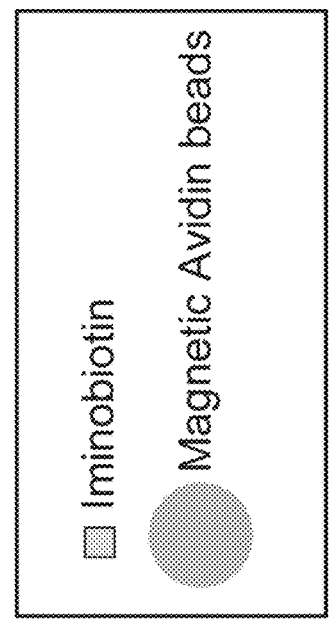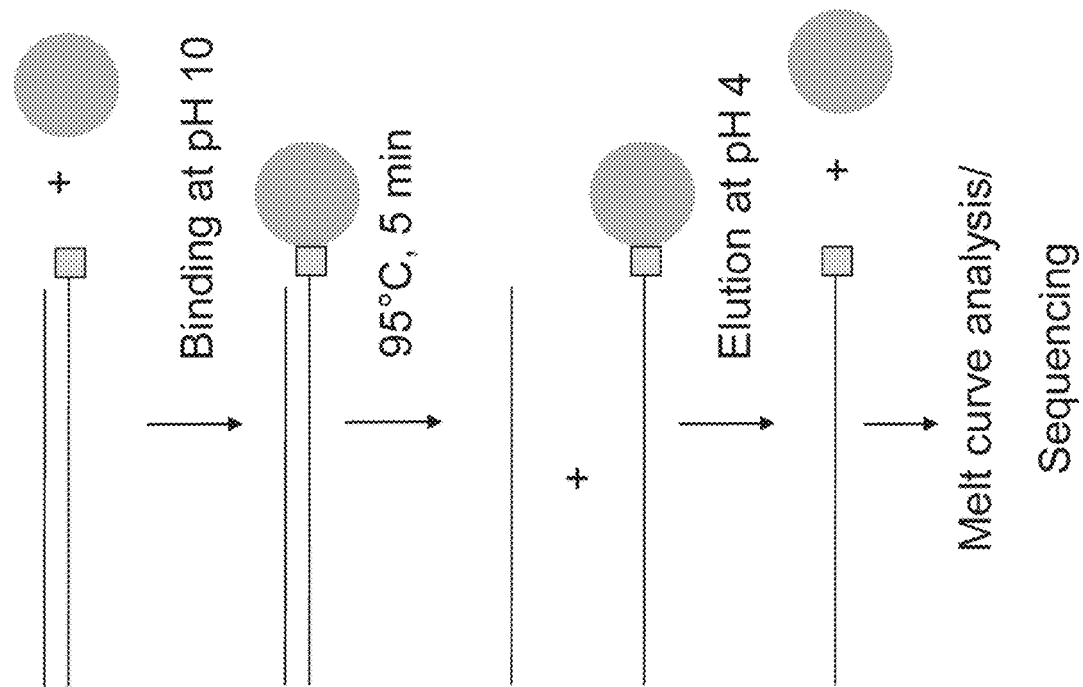
FIG. 8

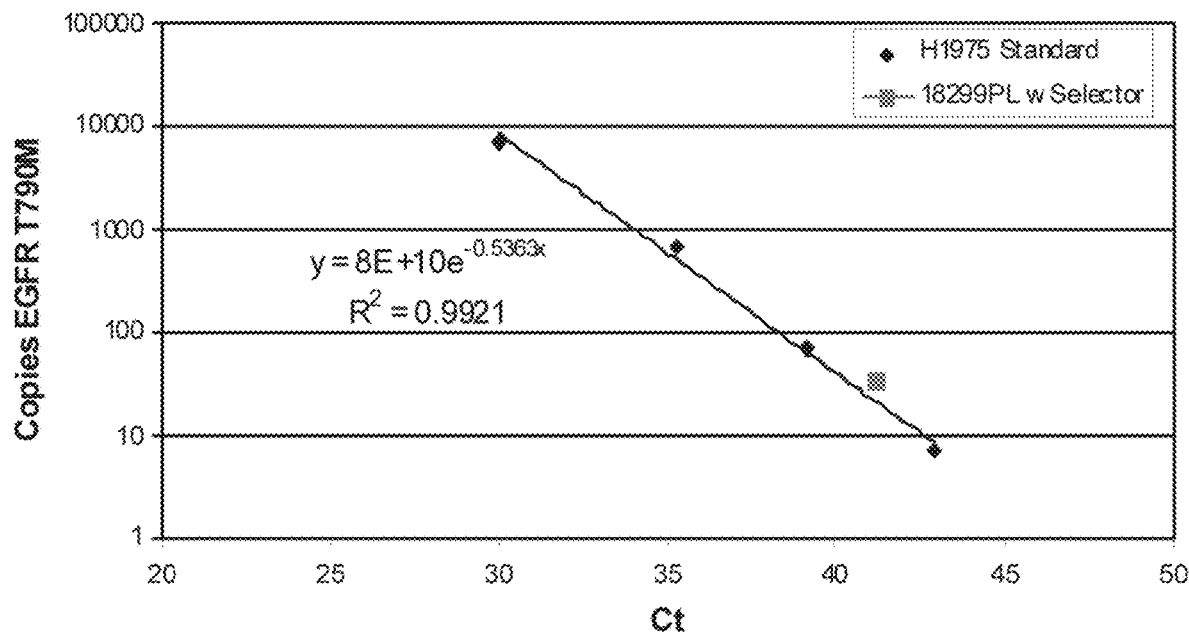
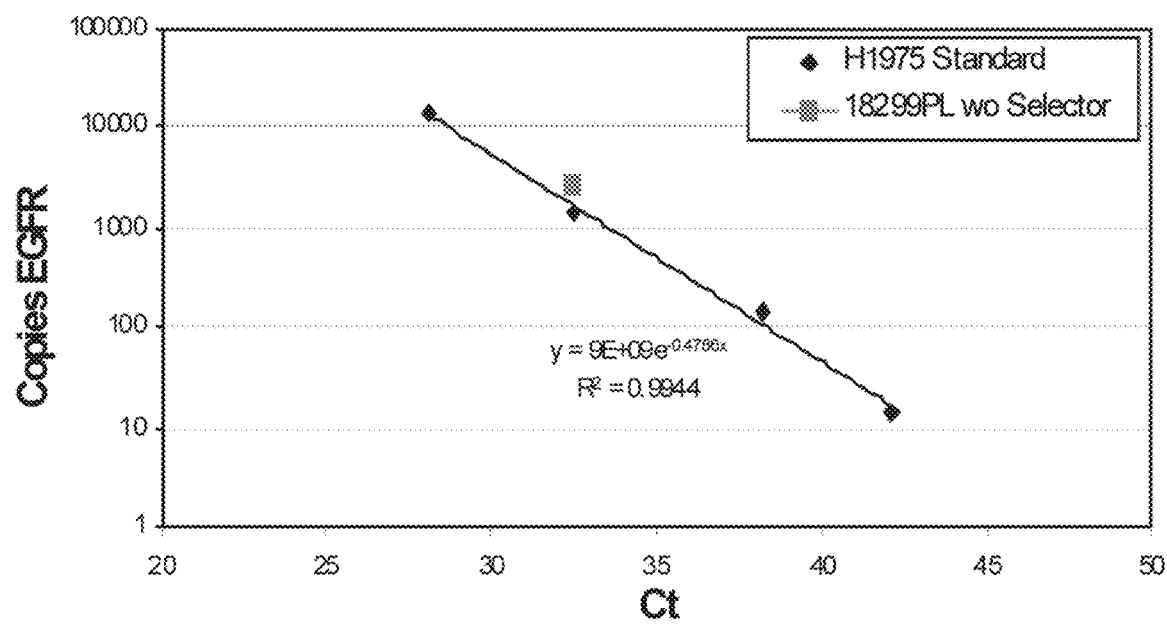
FIG. 11B

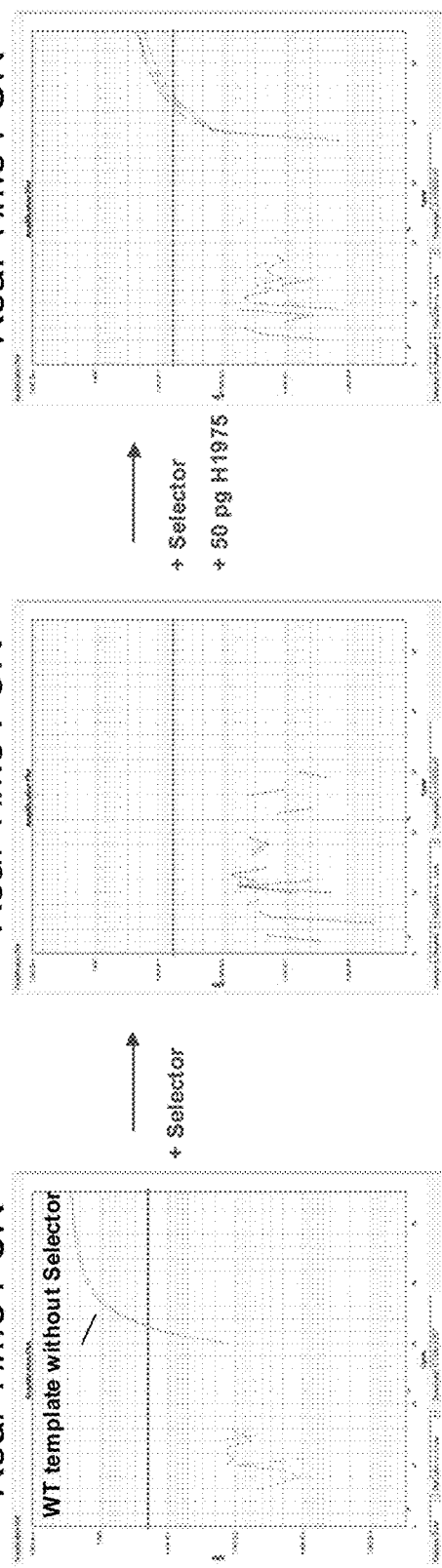
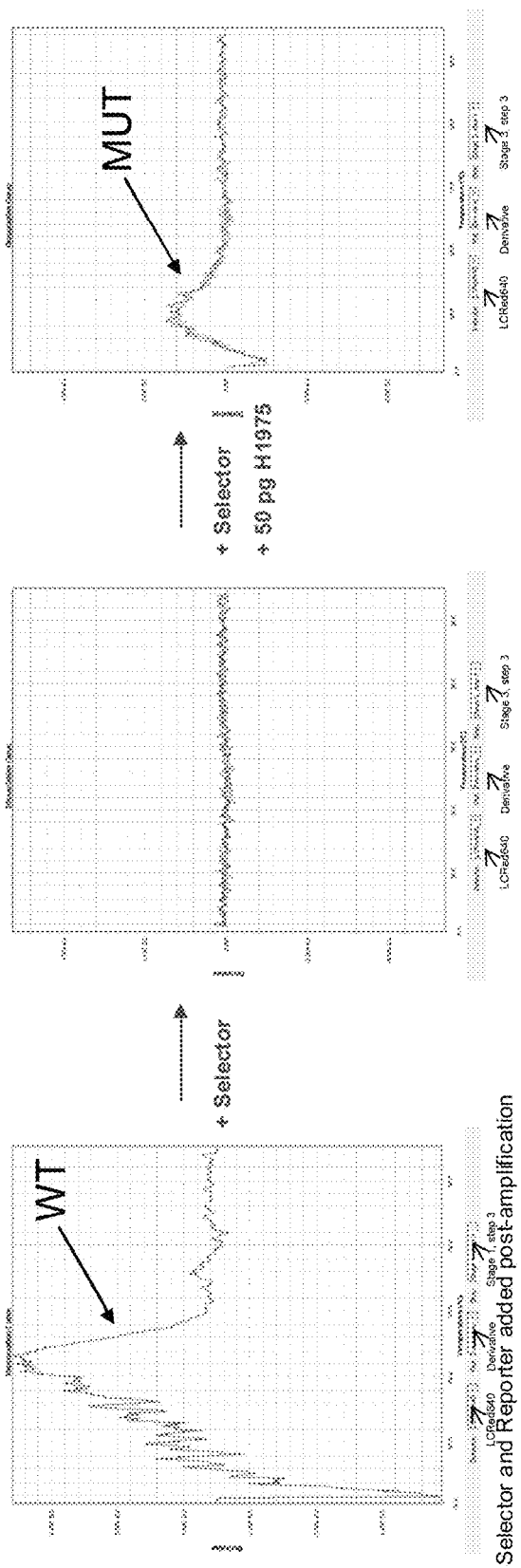
FIG. 15A

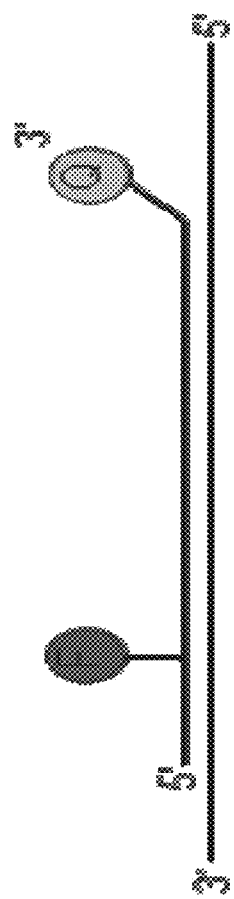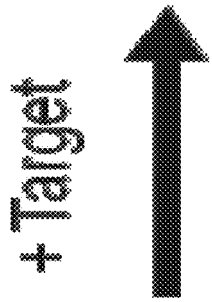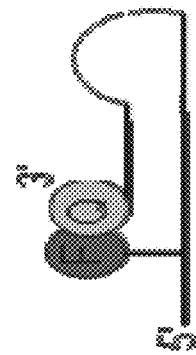
FIG. 21

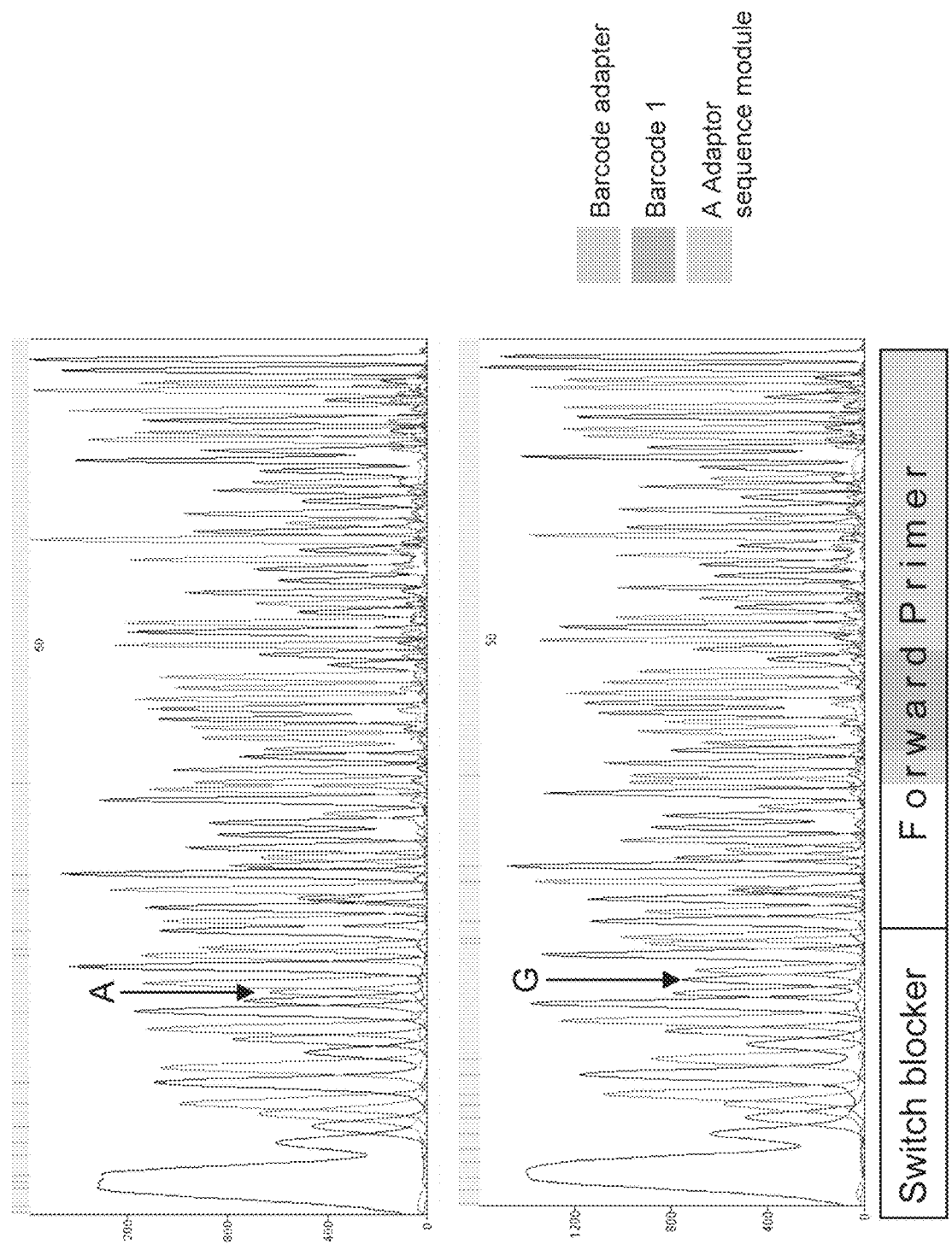

METHODS FOR DETECTING NUCLEIC ACID SEQUENCE VARIANTS

CROSS REFERENCE TO RELATED APPLICATIONS

The present application is a continuation of U.S. patent application Ser. No. 13/841,842, filed Mar. 15, 2013, which is a continuation-in-part and claims priority and benefit under 35 U.S.C. 365(c) of International Patent Application No. PCT/US2012/036678, filed May 4, 2012, which claims priority to U.S. Provisional Patent Application No. 61/482,576, filed May 4, 2011, which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BIOE_028_02US_SeqList_ST25.txt, date recorded: Oct. 30, 2017, file size 21.4 kilobytes).

FIELD OF THE INVENTION

The present invention relates to methods for detecting nucleic acid variants in a target nucleic acid sequence and to methods for high-fidelity sequence amplification.

BACKGROUND

Detection of nucleic acid variants is important with respect to a variety of situations, and critically important with respect to detection and prognosis of diseases. There are currently a wide range of assay formats for detecting nucleic acid variants. Such assays include pyrophosphorolysis-activated polymerization (PAP), assays using LNA blockers, and cast-PCR assays.

Pyrophosphorolysis-activated polymerization (PAP) can be used to measure mutation load or to detect minimal residual disease. In PAP, pyrophosphorolysis and polymerization by DNA polymerase are coupled serially by utilizing a pyrophosphorolysis-activatable oligonucleotide (P*). The activated P* can be extended by DNA polymerization. Specificity of the assay results from both pyrophosphorolysis and polymerization as significant nonspecific amplification requires the combination of mismatch pyrophosphorolysis and misincorporation by the DNA polymerase, which is an extremely rare event. (See, e.g., Liu and Sommer, "Pyrophosphorolysis-activated polymerization (PAP): application to allele-specific amplification," *Biotechniques*, 29(5):1072-6, 1078, 1080 (2000); incorporated by reference herein in its entirety.)

LNA blockers can also be employed with methods of detecting and/or quantifying nucleic acid variants in populations of nucleic acids where the wild-type nucleic acids are in greater abundance. Such methods utilize short high affinity oligonucleotides targeted to the wild type rather than the minority or mutant sequence and which function to block detection of wild type DNA. The LNA blocker probes can be used in combination with longer detection probes or PCR primers to amplify and/or identify the minority or mutant sequence. (See, e.g., US Patent Appl. No. 20100009355; incorporated by reference herein in its entirety.)

Cast-PCR can also be used as an assay for analyzing sequence variation between different alleles. The methods use competitive allele-specific TaqMan PCR ("cast-PCR") to distinguish nucleic acid variants. Cast-PCR employs performing two amplification reactions on a target nucleic acid sequence. The first reaction includes amplification in the presence of a first allele-specific primer and a first allelic specific blocker, which is complementary to the first allelic variant, followed by detection of the amplification product. The second reaction includes amplification in the presence of a second allele-specific primer and a second allelic specific blocker, which is complementary to the second allelic variant, followed by detection of the amplification product. (See, e.g., US Patent Appl. No. 20100221717; incorporated by reference herein in its entirety.)

All of the above methods possess various challenges and limitations. A common problem behind these approaches for detecting rare variants is poor enzyme fidelity. Errors introduced during replication and associated amplification, cannot be easily discriminated from true rare variants and mutations, and thus undermine the performance of these approaches. Additionally, in the case of allele specific priming, such as the amplification refractory mutation system (ARMS, *Nucleic Acids Res.* 17:2503-16 (1989)) mispriming during amplification can "over-write" variant sites and lead to poor results. In most cases specificity of the above methods is limited to 0.1-5% of allele prevalence. This is the case even with next generation sequencing approaches, since the polymerases employed introduce errors sufficient to limit the sensitivity of detection of rare alleles to about 3-5%. A key difficulty with all of these assays is that at their core are amplification methods that use DNA polymerases which due to their infidelity introduce errors that create an intrinsic background in the 1-3% range or more, depending upon the polymerase. A few methods can give much higher levels of specificity, such as digital PCR, but these methods are complex, expensive, and do not interface easily to confirmatory or diagnostic assays. Additionally, digital PCR also does not lend itself to high levels of multiplexing.

There is a need in the art for additional assay methods that can more effectively detect rare nucleic acid sequence variants. Furthermore methods are needed that reduce incorporation errors associated with polymerase associated amplification systems. Additional assays need to be developed and the methods of the present invention provide such additional assay methods.

SUMMARY OF THE INVENTION

The present invention provides methods for detecting the presence or absence of a nucleic acid variant in a target region. These methods include amplifying the target region with a forward primer and a reverse primer in the presence of a selector blocker. The selector blocker includes a sequence complementary to the target region in the absence of the nucleic acid variant. The methods further include detecting amplification of the target region where amplification of the target region indicates the presence of the nucleic acid variant in the target region. The nucleic acid variant can include deletions, mutations, or insertions.

The methods of the present invention can also provide a sensitivity of >1:1000 (i.e., 1 copy of a nucleic acid variant in the target region can be detected in the presence of 1000 copies of a wild type target region). In some embodiments, the sensitivity is a sensitivity >1:1500, >1:2000, >1:2500, >1:3000, >1:3500 or >1:4000, >1:5000, >1:10,000, >1:20:000, >1:50:000, >1:100,000, >1:120,000, >1:150,000, >1:200,000, >1:250,000, >1:500,000, >1:750,000, >1:1,000,000, or more.

The methods can also additionally include using a reporter probe along with a selector blocker. The reporter probe provides a first signal in the presence of amplification and a second signal in the absence of amplification.

The present invention also provides a reaction mixture that includes a forward primer, a reverse primer, a selector blocker, and a template polynucleotide including a target region susceptible to a nucleic acid variant. The selector blocker includes a sequence complementary to the target region in the absence of the nucleic acid variant. The forward primer and the reverse primer are useful for amplifying the region of the template polynucleotide that includes the target region. The reaction mixture can additionally include a reporter probe, where the reporter provides a first signal in the presence of amplification and a second signal in the absence of amplification.

The present invention also provides methods for performing high-fidelity amplification, such methods including in some embodiments the use of nuclease resistant primers in combination with high-fidelity polymerases in the amplification of a nucleic acid target region.

The present invention also provides for kits. A kit contemplated by the present invention can include a forward primer and a selector blocker. The selector blocker contains a sequence complementary to the target region in the absence of the nucleic acid variant. The forward primer comprises a sequence complementary to a region upstream of the target region. The kit can additionally include a reverse primer and a reporter probe. Also contemplated is a kit comprising nuclease resistant primers and high-fidelity polymerases and repair enzymes comprising 3'exo nuclease activity.

DESCRIPTION OF THE FIGURES

FIG. 5A: NTC (No Template Control). FIG. 5B: 100 pg H1975 (Mutant) DNA were used in the Selector Assay. FIG. 5C: 10 ng WBC17088 (Wild-Type) DNA were used in the Selector Assay.

FIG. 6A: NTC (No Template Control, left panel) or 6.6 ng WBC 17088 (Wild-type, right panel) DNA were used in the Selector Assay. FIG. 6B: 14 pg H1975 (Mutant) with 6.6 ng WBC17088 (Wild-Type) DNA were used in the Selector Assay. FIG. 6C: 28 pg H1975 (Mutant) with 6.6 ng WBC17088 (Wild-Type) DNA were used in the Selector Assay.

FIG. 8. Isolation of amplified Iminobiotin labeled strand for melt curve analysis and sequencing.

FIG. 11B: Standard curves of the amplification data shown in FIG. 11A.

FIG. 15A: Selector Assay with a forward primer (FP14ovl) overlapping the Selector.

FIG. 21. A schematic of an exemplary Flip Probe design.

FIG. 22A: Selector assay with No Template Control (NTC), 50 pg H1975, or 500 pg H1975. FIG. 22B: Selector assay with Wild-Type (WT), WT+50 pg H1975, or WT+500 pg H1975.

FIG. 32. Grafting Ion torrent adapters into Selector assay reactions done using the high Tm switch blocker.

FIG. 33A: Selector assay with No Template Control (NTC). FIG. 33B: Selector assay with 50 ng LnCAP.

FIG. 36A: Selector assay with wild-type (LnCAP) template. FIG. 36B: Selector assay with T90M mutant (H1975).

DETAILED DESCRIPTION OF THE INVENTION

Figure 1:
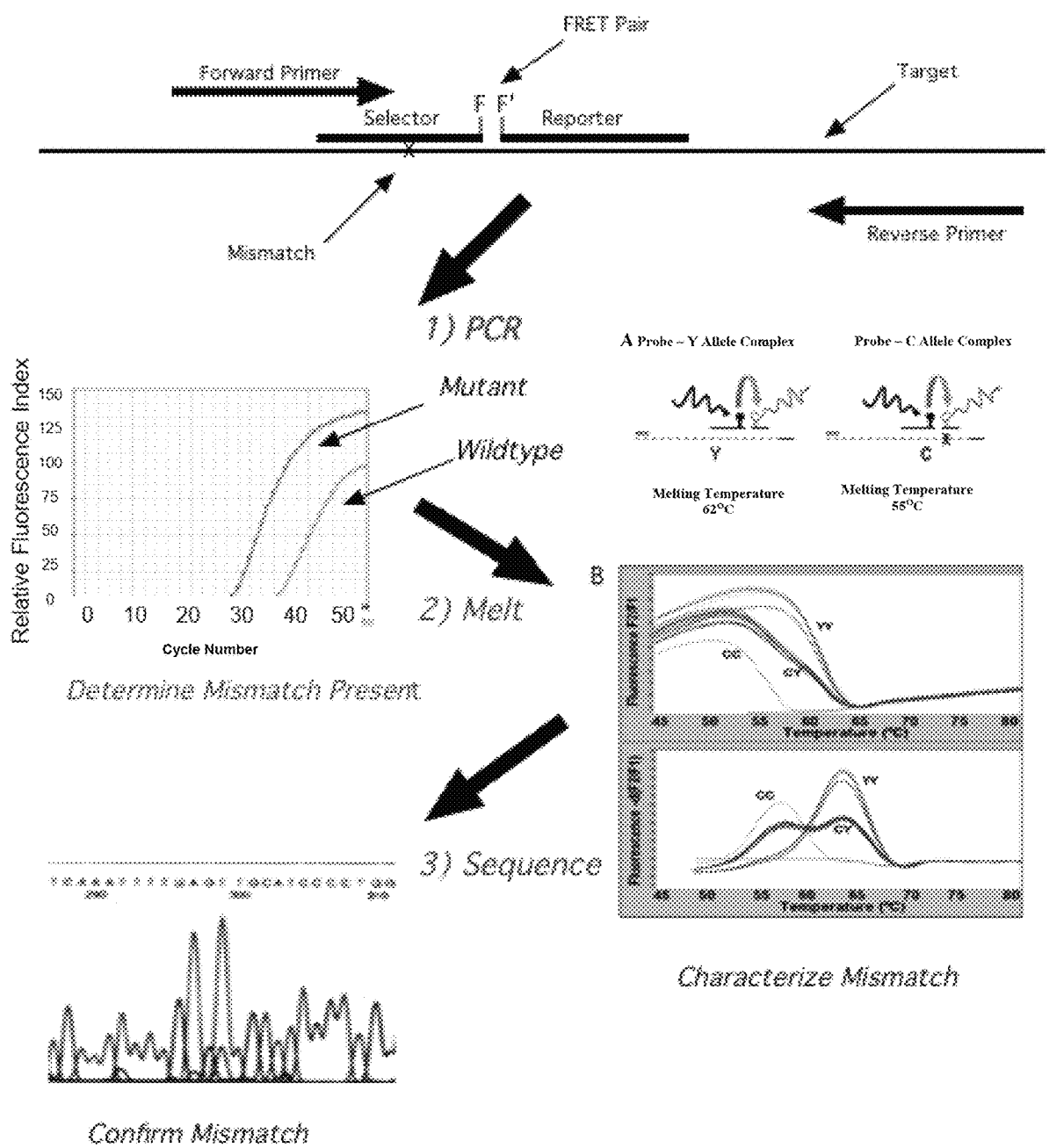
FIG. 1. Schematic representation of the Selector Assay methods as described herein. Regions of the EGFR gene that have mutations are shown (SEQ ID NO: 31).

The methods of the present invention are based in part on the discovery that blocker probes can be used to detect nucleic acid variants with very high sensitivity, in some cases at a sensitivity >1:1000. In some cases at a sensitivity >1:2000. Accordingly, the present invention provides methods for detecting the presence or absence of a nucleic acid variant in a target region. The methods include amplifying the target region with a forward primer and a reverse primer in the presence of a selector blocker. In some embodiments, the selector blocker includes a sequence complementary to the target region in the absence of the nucleic acid variant. The methods further include detecting amplification of the target region, where amplification of the target region indicates the presence of the nucleic acid variant in the target region.

The present invention provides methods for interrogating rare genetic events. As such, the methods of the present invention allow for detection of single variants (e.g., 1 copy of a variant) out of a large number of molecules. In some embodiments, the sensitivity of the methods of the invention is >1:1000 (i.e., 1 copy of a target can be detected out of 1000 copies of a target region). In some embodiments, the sensitivity is a sensitivity >1:1500, >1:2000, >1:2500, >1:3000, >1:3500 or >1:4000, >1:5000, >1:10,000, >1:20:000, >1:50:000, >1:100,000, >1:120,000, >1:150,000, >1:200,000, >1:250,000, >1:500,000, >1:750,000, >1:1,000,000, >1:2,000,000, >1:5,000,000, or more. In some embodiments, 1 copy of a target nucleic acid, such as for example a nucleic acid variant can be detected in the presence at least about 1000, about 1500, about 2000, about 2500, about 3000, about 3500, about 4000, about 5,000, about 10,000, about 20:000, about 50:000, about 100,000, about 120,000, about 150,000, about 200,000, about 250,000, about 500,000, about 750,000, about 1,000,000 or more copies of the wild type nucleic acid.

According to the methods of the present invention, "presence of amplification" and similar terms and phrases can include amplification as well as more, enhanced or increased amplification. According to the methods of the present invention, "absence of amplification" and similar terms and phrases can include no amplification as well as less, reduced or decreased amplification.

In some embodiments, the method includes amplifying the target region with a forward primer and a reverse primer in the presence of a selector blocker. In these embodiments, the selector blocker includes a sequence complementary to the target region in the presence of the nucleic acid variant. The method further includes detecting amplification of the target region, where amplification of the target region indicates the absence of the nucleic acid variant in the target region. In still other embodiments nuclease resistant primers are used in combination with high-fidelity polymerases and repair enzymes that possess 3'exonuclease repair activity.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real-time, single-copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4(1):41-47 (2004); all of which are incorporated by reference herein in their entirety.) In some embodiments, the amplification is by digital PCR. When combined with digital PCR, the present invention can greatly increase the sensitivity of digital PCR. This is due in part to the fact that the current invention provides methods for significantly suppressing (e.g., at least about 60%, 65%, 70%, 75%, 80%, 85%, 90%, 95%, or about 100%) wild-type associated background, when interrogating genetic events, including for example rare genetic events. The sensitivity of targeting provided by the methods of the present invention allows far higher target loading in the individual volume elements of the single digital PCR reactions. In some embodiments, this allows for at least about 10 to 10000 or more targets to be loaded in each volume element (e.g., reaction) of the digital PCR reaction. In some embodiments, this allows for about 10 to 10000, about 10 to 5000, about 10 to 2000, about 10 to 500, about 10 to 100 or more targets to be loaded in each volume element (e.g., reaction mixture) of the digital PCR reaction. In some embodiments, this allows for about 10, 100, 500, 1000, 2000, 5000, 10000 or more targets to be loaded in each volume element (e.g., reaction mixture) of the digital PCR reaction. When running digital PCR for detecting rare genetic events, most of the events present in a given reaction mixture will be of a wild-type sequence while very few will contain the rare genetic event. The methods of the present invention provides for very effective wild-type suppression, for example greater than 1:10000 as described herein. In some embodiments, 10000 wild-type targets can be present in each PCR digital element while still allowing for detection of a single rare target due to the effective suppression of the wild-type amplification combined with not suppressing amplification of the single rare target. In some embodiments, where there are 10000 individual digital PCR volume elements which each contain about 10000 target sequences (e.g., total of wild-type plus genetic variant sequences), the combined number of targets that is being interrogated is 100,000,000. In this embodiment, if 100 positive reactions are significant, this provides for a sensitivity of detection of a genetic variant at 1:1,000,000 compared to wild-type.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

The nucleic acid variants that can be detected by the methods of the present invention include deletions in the target region, mutations in the target region and/or insertions in the target region. Deletions include removal of a nucleotide base from the target region. Deletions that can be detected include deletion of 1, 2, 3, 4 or 5 nucleotide bases from the target region. Mutations can include but are not limited to substitutions (such as transversions and transitions), abasic sites, crosslinked sites, and chemically altered or modified bases. Mutations that can be detected include mutation of 1, 2, 3, 4, 5 or more nucleotide bases within the target region. Insertions include the addition of a nucleotide into a target region. Insertions that can be detected can include insertion of 1, 2, 3, 4 or 5 nucleotide bases into the target region. In some embodiments, a deletion, a mutation and/or an insertion is detected by the methods of the present invention.

The methods of the present invention can also include the use of a selector blocker. In general, the selector blocker includes a sequence that is complementary to a target region susceptible to nucleic acid variant. According to the present invention, the complementary sequence within the selector blocker can be either fully complementary to a target region in the absence of any nucleic acid variant or complementary to the target region except where it has a nucleic acid variant (i.e., partially complementary). In some embodiments, the selector blocker includes a sequence that is complementary to the target region, but not to at least one nucleic acid variant in the target region. In some other embodiments, the selector blocker includes a sequence that is complementary to the target region, but not to at least two or more nucleic acid variants in the target region. In yet other embodiments, the selector blocker includes a sequence that is complementary to the target region, but not to at least 20%, 30%, 40%, 50%, 60%, 70%, 80%, 90%, 95%, or 98% of nucleic acid variants in the target region. In still other embodiments, the selector blocker includes a sequence that is complementary to the target region, but not to certain nucleic acid variants to the extent that such mismatch is sufficient to provide a detectable difference in amplification between the presence and absence of at least one or more nucleic acid variants.

In some embodiments, the selector blocker is an oligonucleotide comprising the formula X-Y-Z, wherein X comprises i) nucleic acid bases or analogs thereof from about 3 to 30 bases that are substantially complementary to the target sequence and wherein Y comprises nucleic acid bases or analogs thereof wherein Y comprises natural and non-natural base with reduced or no base pairing capability with the target sequence, being about 2 to 30 bases in length; or ii) covalent or non-covalent binding interactions that are substantially non-complementary to the target sequence; and Z comprises nucleic acid bases or analogs thereof from about 20 to 200 bases that are substantially complementary to the target sequence. In other embodiments, Y may be a stem loop comprising base pairing nucleic acid bases, and analogs thereof. In some embodiments, Y is about 2 to 30 bases, about 5 to 25 bases, about 10 to 30 bases or about 10 to 20 bases in length. In some embodiments, about 1 to 3 bases are substituted at the base of said stem loop to releave strain. The combined length of X-Y-Z are about 15 to 500 bases and linkers. In some embodiments Z comprises about 3 bases to 50 bases, about 3 bases to 45 bases, about 3 bases to 40 bases, about 3 bases to 35 bases, about 3 bases to 30 bases, about 3 bases to 20 bases or about 3 bases to 10 bases. In some embodiments, Z comprises about 10 bases to 300 bases, about 20 bases to 200 bases, about 30 bases to 150 bases, about 20 bases to 100 bases or about 50 bases to 100 bases. In some embodiments, Y comprises modified nucleic acids. In some embodiments, the modified nucleic acids can include but are not limited to 5-nitroindole, 4-nitrobenzamidazole, inosine, isoguanine, isocytosine, nebularine nucleic acid bases In some embodiments the selector blocker of formula X-Y-Z comprises a detectable label. Such detectable label can be any detectable label described herein or known in the art. In some embodiments, when Y comprises nucleic acids, the Y portion of formula X-Y-Z comprises less than about 20% of the total nucleic acid bases of said oligonucleotide, or less than about 15%, 10%, or 5%. In some embodiments, when Y comprises nucleic acids, Y comprises about 20%, 30%, 40%, 50% or more of the nucleic acid bases of said oligonucleotide.

The methods also provide for determining the difference in the Tm between when the selector-blocker interacts with the target region in the absence versus in the presence of nucleic acid variant. In some embodiments the difference in the Tm between when the selector-blocker interacts with the target region in the absence versus in the presence of nucleic acid variant is maximized. In some embodiments, the Tm difference is 5, 6, 7, 8, 9, 10, 11, 12, 13, 14, 15, 16, 17, 18, 19, 20 or more degrees Celsius. In some embodiments, the Tm difference is 10 to 15 degrees Celsius, 11 to 14 degrees Celsius, or 12 to 13 degrees Celsius. In some embodiments, the Tm difference can be 2 to 3 degrees Celsius. In some embodiments, the higher the Tm discrimination between the target region in the absence and presence of the nucleic acid variant, the more significant the differences in amplification of the target region in the absence and presence of the nucleic acid.

Complementary can also be described in the context of melting temperature (Tm), where complementary refers to a gradient of more and less complementary sequences and including for example sequences that are more complementary relative other sequences but where no sequence is fully complementary (i.e., fully and partially complementary sequences). Sequences that are more complementary generally exhibit a higher Tm than sequences that are less complementary (i.e., a sequence that exhibits 98% complementary would have a higher Tm than a sequence that exhibits 40% complementary). In the methods of the present invention, generally the sequence that exhibits more sequence complementarity will exhibit a higher Tm when interacting with the target region.

In some embodiments, such as where sequences are particularly G/C or A/T rich, the Tm and complementarity may be reversed, for example a sequence with higher complementarity but which is A/T rich could have a lower Tm than a sequence with lower complementarity and but which is G/C rich. The methods of the present invention would still be applicable as such information regarding the interaction between Tm and sequence is well known in the art and one of skill could readily adapt the present methods appropriately.

According to the present invention, the selector blocker can also be configured to comprise a nucleic acid sequence referred to as the "switch sequence". A selector blocker comprising a switch sequence as described in the methods of the present invention is also referred to as a "switch-blocker".

The switch sequence of the switch-blocker is a short nucleic acid sequence located at the 5' region of the switch-blocker and which comprises 3 or more nucleotides, for example 3, 4, 5, 6, 7, 8, 9, 10, 15, 20 or 25 or more nucleotides. The switch sequence binds tightly to a target region due to it being held in high concentration proximal to its complementary sequence. In some embodiments, the switch sequence binds to the section of the target region containing one or more nucleic acid variants. In some embodiments 1, 2, 3, 4, 5, 6, 7 or more nucleic acid variations (including for example mismatches, deletions, insertions, or mutations) between the switch sequence and the target sequence is sufficient to cause detectable difference in amplification between the presence and absence of at least one or more nucleic acid variants. In some embodiments, the sequence difference(s) between the switch sequence and the target sequence is sufficient to disrupt or prevent binding of the switch sequence to the target sequence. In some embodiments, the switch sequence is complementary (fully or partially) to the target region including one or more locations where nucleic acid variants occur. In some other embodiments, the switch sequence is complementary (fully or partially) to the target region except at least one location where nucleic acid variant occurs.

In some embodiments, the switch-blocker comprises a switch sequence linked to a longer nucleic acid sequence that is complementary to the target region, referred to as a "long hybridizing region". A long hybridizing region can be about 10, 20, 30, 40, 50, 60, 70, 80, 90, 100 or more nucleotides in length. In some embodiments, the long hybridizing region targets the switch-blocker to the target region of a nucleic acid sequence by binding to a complementary region adjacent to or near the target region. The switch sequence can be linked or conjugated to the long hybridizing region using the linkage or conjugation methods described herein, through bridging nucleotide sequences or through any other linkage or conjugation methods known in the art.

The present invention also provides methods for steric blocking. In some embodiments, the selector blocker and/or switch-blocker function as steric blockers and prevents the extension of a distant forward primer. In some embodiments, the forward primer can be located 0, 5, 10, 15, 20, 25, 30, 35, 40, 45, 50, 55, 60, 80, 100, 250, 500, 1000, 2000 or more nucleotides away from the region where the selector blocker or switch blocker hybridize. In some embodiments, the selector blocker has a sufficiently high Tm that it is not displaced by a replicating forward primer. In some embodiments, the enzyme used during the amplification reaction does not comprise a strand displacement activity. Exemplary enzymes for use with the methods of the invention can include but are not limited, Pfu Turbo Hotstart DNA Polymerase, Phusion® Hot Start High Fidelity DNA Polymerase, Phusion Hot® Start II High Fidelity DNA Polymerase, Phire® Hot Start DNA Polymerase, Phire® Hot Start II DNA Polymerase, KOD Hot Start DNA Polymerase, Q5 High Fidelity Hot Start DNA Polymerase, and Kapa HiFi. In some embodiments, the selector blocker prevents the extension of the forward primer at temperatures of 30° C., 40° C., 50° C., 55° C., 60° C., 65° C., 70° C., 75° C. or higher.

Nucleic acids, such as for example the switch sequence and the long hybridizing region, can be linked together or conjugated by a variety of methods. Linkage or conjugation of nucleic acid sequences can be achieved through various linking moieties and conjugation methods, a variety of which are well known in the art any of which can be used with the methods of the present invention. Linkage or conjugation can be achieved by synthesizing the individual nucleic acid elements and conjugating them using conventional conjugation methods (*Current Protocols in Nucleic Acid* Chemistry, 2001-2011; and *Bioconjugate Techniques*, $2^{nd}$ Ed., Hermanson G., T., Academic Press, Inc., 2008.) Such methods can include zero-length crosslinkers, homo-bifunctional crosslinkers, heterobifunctional Crosslinkers (such as for example, NHS/maleimide heterobifunctional linker), trifunctional crosslinkers, and photoreactive crosslinkers. Homobifunctional crosslinkers can include for example amine-to-amine crosslinkers, sulfhydryl-to-sulfhydryl crosslinkers and thiol-to-thiol crosslinkers. Heterobifunctional crosslinkers can include for example amine-to-sulfhydryl crosslinkers, carboxyl-to-amine crosslinkers, sulfhydryl-to-carbohydrate crosslinkers, sulfhydryl-to-hydroxyl crosslinkers, amine-to-thiol crosslinkers and amine-to-carboxylic acid crosslinkers. In some embodiments, the forward primer and selector blocker are synthesized such that they contain the appropriate groups for use with the desired crosslinking reagent. In some embodiments, the forward primer and selector blocker are synthesized using a combination of 3'phosphoramidites, 5'phosphoramidites, and phosphoramidite linkers, including but not limited to Spacer Phosphoramidite 12 and 18 (Glen Research).

Examples of linkers and crosslinkers include but are not limited to C18 diacid based crosslinkers (such as diacrylate and dimethacrylate crosslinkers); Z elements; bis[sulfosuccinimidyl] suberate (BSSS or BS3); disuccinimidyl suberate (DSS); Bis[Sulfosuccinimidyl] glutarate (BS2G); dithiobis [succinimidyl propionate] (DTSP or DSP); (3,3'-Dithiobis [sulfosuccinimidylpropionate])(DTS SP); disuccinimidyl glutarate (DSG); Ethylene glycolbis(sulfosuccinimidylsuccinate); Ethylene glycolbis(succinimidylsuccinate); disuccinimidyl tartrate; and NHS/maleimide heterobifunctional linkers, aryl azides, benzophenone derivatives.

Bridging nucleotide sequences include those nucleotide sequences that align with adjacent nucleotide sequences in a target nucleic acid but that do not bind to complementary bases of the target through Watson-Crick hydrogen bonding interactions. Such bases include, but are not limited to, deoxyinosine and 5-nitroindole-2'-deoxyriboside.

The present invention also provides for the introduction of detectable labels into the switch-blocker. In some embodiments, the switch-blocker can function as a reporter probe.

According to the present invention, the selector blocker can be extendable or non-extendable. The selector blocker can in some cases be modified by a variety of methods known in the art to protect against 3' or 5' exonuclease activity. The selector blocker can also include one or more modifications to protect against 3' or 5' exonuclease activity and such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the selector blocker is resistant to 3' and/or 5' exonuclease activity due to the presence of one or more modifications.

The methods of the present invention also provide for using a selector blocker that has an increased affinity for the target sequence. Such selector blockers can include selector blockers with increased length, as well as chemical modifications to the selector blocker. Such modifications can include 2'fluoro (2'-Deoxy-2'-fluoro-nucleosides) modifications, LNAs (locked nucleic acids), PNAs (peptide nucleic acids), ZNAs (Zip Nucleic Acids), morpholinos, methylphosphonates, phosphoramidates, polycationic conjugates and 2'pyrene modifications. In some embodiments, the selector blocker contains one or more modifications including 2'fluoro modifications (aka, 2'-Deoxy-2'-fluoro-nucleosides), LNAs (locked nucleic acids), PNAs (peptide nucleic acids), ZNAs (Zip Nucleic Acids), morpholinos, methylphosphonates, phosphoramidates, and/or polycationic conjugates. In some embodiments, the selector blocker does not contain a PNA or a LNA.

The selector blocker of the present invention can also find therapeutic use. In some embodiments the selector blocker can be administered as a therapeutic agent to prevent, for example, gene translation and/or gene expression. In some embodiments, the selector blocker is capable of blocking gene expression. In some embodiments, the selector blocker therapeutic is capable of preventing mRNA expression. In some embodiments, the selector blocker is modified in order to increase in vivo stability, including but not limited to comprising modified nucleic acids. In some embodiments, the selector blocker contains 3' end and/or 5' end modifications that increase stability, prevent degradation and or prevention other modifications of the selector blocker in vivo. In some embodiments, the selector blocker comprises a 2'O-methyl modification. In other embodiments, the selector blocker comprises a 2' fluoro modification.

The selector blocker can also contain a detectable entity. Such detectable entities can include for example but are not limited to fluorescent labels and chemiluminescent labels. Such detectable entities can also include members of FRET pairs. In some embodiments, the selector blocker contains a detectable entity.

Fluorescent labels can include but are not limited to AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamine; 5-FAM ethylenediamine; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4', 5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamine; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamine; 6-TAMRA ethylenediamine; 5-TMR C6 malemide; 6-TMR C6 malemide; TR C2 malemide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Chemiluminescent labels can include but are not limited to those labels used with Southern Blot and Western Blot protocols (see, for e.g., Sambrook and Russell, *Molecular Cloning: A Laboratory Manual*, (3rd ed.) (2001); incorporated by reference herein in its entirety). Examples include but are not limited to -(2'-spiroadamantane)-4-methoxy-4-(3"-phosphoryloxy)phenyl-1,2-dioxetane (AMPPD); acridinium esters and adamantyl-stabilized 1,2-dioxetanes, and derivatives thereof.

According to the present invention, the forward primer can be designed to be complementary (fully or partially) to various suitable positions relative to one or more nucleic acid variants. In some embodiments, the 3' region of the forward primer be complementary (fully or partially) to the target region at a variety of positions with respect to the position of one or more nucleic acid variant. For example, the 3' region of the forward primer when hybridized to the target region in some cases can be located −5, 0, 5, 10, 15, 20, 25, 30, 35, 40, 45, 50, 55, 60, 80, 100, 250, 500, 1000, 2000 or more nucleotides away from one or more nucleic acid variants in the target region. In some embodiments, the 3' region of the forward primer when hybridized to the target region is located less than about 30 nucleotides away from one or more nucleic acid variants in the target region.

In some instances, the forward primer and selector blocker can compete for hybridizing to a partial or full target region and this can lead to increased sensitivity. For example, the forward primer and selector blocker can overlap by 0, 5, 10, 15, or more nucleotides. In some embodiments, the 3' region of the forward primer that hybridizes to the target region overlaps with the 5' region of the selector blocker that hybridizes to the target region. In some embodiments, when the primer and the selector blocker overlap at the 5' region of the selector blocker the overlapping region does not contain nucleic acid variant(s). The forward primer and/or the selector blocker can in some cases be modified by a variety of methods known in the art to protect against 3' or 5' exonuclease activity. The forward primer and/or the selector blocker can include one or more modifications and such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the forward primer and/or the selector blocker is protected against 3' or 5' exonuclease activity.

In some embodiments, the selector blocker and forward primer are linked or conjugated to each other and this combination is also referred to as a "primer-switch". Nucleic acids, such as for example the forward primer and the selector blocker, can be linked together or conjugated by a variety of methods. Linkage or conjugation of nucleic acid sequences can be achieved through various linking moieties and conjugation methods as well as through non-covalent attachment, a variety of which are well known in the art any of which can be used with the methods of the present invention. Linkage or conjugation can be achieved by synthesizing the individual nucleic acid elements and conjugating them using conventional conjugation methods (*Current Protocols in Nucleic Acid Chemistry*, 2001-2011; and *Bioconjugate Techniques*, 2nd Ed., Hermanson G., T., Academic Press, Inc., 2008.) Such methods can include zero-length crosslinkers, homobifunctional crosslinkers, heterobifunctional Crosslinkers (such as for example, NHS/maleimide heterobifunctional linker), trifunctional crosslinkers, and photoreactive crosslinkers. Homobifunctional crosslinkers can include for example amine-to-amine crosslinkers, sulfhydryl-to-sulfhydryl crosslinkers and thiol-to-thiol crosslinkers. Heterobifunctional crosslinkers can include for example amine-to-sulfhydryl crosslinkers, carboxyl-to-amine crosslinkers, sulfhydryl-to-carbohydrate crosslinkers, sulfhydryl-to-hydroxyl crosslinkers, amine-to-thiol crosslinkers and amine-to-carboxylic acid crosslinkers. In some embodiments, the forward primer and selector blocker are synthesized such that they contain the appropriate groups for use with the desired crosslinking reagent. In some embodiments, the forward primer and selector blocker are synthesized using a combination of 3'phosphoramidites, 5'phosphoramidites, and phosphoramidite linkers, including but not limited to Spacer Phosphoramidite 12 and 18 (Glen Research). Non-covalent attachment can include the use of hybridization or affinity mechanisms to link the nucleic acids together. For example, the selector blocker and forward primer can comprise short nucleic acid regions (which can be referred to as stem regions), which are capable of undergoing hybridization. In some embodiments, the 3' end of the one nucleic acid, e.g., the selector, contains the stem and the 5' end of the other nucleic acid, e.g. a reporter or Flip-probe contains, the stem, wherein the stems are capable of hybridization. In some embodiments, the non-covalent attachment uses a metal chelating agent, e.g., metal ion affinity chromatography agents. In some embodiments, other affinity interactions are employed.

Examples of linkers and crosslinkers include but are not limited to C18 diacid based crosslinkers (such as diacrylate and dimethacrylate crosslinkers); Z elements; bis[sulfosuccinimidyl] suberate (BSSS or BS3); disuccinimidyl suberate (DSS); Bis[Sulfosuccinimidyl] glutarate (BS2G); dithiobis [succinimidyl propionate] (DTSP or DSP); (3,3'-Dithiobis [sulfosuccinimidylpropionate])(DTS SP); disuccinimidyl glutarate (DSG); Ethylene glycolbis(sulfosuccinimidylsuccinate); Ethylene glycolbis(succinimidylsuccinate); disuccinimidyl tartrate; and NHS/maleimide heterobifunctional linkers, aryl azides, and benzophenone derivatives.

According to the present invention, when the forward primer and the selector blocker are linked by any suitable means known or later discovered, e.g., in the context of a "primer-switch", both the forward primer and the selector blocker can have a sequence complementary to the same target region, except they differ at location(s) where nucleic acid variant(s) occur. In some embodiments, the forward primer of the primer switch has a sequence that is complementary to the target region except at least one location where nucleic acid variant occurs whereas the selector blocker of the primer switch has a sequence that is complementary to the same target region including one or more location(s) where nucleic acid variant(s) occur. In some other embodiments, the forward primer of the primer switch has a sequence that is complementary to the target region including at one or more location(s) where nucleic acid variant(s) occur whereas the selector blocker of the primer switch has a sequence that is complementary to the same target region except at least one location where nucleic acid variant occurs. In some embodiments, the selector blocker has a higher Tm than the forward primer. In some embodiments, the selector blocker has a lower Tm than the forward primer.

The methods of the present invention also provide for using the selector blocker in conjunction with a reporter probe or in conjunction with the switch blocker as a reporter probe. In some embodiments, the reporter probe is used along with a selector blocker.

The reporter probe can be extendable or non-extendable. The reporter probe can in some cases be modified by a variety of methods known in the art to protect against 3' or 5' exonuclease activity. The reporter probe can include one or more modifications and such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the reporter probe is protected against 3' or 5' exonuclease activity.

The reporter probe and the switch-blocker can also contain a fluorescent label and a quencher. Fluorescent labels can include but are not limited to those described herein. Quenchers can include but are not limited to DABCYL C2 amine; DABCYL C2 maleimide; DABCYL acid (4-((4-(Dimethylamino)phenyl)azo)benzoic acid); DABCYL acid (4-((4-(Dimethylamino)phenyl)azo)benzoic acid); DABCYL acid (4-((4-(Dimethylamino)phenyl)azo)benzoic acid); DABCYL succinimidyl ester (4-((4-(Dimethylamino)phenyl)azo)benzoic acid, succinimidyl ester); DABCYL succinimidyl ester (4-((4-(Dimethylamino)phenyl)azo)benzoic acid, succinimidyl ester); DABSYL chloride (4-Dimethylaminoazobenzene-4-sulfonyl chloride); DNP amine; DNP maleimide; DNP-X acid (6-(2,4-Dinitrophenyl)aminohexanoic acid); DNP-X acid, SE (6-(2,4-Dinitrophenyl) aminohexanoic acid, succinimidyl ester) and derivatives thereof. In some embodiments, when the reporter probe is used along with the selector blocker, the reporter probe contains only a fluorescent label. In some embodiments, when the reporter probe is used along with the selector blocker, the reporter probe contains a fluorescent label and a quencher. In some embodiments, the reporter provides a first signal in the presence of amplification and a second signal in the absence of amplification. The first and second can signals occur, for example, due to the reporter probe hybridizing to the target region and the reporter probe not hybridizing to the target region.

The 5' end of the reporter probe and the 3' end of the selector blocker can include entities that allow for energy transfer to occur. The 5' end can contain the entity that allows for energy transfer at the 5' end or 1, 2, 3, 4, 5, 6, or 7 or more nucleotides from the 5' end. In some embodiments the entity that allows for energy transfer is located 5 nucleotides from the 5' end. In some embodiments, when the reporter is used in conjunction with the selector blocker, the reporter probe contains a first entity at its 5' end and the selector blocker contains a second entity at its 3' end, such that an energy transfer can occur between the first entity and the second entity when the selector blocker and the reporter probe hybridize to the target region. The 3' end can contain the entity that allows for energy transfer at the 3' end or 1, 2, 3, 4, 5, 6, or 7 or more nucleotides from the 3' end.

In some cases, the first and second entities that allow for energy transfer are part of a FRET pair. FRET (Fluorescence Resonance Energy Transfer or Förster Resonance Energy Transfer) is a distance-dependent interaction between the excited states of two entities where excitation energy is transferred from a donor entity to an acceptor entity without emission of a photon. FRET pairs can include but are not limited to 6-FAM (donor) and LC Red 640 or Alexa Fluor 546 (acceptors); fluorescein (donor) and tetramethylrhodamine (acceptor); IAEDANS (donor) and fluorescein (acceptor); EDANS (donor) and Dabcyl (acceptor); fluorescein (donor) and fluorescein (acceptor); BODIPY FL (donor) and BODIPY FL (acceptor); and fluorescein (donor) and QSY 7 and QSY 9 dyes (acceptors).

The methods of the present invention can also further include detecting amplification of the target region using any detection method well known in the art. For example, detection can be by obtaining melting curves for the amplified products, by mass spectrometry or by sequencing of the amplified products. Amplification products will exhibit different melting curves depending on the type and number of nucleic acid variants in the amplification product. Methods for determining melting curves have been well described and are well known to those of skill in the art and any such methods for determining melting curves can be employed with the methods of the present invention. Methods for the use of mass spectrometry as well as methods for sequencing nucleic acids are also well known in the art. (See, for e.g., Sambrook and Russell, *Molecular Cloning: A Laboratory Manual*, (3rd ed.) (2001) and Plum, Optical Methods, *Current Protocols in Nucleic Acid Chemistry*, 2001-2011); all of which are incorporated by reference herein in their entirety). (See, for e.g., *Current Protocols in Nucleic Acid Chemistry*, 2001-2011, specifically *Liquid Chromatography-Mass Spectrometry Analysis of DNA Polymerase Reaction Products*; incorporated by reference herein in its entirety.) Methods for nucleic acid sequencing are also routine and well known by those skilled in the art and any methods for sequencing can be employed with the methods of the present invention. (See, e.g., *Current Protocols in Molecular Biology*, 1995-2010; incorporated by reference herein in its entirety.) In some embodiments, melting curves and sequencing reactions can be used to characterize the nucleic acid variant.

The methods of the invention further include detecting amplification of the target region by comparing the quantity of the amplified product to a predetermined level associated with the presence or absence of the nucleic acid variant in the target region. Methods for detecting amplification or determining the quantity of an amplified product are well known in the art and any such methods can be employed. (See, e.g., Sambrook and Russell, *Molecular Cloning: A Laboratory Manual* (3$^{rd}$ ed.) (2001) and Gallagher, *Current Protocols Essential Laboratory Techniques*, 2008); all of which are incorporated by reference herein in their entirety.)

A predetermined level associated with presence or absence of the nucleic acid variant in the target region can be determined by determining a standard level associated with the nucleic acid variant in the target region in a sufficiently large number of samples and using that level as the predetermined level. Further, standard level information and methods for determining standard levels can be obtained from publically available databases, as well as other sources. The predetermined level can be the predetermined level of amplification that that would be present in a given sample for amplification of a nucleic acid that does not contain a nucleic acid variant in the target region. The predetermined level can also be the predetermined level of amplification that that would be present in a given sample for amplification of a nucleic acid that does contain a nucleic acid variant in the target region. (See, e.g., Bunk, D. M., "Reference Materials and Reference Measurement Procedures: An Overview from a National Metrology Institute," *Clin. Biochem. Rev.*, 28(4):131-137 (2007); incorporated by reference herein in its entirety). Comparison to the predetermined level can be done by any method known to a skilled artisan and any of the above predetermined levels can be used in such comparisons (see, e.g., Sambrook and Russell, *Molecular Cloning: A Laboratory Manual* (3$^{rd}$ ed.) (2001); incorporated by reference herein in its entirety).

The amplification product can also be quantitated using any methods known in the art, such as for example, using nucleic acid markers such as actin or GAPDH. The quantitation can also be based on a normalization control, which can be added to the amplification reaction in a known amount. Such methods are well known and have been described. (See, e.g., Sambrook and Russell, *Molecular Cloning: A Laboratory Manual* (3$^{rd}$ ed.) (2001); incorporated by reference herein in its entirety.)

The present invention also includes a reaction mixture. The reaction mixture can include at least one nuclease resistant primer and a high-fidelity enzyme or a combination of enzymes with 3' exonuclease repair activity. The reaction mixture can also include a forward primer, a reverse primer, a selector blocker, a primer-switch, or a switch-blocker, and a template polynucleotide that includes the target region susceptible to a nucleic acid variant. In some embodiments, the selector blocker, primer-switch blocker, or switch-blocker in the reaction mixture can contain a sequence complementary to the target region in the absence of the nucleic acid variant. In some embodiments, the selector blocker, primer-switch blocker, or switch-blocker in the reaction mixture can contain a sequence complementary to the target region in the presence of the nucleic acid variant. The forward primer and the reverse primer in the reaction mixture are useful for amplifying a region of the template polynucleotide that includes the target region. In some embodiments, the reaction mixture additionally contains a reporter probe or switch-blocker that provides a first signal in the presence of amplification and a second signal in the absence of amplification. In some embodiments, the reaction mixture contains an amplicon produced by amplification of the template nucleotide by the forward primer and the reverse primer.

The present invention also provides for kits. A kit contemplated by the current invention can contain a nuclease resistance primer and a high-fidelity enzyme or combination of enzymes with 3' exonuclease repair activity. Kits contemplated by the present invention can also contain a forward primer, a primer-switch, a selector blocker or a switch-blocker. In some embodiments, the primer-switch, selector blocker, and switch-blocker have greater sequence complementary to the target region in the absence of the nucleic acid variant and the forward primer contains a sequence complementary to a region upstream of the target region. In some embodiments, the primer-switch, selector blocker, and switch-blocker have greater sequence complementary to the target region in the presence of the nucleic acid variant and the forward primer contains a sequence complementary to a region upstream of the target region. In some embodiments, the kit additionally contains a reverse primer and a reporter probe.

The present invention also provides methods for high-fidelity amplification of a nucleic acid target region. Such methods include the use of reagents including nuclease resistant primers, high-fidelity enzymes, blockers, FRET probes and Flip probes during nucleic acid amplification reactions. These can be used alone or in any combination and can be used with any nucleic acid amplification methods known in the art. This aspect of the invention has applications to many polymerase based amplification systems, including for example but not limited to PCR, emulsion PCR, and solid phase amplification associated with next generation sequencing platforms.

In some embodiments, nuclease resistant primers, high-fidelity enzymes, blockers, FRET probes and Flip probes are used in the amplification reaction. In some embodiments, nuclease resistant primers, high-fidelity enzymes, blockers and FRET probes are used. In some embodiments, nuclease resistant primers, high-fidelity enzymes and blockers are used. In some embodiments, nuclease resistant primers and high-fidelity enzymes are used. In some embodiments, nuclease resistant primers and blockers are used.

In some embodiments, one or more of nuclease resistant primers, high-fidelity enzymes, blockers and FRET probe are used with the selector blocker, primer-switch, switch-blocker and/or any of the other methods that are described herein.

Nuclease resistant primers include primers that have been modified to prevent degradation by exonucleases. In some embodiments, the primers have been modified to protect against 3' or 5' exonuclease activity such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proof-reading capabilities. Enzymes that can be used with the methods include but are not limited to AmpliTaq, Phusion HS II, Deep Vent, and Kapa HiFi DNA polymerase.

Blockers can include any modified nucleotide or agent that binds to a nucleotide or agent that binds to a modified nucleotide that is capable of preventing or inhibiting replication and is incorporated into the primer(s) and/or probe(s) in an amplification reaction. Blockers can include 2'fluoro (2'-deoxy-2'-fluoro-nucleosides) modifications, nuclease resistant nucleotides, or nucleotides with 3'-modifications all of which inhibit or prevent replication.

Nuclease resistant nucleotides include but are not limited to 2'-O-methyl ribonucleotides, phosphorothioate nucleotides, phosphorodithioate nucleotides, phosphoramidate nucleotides, and methylphosphonate nucleotides.

Nucleotides with 3'-modifications include but are not limited to 3' terminal phosphate modified nucleotides, 3' alkyl substituted nucleotide, dideoxy nucleotides.

2'fluoro (2'-Deoxy-2'-fluoro-nucleosides) modifications of oligonucleotides can employ a variety of fluorescent labels as the fluoro group, including not limited to AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamine; 5-FAM ethylenediamine; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Caroxyrhodamine 6G cadaverine; 5(6)-Caroxyrhodamine 6G ethylenediamine; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamine; 6-TAMRA ethylenediamine; 5-TMR C6 malemide; 6-TMR C6 malemide; TR C2 malemide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

FRET (Fluorescence Resonance Energy Transfer or Förster Resonance Energy Transfer), as discussed above, can also be employed in nucleic acid amplification. FRET pairs can include but are not limited to 6-FAM (donor) and LC Red 640 or Alexa Fluor 546 (acceptors); fluorescein (donor) and tetramethylrhodamine (acceptor); IAEDANS (donor) and fluorescein (acceptor); EDANS (donor) and Dabcyl (acceptor); fluorescein (donor) and fluorescein (acceptor); BODIPY FL (donor) and BODIPY FL (acceptor); and fluorescein (donor) and QSY 7 and QSY 9 dyes (acceptors).

Flip probes of the invention are self-quenching probes that have four segments and two or more labels. A first target region hybridizing segment of about 1 to 7 bases, a first label, a second target region hybridizing segment of about 4 to 10 bases, a third target region hybridizing segment of about 4 to 9 bases, a fourth segment of about 4 to 10 bases and a second label. (See, for example, FIG. 21.) In some embodiments, the second segment and the forth segment are complementary to each other such that in the absence of a target region the second segment and forth segment hybridize to position the first and second labels in close proximity to each other. In some embodiments, the first label is a fluorophore and the second label is a quencher. In some embodiments, the first label is a quencher and the second label is a fluorophore. In some embodiments, the fluorophore is the first label and the quencher is the second label. In some embodiments, the fluorophore is near the 5' end of the Flip Probe and is in close proximity to the label on the 3' end of the Selector probe to enable FRET interactions when the probe is not bound to a target region. In some embodiments, the first segment of the Flip Probe is used to "space" the distance between the two labels for optimal FRET interactions.

In some embodiments, the Flip Probe is employed with selector blocker, primer-switch, switch-blocker and/or any of the other methods that are described herein. In these embodiments, the Flip Probe is designed to produce high levels of quenching in the absence of target whereas in the presence of target region the Flip probe is designed to bind to the target sequence and to produce significant fluorescence. In some embodiments, binding to the target region allows for the fluorescent absorber located on the Flip Probe to energy transfer through FRET to an emitter located on the Selector blocker.

Instrumentation for performing the methods described herein is readily available. Such instruments can include instruments for real-time and end-point PCR assays, emulsion PCR, solid-phase PCR, melting curve analyses, and sequencing analyses. Such instruments include Life Technologies 7500 Fast Dx real-time instrument (which is also capable of high-resolution melting curve analyses) and the 3500xl capillary gel instruments. Other instruments known in the art to be useful in the methods of the present invention are also contemplated for use by one of skill in the art in practicing the methods of the present invention.

EXAMPLES

Example 1. Design of Selector Assay for EGFR T790M Mutation Detection

Figure 2:
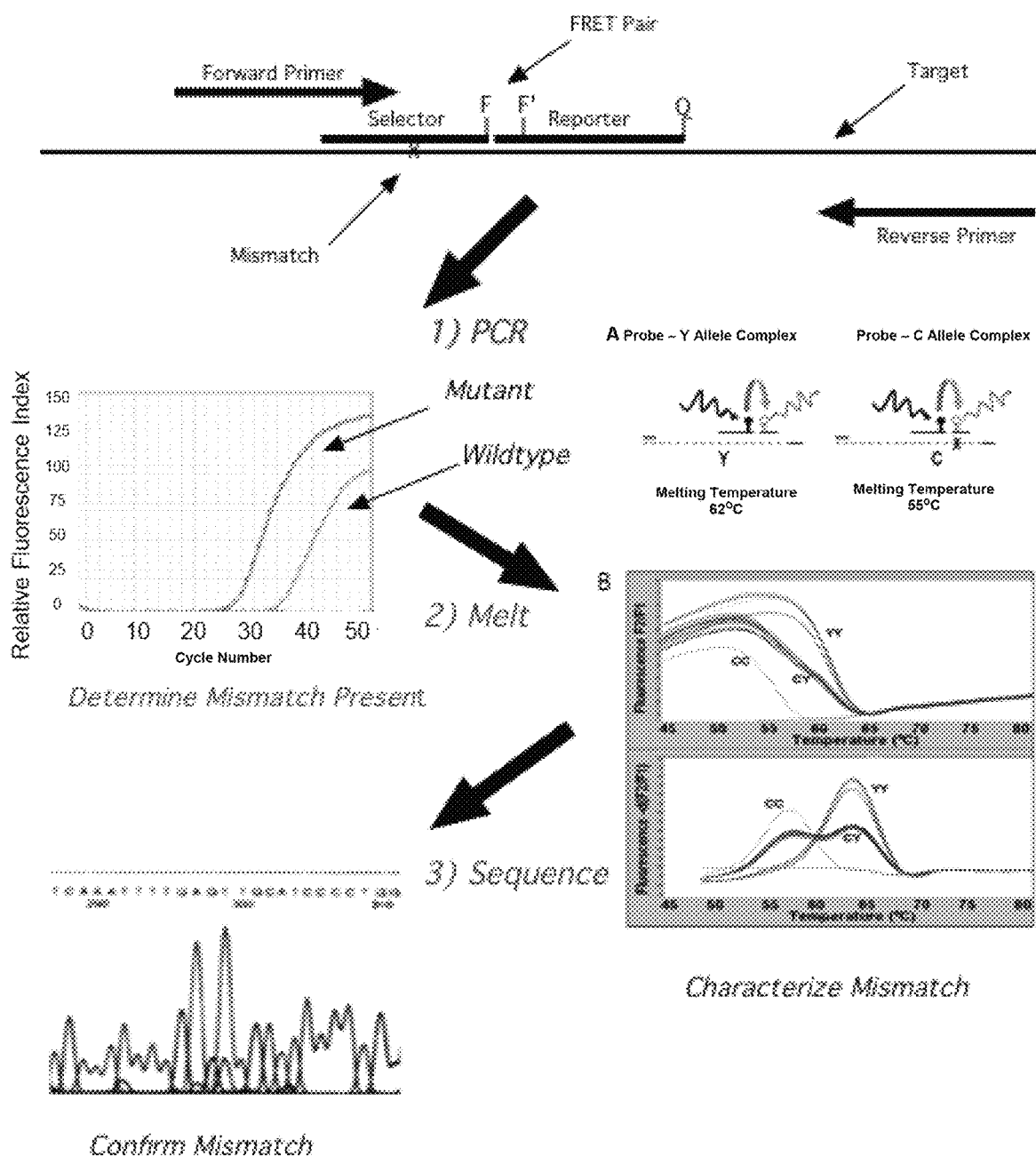
FIG. 2. Schematic representation of the Selector Plus Assay methods as described herein. Regions of the EGFR gene that have mutations are shown (SEQ ID NO: 31).
Figure 3:
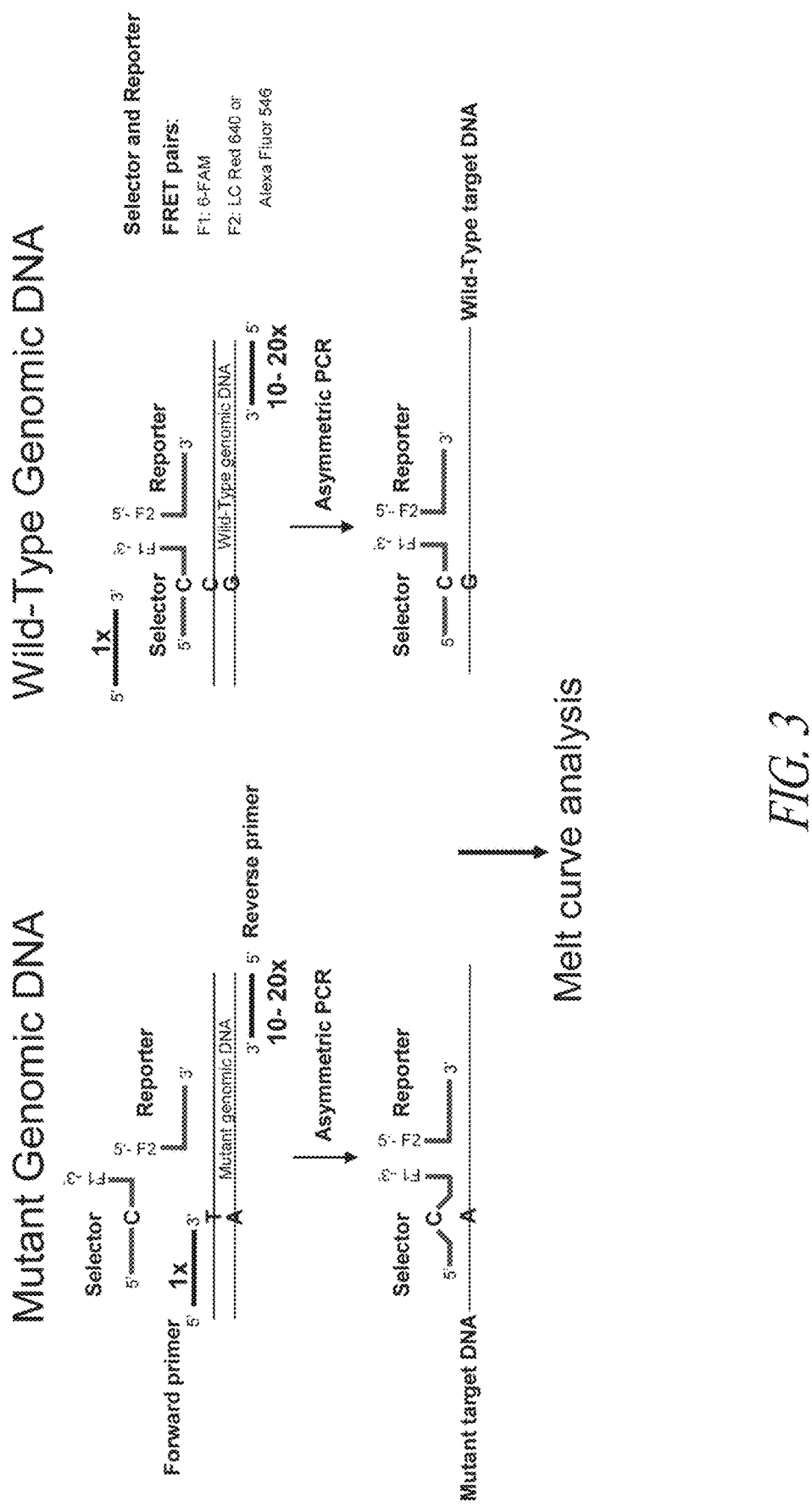
FIG. 3. Selector Assay design for EGFR T790M mutation detection.
Figure 4:
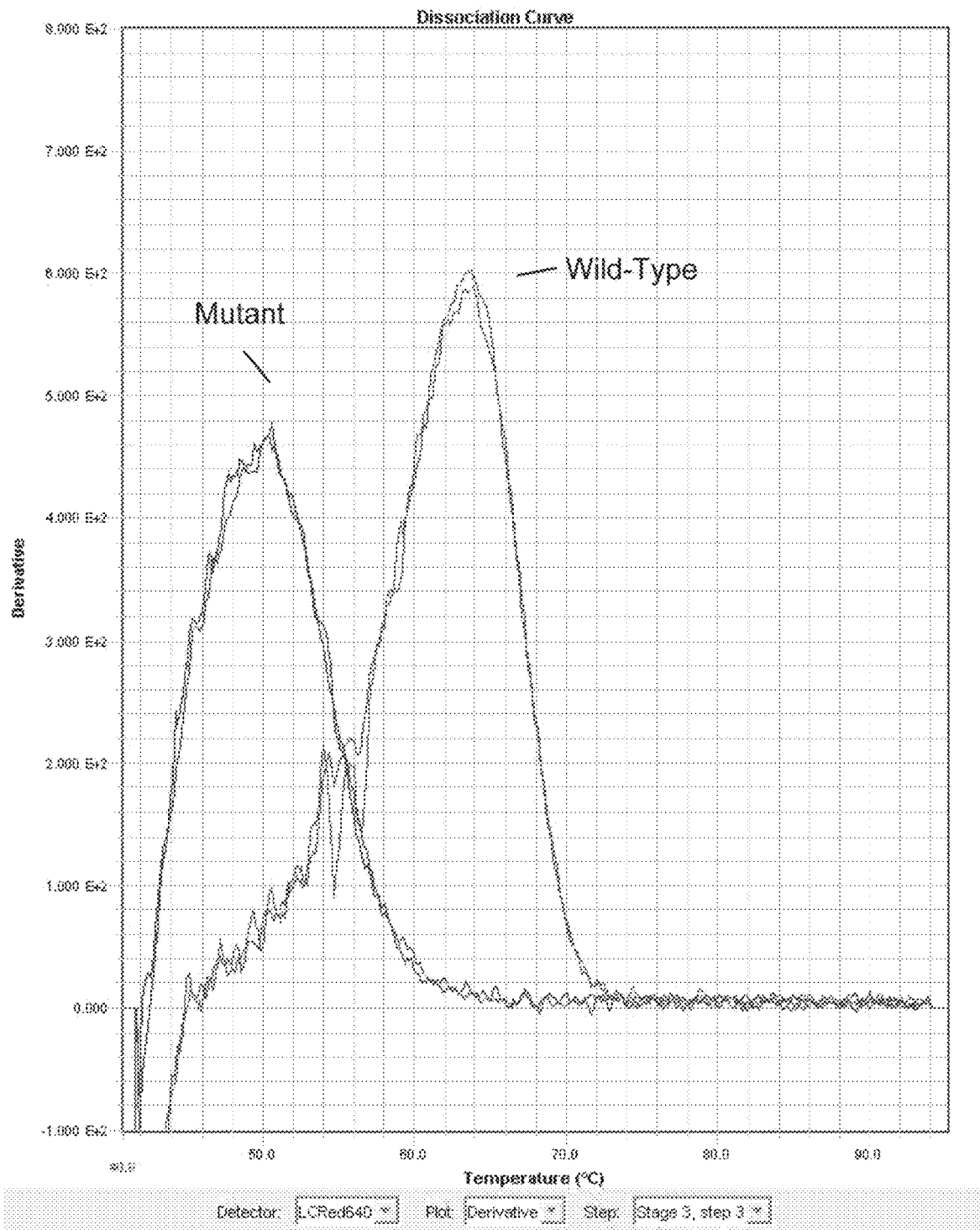
FIG. 4. The melting curve profile for synthetic mutant or wild-type target with Selector A and Reporter A shows that there is a significant reduction (about 13° C.) in the melting temperature for the mutant synthetic target.
Figure 5A:
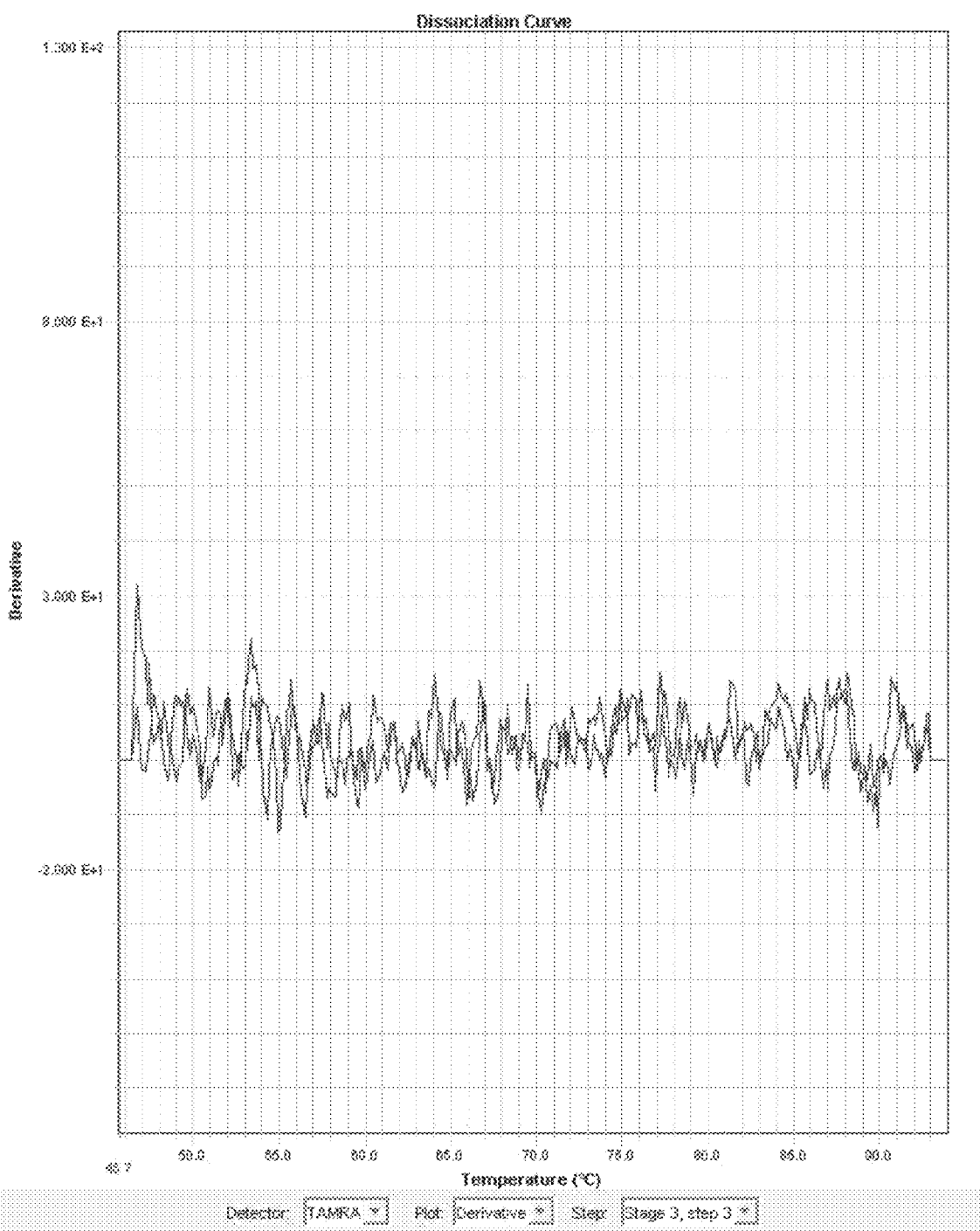
FIGS. 5A-5C. Selector Assay with AmpliTaq® DNA Polymerase, Stoffel fragment.
Figure 5B:
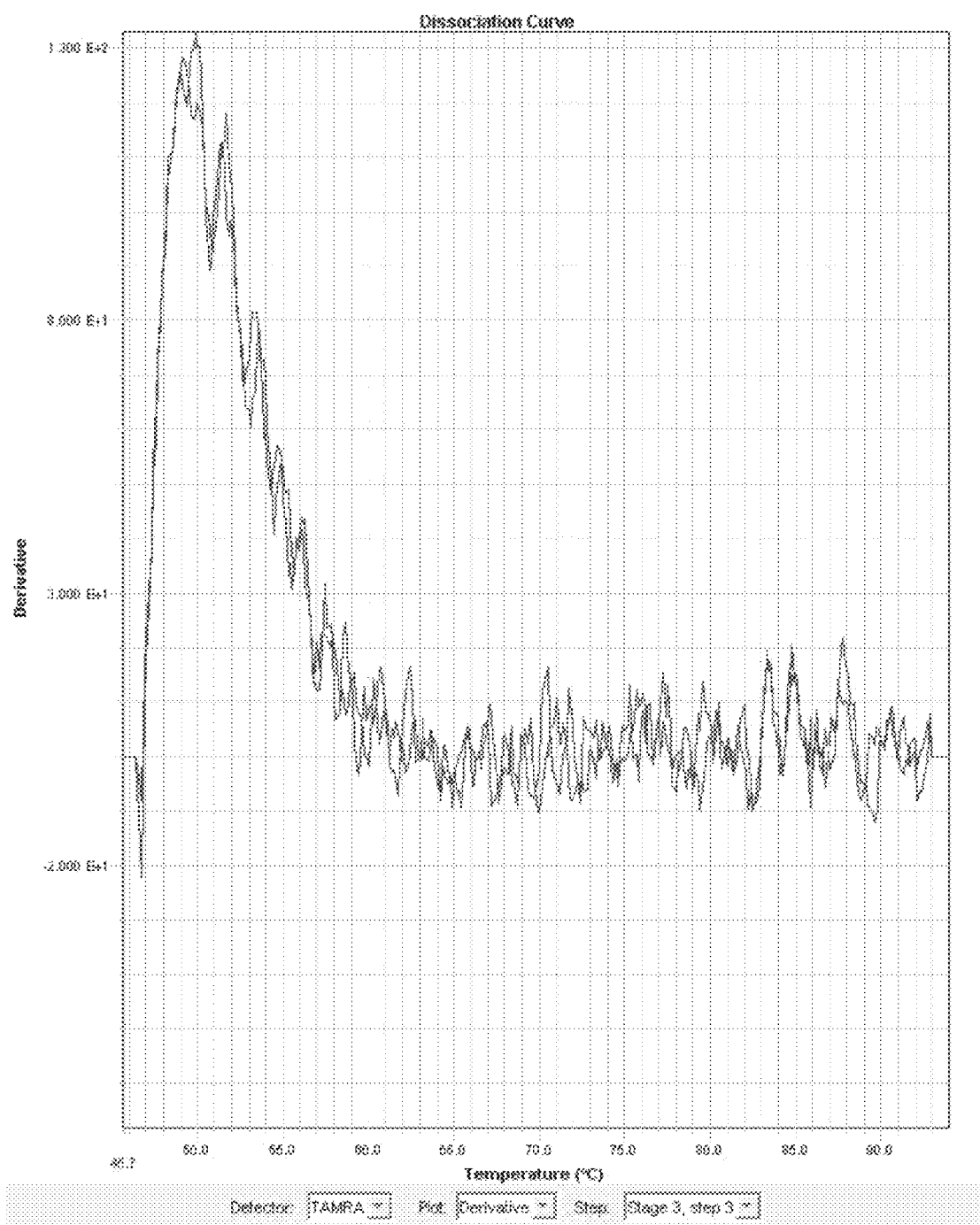
Figure 5C:
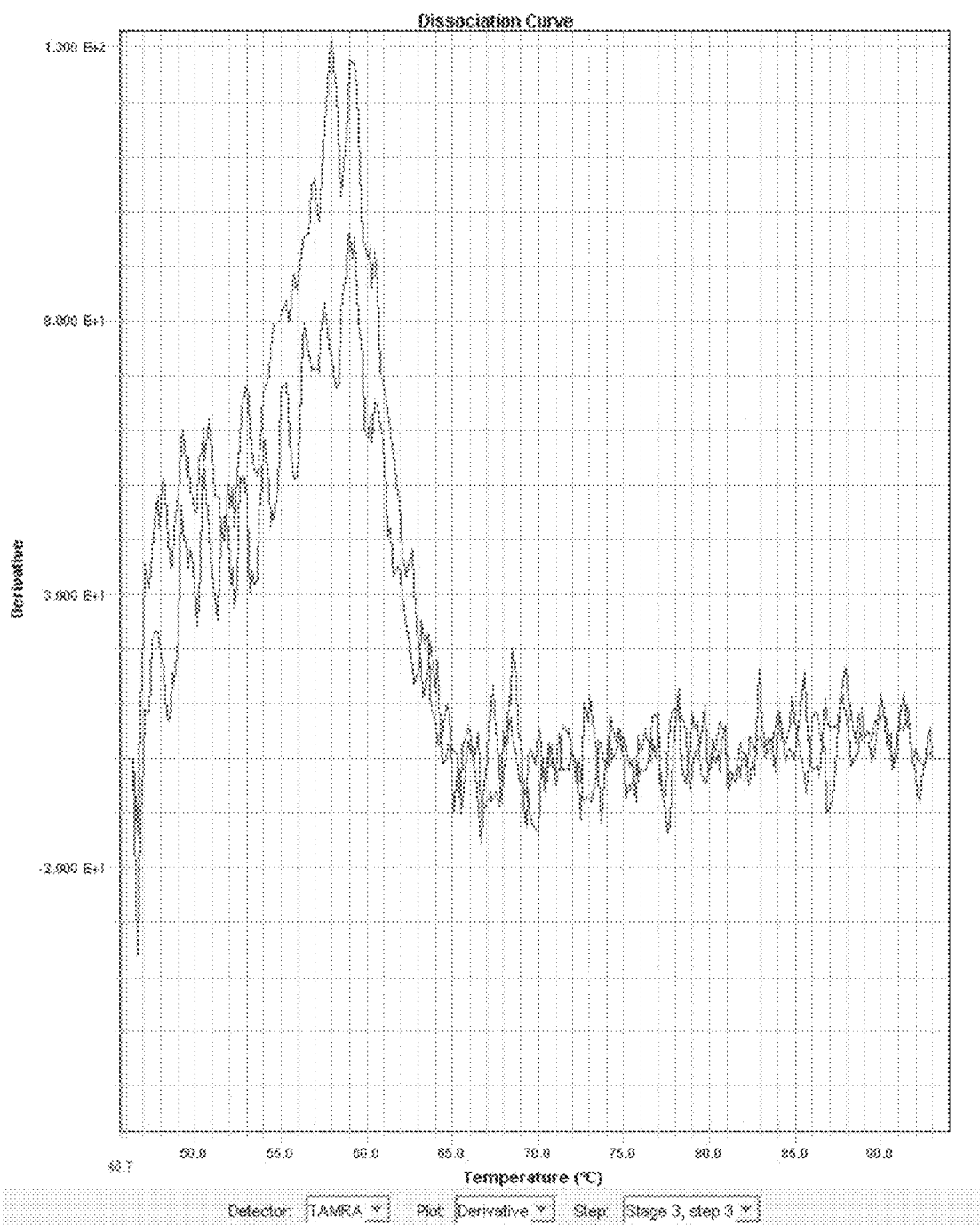
Figure 6A:
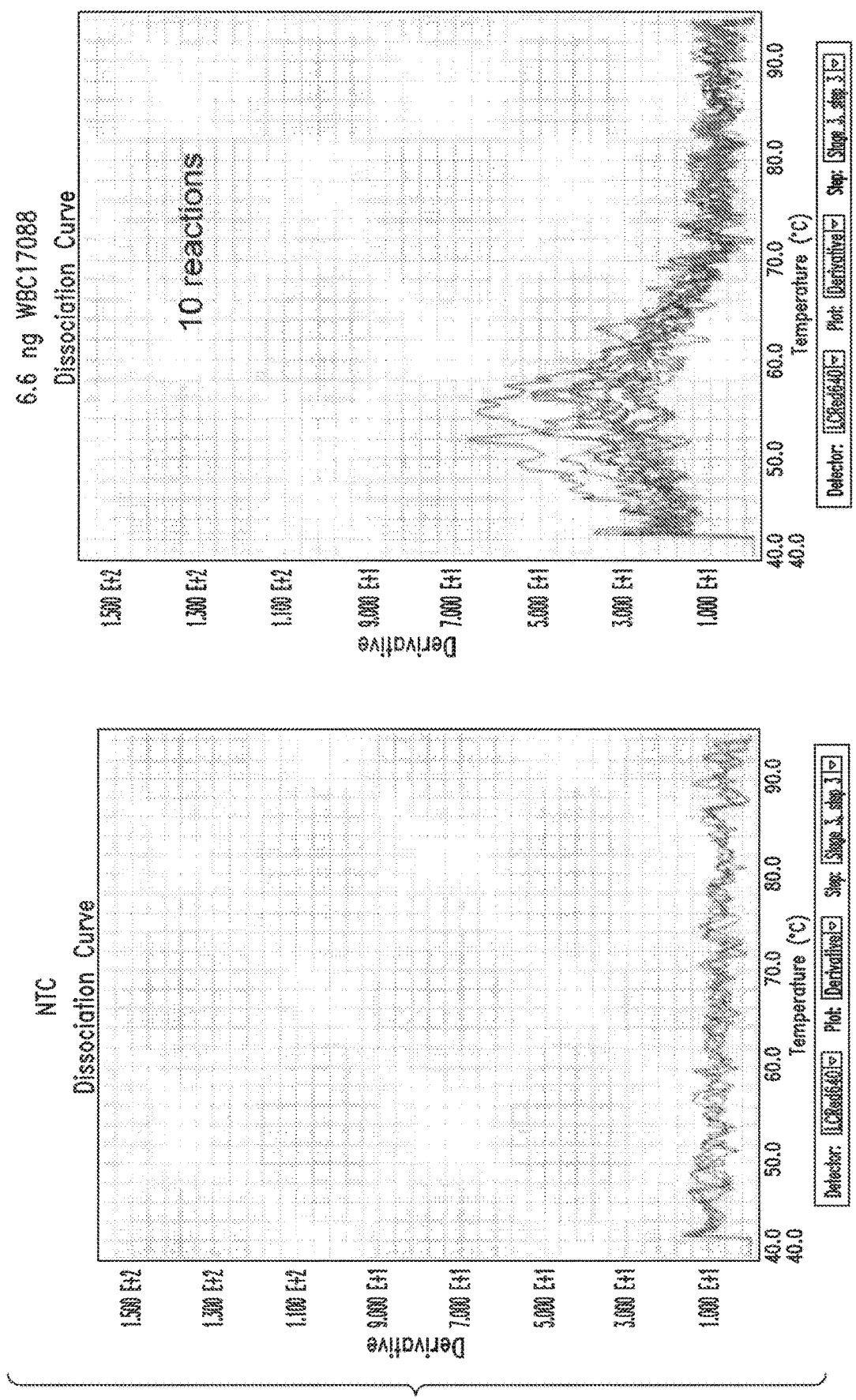
FIGS. 6A-6C. Selector Assay with Kapa HS DNA polymerase.
Figure 6B:
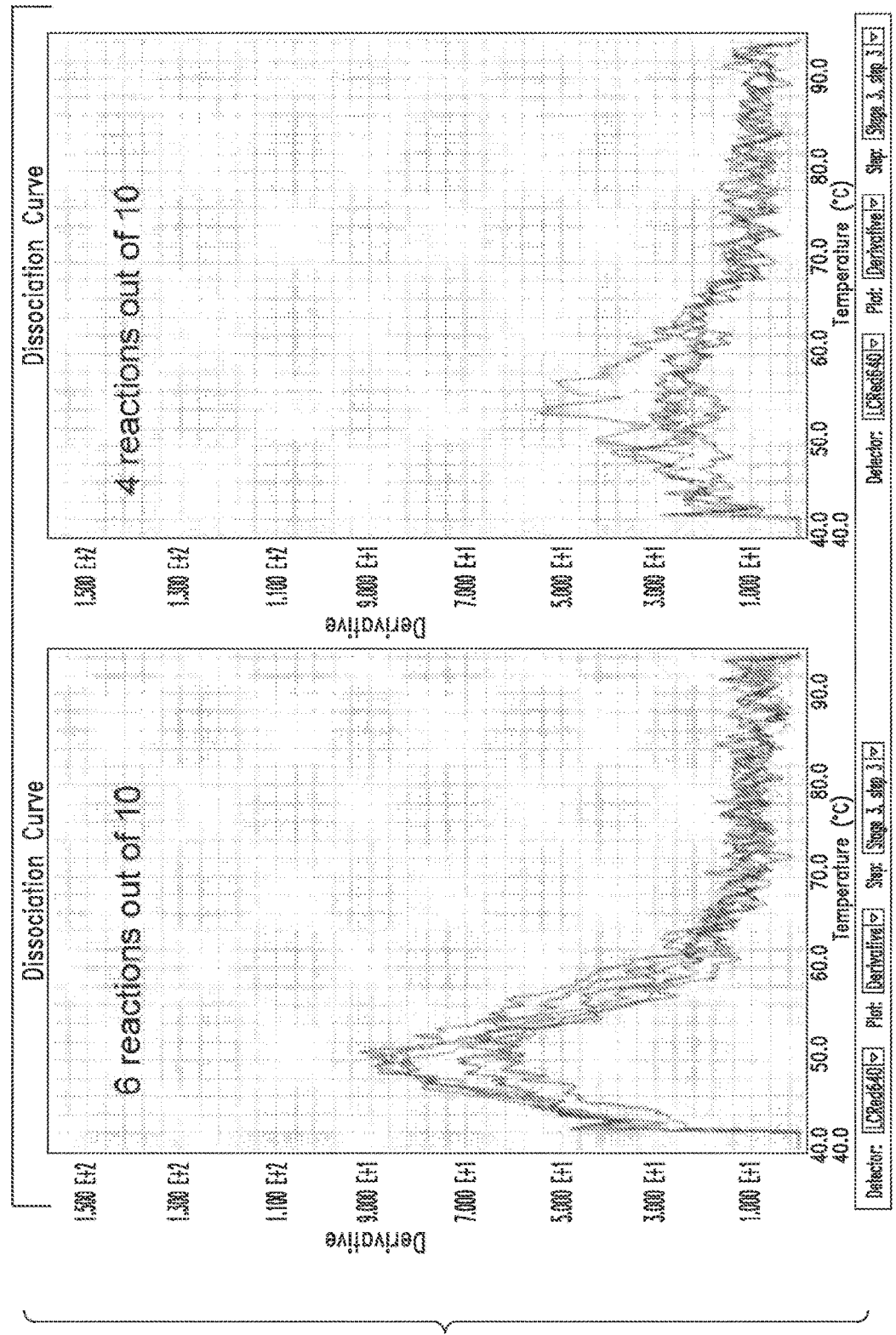
Figure 6C:
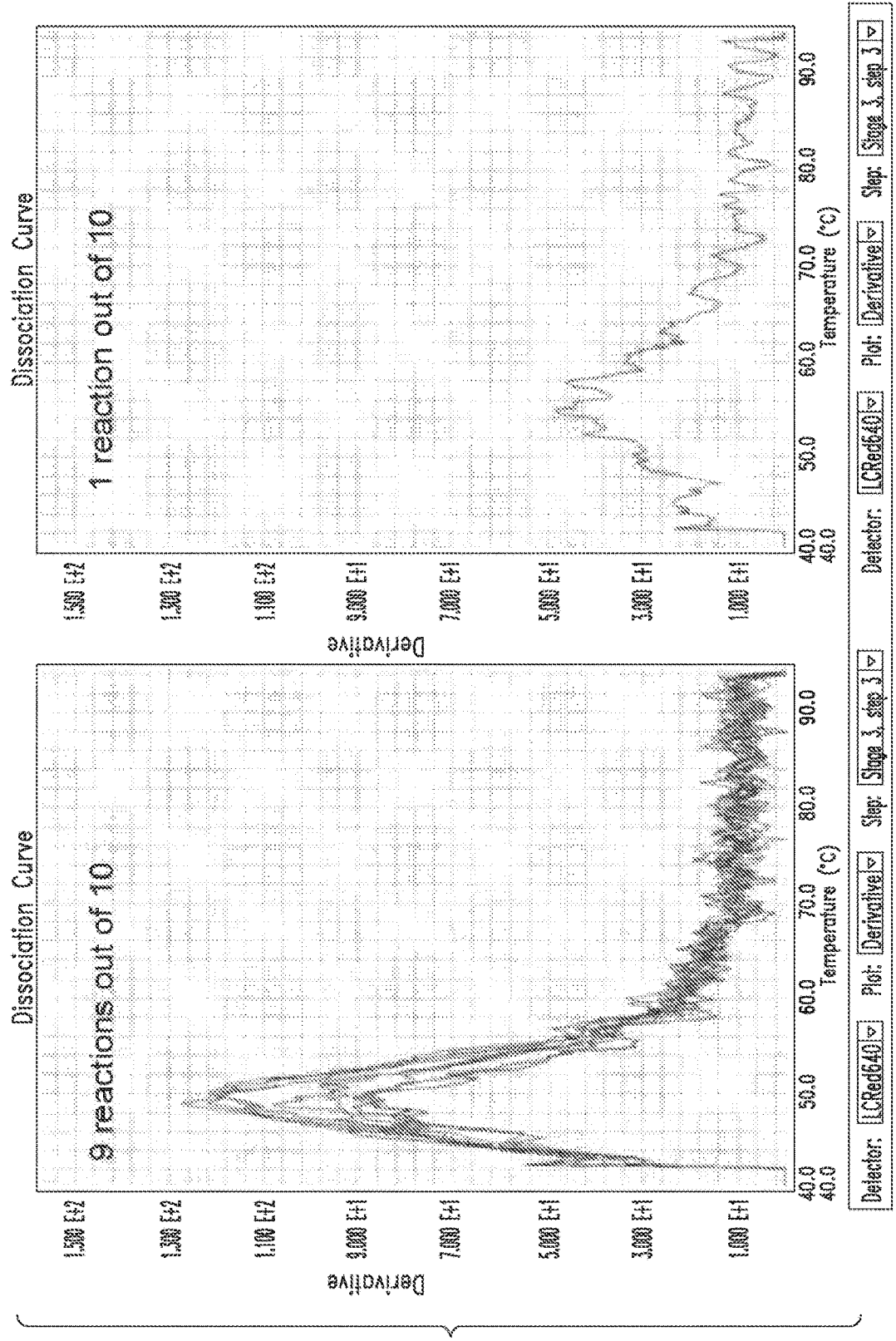
Figure 7:
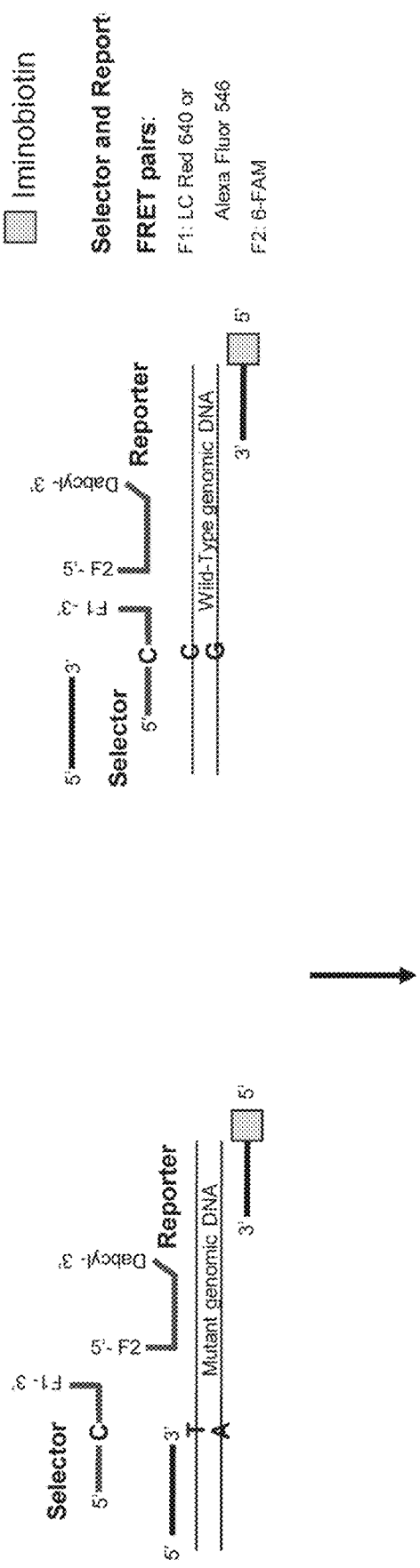
FIG. 7. Selector Plus Assay for EGFR T790M mutation detection. The Selector Plus assay is comprised of three steps which are designed to identify the presence of a mutant template in an excess of wild-type background: 1) Real-Time detection of the accumulating PCR product; 2) Melt curve analysis; and 3) Sequencing.

One mode of the Selector Assay uses asymmetric PCR (with 10 to 20-fold excess of reverse primer) and end-point melt curve analysis detection of the reverse strand by Förster Resonance Energy Transfer (FRET). The FRET pairs are Selector and Reporter oligonucleotides which are linked to 6-FAM and LC Red 640 or Alexa Fluor 546 fluorophores respectively. The Selector oligonucleotide used here is a 15-mer (with 2'-Fluoro ribonucleoside substitutions to increase its Tm). The Selector is complimentary to the wild-type sequence and serves as a blocker for wild-type amplification. In addition, there is a six nucleotide overlap between the forward primer and Selector. The Selector concentration was typically used at a 4-fold higher level to outcompete the forward primer from binding to the wild-type template. Because of the central location of the wild-type specific nucleotide and its increased affinity the Selector shows a significant Tm difference between mutant and wild-type template. In the case of Selector A this difference is about 13° C. (see also FIG. 2). The Reporter was designed to have a Tm of about 10° C. higher than the Selector, so that it is bound to the target at temperatures when the Selector starts dissociating. This difference in melting temperature makes it possible to distinguish between mutant and wild-type template through melt curve analysis.

Example 2. Detection of Wild-Type and Mutant Synthetic Targets with Selector and Reporter Oligonucleotide Probes Under Kapa HiFi Reaction Conditions A 10 µl reaction volume with 1×HiFi buffer, 0.4 µM Selector A (6-FAM labeled), 0.4 µM Reporter A (LC Red 640 labeled), with either 0.4 µM synthetic mutant or wild-type target were combined. The mixture was heated to 95° C. for 5 min, followed by 2 cycles of 98° C. for 30 sec and 57° C. for 30 sec. A dissociation curve analysis was then performed (95° C. for 1 min, 45° C. for 30 sec then with 1% ramp to 95° C.). The LC Red 640 FRET signal was detected in the custom set up LC Red 640 channel.

Example 3. Selector Assay Using PCR with AmpliTaq® DNA Polymerase, Stoffel Fragment (Life Technologies)

The reaction was carried out in a 10 µl reaction volume with 1× Stoffel buffer (10 mM KCl, 10 mM Tris-HCl, pH 8.3), 4 mM MgCl$_2$, 0.3 mM Cleanamp dNTP's (TriLink Biotechnologies), 0.1 µM Forward primer, 1 µM Reverse primer, 0.4 µM Selector A (6-FAM labeled), 0.4 µM Reporter B (Alexa Fluor 546 labeled), 2 U Stoffel fragment and the indicated amounts of genomic DNA. The PCR reactions were loaded on a 384-well plate. PCR cycling was done in the ABI 7900HT instrument with the following cycling conditions: 94° C. for 3 min, 55 cycles of 94° C. for 30 sec and 60° C. for 30 sec followed by a dissociation curve analysis (94° C. for 1 min, 45° C. for 30 sec then with 1% ramp to 94° C.). The Alexa Fluor 546 FRET signal was detected in the TAMRA channel. The PCR reactions were run on the ABI 7900HT instrument. The dissociation curve analysis at the end of the run shows that there is a difference of about 7° C. between Mutant and Wild-Type products.

Example 4. Selector Assay of Mutant T790M Detection in a Complex Background Using a High-Fidelity Kapa HS DNA Polymerase PCR with KAPA HiFi Hot Start DNA Polymerase (Kapa Biosystems) was done in a 10 µl reaction volume with 1×HiFi buffer (which contains 2 mM MgCl$_2$, and other components), 0.3 mM dNTP's, 0.1 µM Forward primer, 2 µM Reverse primer, 0.4 µM Selector A (6-FAM labeled), 0.4 µM Reporter A (LC Red 640 labeled), 0.4 U KAPA HiFi Hot Start DNA Polymerase and the indicated amounts of genomic DNA. The PCR reactions were loaded in a 384-well plate. PCR cycling was done in the ABI 7900HT instrument with the following cycling conditions: 95° C. for 5 min, 55 cycles of 98° C. for 30 sec and 57° C. for 30 sec followed by a dissociation curve analysis (95° C. for 1 min, 45° C. for 30 sec then with 1% ramp to 95° C.). The LC Red 640 FRET signal was detected in the custom set up LC Red 640 channel. 14 pg and 28 pg of mutant DNA were detected in a background of 6.6 ng of wild-type DNA. The higher amount of mutant DNA (28 pg) gave results with 9 out of 10 reactions showing a mutant peak, and 1 reaction showing a lower peak at the melting temperature of the wild-type. For the 14 pg of mutant with 6.6 ng of wild-type 6 out of 10 reactions showed a mutant peak and the rest of the reactions showed lower peaks with melting temperatures closer to the wild-type.

Example 5. The Selector Plus Assay for the T790M Mutation

This assay uses a blocker for wild-type amplification (as is the case in the Selector assay), but for the Selector Plus assay the blocker contains either a LC Red 640 or Alexa Fluor 546 fluorophore at the 3' end (it serves again as FRET pair for melt curve analysis, see below). In addition, the Reporter is dual labeled probe which allows Real-Time detection of the accumulating PCR product during the annealing/extension step. The Reporter is labeled with a 6-FAM label at or close to the 5'end and with a Dabcyl quencher at the 3' end. The design of the Reporter is such that under annealing/extension conditions (56-60° C.) the stem structure of the Reporter creates a loop which brings the 6-FAM in close proximity to the Dabcyl quencher to create very low background in the absence of target. In the presence of amplicon the Reporter binds opening the stem-loop structure. The amount of increasing 6-FAM fluorescence correlates with the amount of amplicon present. Real-time detection is used to identify the presence of T790M mutant molecules in the sample containing a large excess of wild-type molecules. This is done by correlating Cq values with Cq values for known quantities of the T790M mutant and wild-type. When real-time Cq values indicate the presence of a mismatch they are verified for the presence of the mismatch. This is done by selectively capturing one of the two strands using iminobiotin and carrying out melt curve analysis and sequencing (see FIG. 8).

Iminobiotin has a pH-dependent binding constant for avidin. At pH 10 it is bound and at pH 4 it can be eluted from avidin resin.

The Iminobiotin containing strand is captured using magnetic avidin beads (Spherotech, Inc.). The non-iminobiotinylated strand is separated from the iminobiotinylated strand by a combination of heat, low salt and denaturants. The isolated iminobiotinylated strand is eluted from the magnetic avidin beads at pH 4. Melt curve analysis is then performed by combining the isolated iminobiotinylated strand, Selector and Reporter (which serve as a FRET pair) and running a dissociation curve (as described in Example 4). Detection is done in the LC Red 640 or Alexa Fluor 546 channel. Sequencing reactions are performed by using the iminobiotinylated strand and/or the non-iminobiotinylated strand with the BigDye® Terminator v1.1 Cycle Sequencing Kit according to manufacturer instructions. Sequencing reactions are run on the ABI3730 DNA Analyzer for analysis.

TABLE 1

Oligonucleotides used for Selector Assay:

| Name | Sequence |
| --- | --- |
| Forward | 5'-A*C*CGTGCARCTCA*T*C*A-3' (SEQ ID NO: 1) |
| Reverse | 5'-G*C*AGGTACTGGGA *G*C*C-3' (SEQ ID NO: 2) |
| Selector A | 5'-2'OMe(U*C)*aucacgcagcu*c*a*(6-FAM)-3' (SEQ ID NO: 3) |
| Reporter A | 5'-(LC Red 640)(C3 Spacer)(C3 Spacer) *T*GCCCTTCGGCTGCCTC*C*T*(C3 Spacer)-3' (SEQ ID NO: 4) |
| Reporter B | 5'-2'OMe(U*G)*CC(C7 Spacer) (Alexa Fluor 546) CTTCGGCTGCCTC*C*T* (C3 Spacer)-3' (SEQ ID NO: 5) |
| Synthetic target WT | GCTCATCACGCAGCTCATGCCCTTCGGCTGCCTCCTGG (SEQ ID NO: 6) |
| Synthetic target MUT | GCTCATCATGCAGCTCATGCCCTTCGGCTGCCTCCTGG (SEQ ID NO: 7) |

*Indicates phosphorothioate bond; lower case indicates 2'-Fluoro Ribonucleoside

TABLE 2

Oligonucleotides for Selector Plus Assay:

| Name | Sequence |
| --- | --- |
| Selector 1 | 5'-2'OMe(U*C)*aucacgcagcu*c*a* (LC Red 640)-3' (SEQ ID NO: 34) |
| Selector 2 | 5'-2'OMe(U*C)*aucacgcagcu*c*a* (Alexa Fluor 546)-3' (SEQ ID NO: 35) |
| Reporter 1 | 5'-u*g*ccc(C7 Spacer) (6-FAM) TTCGGCTGCCTCCTGGAGCCG*A*A* (C3 Spacer) (Dabcyl)-3' (SEQ ID NO: 8) |
| Reporter 2 | 5'-(6-FAM)-(C3 Spacer) *T*TCGGCTGCCTCCTGGACTATGTCCGGAG CCG*A*A*(C3 Spacer) (Dabcyl)-3' (SEQ ID NO: 9) |

*Indicates phosphorothioate bond; lower case indicates 2'-Fluoro Ribonucleoside

Figure 9:
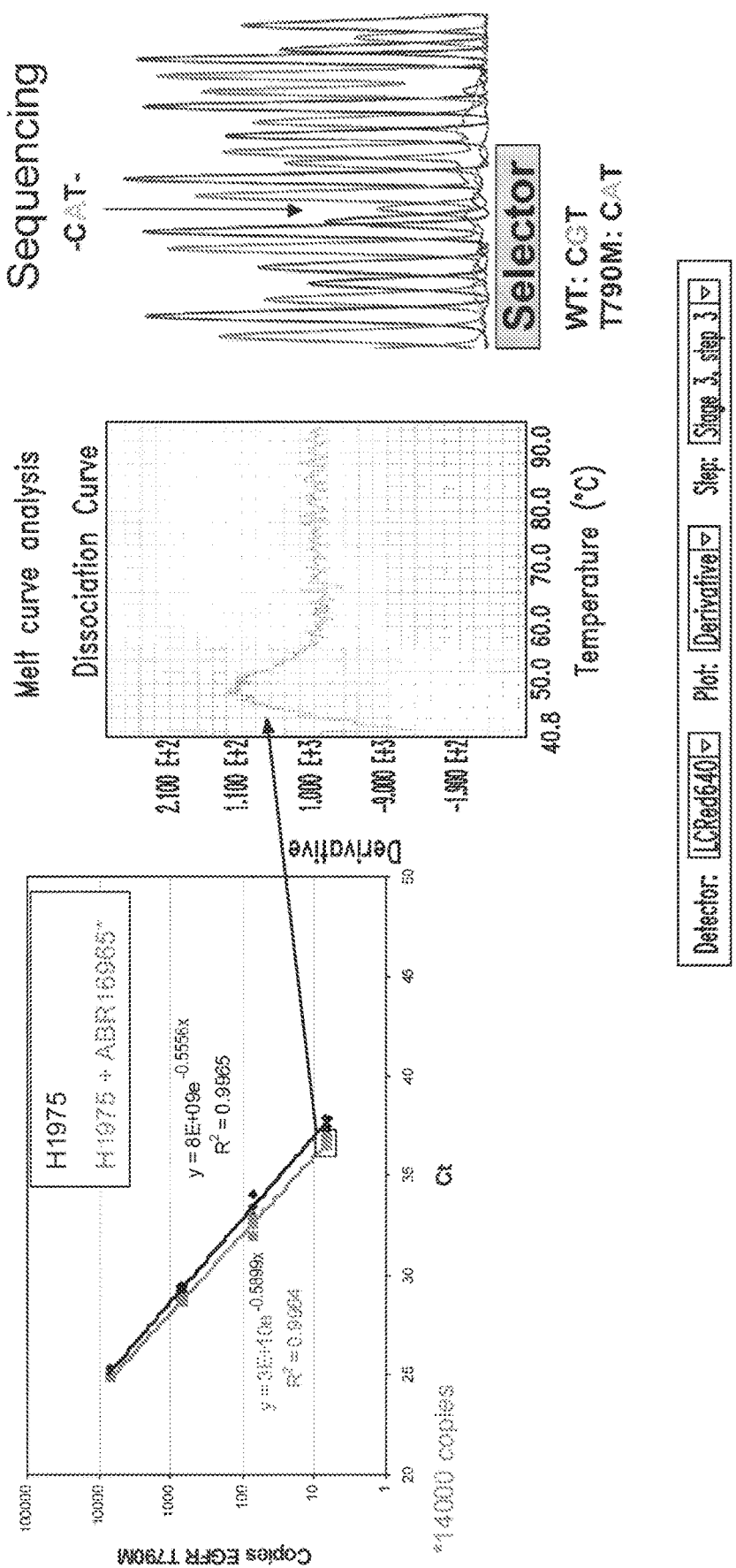
FIG. 9. The Selector Assay is quantitative and the presence of excess wild-type template minimally affects T790M mutant amplification.

Example 6. Detection of Rare Mutants in a Complex Wild-Type Genomics Background Using the Selector Assay Increasing amounts of H1975 genomic DNA (0.05 ng, 0.5 ng, 5 ng or 50 ng, which corresponds to 7, 70, 700 and 7000 copies T790M respectively) were used in the Selector Assay (all reactions with Selector) in the presence or absence of 50 ng ABR16965 genomic DNA (about 14000 copies of wild-type control). See FIG. 9. The amplification data were plotted and are shown in the graph (left panel). The melt curve analysis and sequencing data of the Selector Assay reaction of a mixture of 50 pg H1975 with 50 ng ABR16965 are shown (1:2000 mixture of mutant to wild-type copies). The nucleotide specific for the T790M mutation (A) is shown by an arrow above the sequence peak and the region bound by the Selector is indicated by a box.

Results:

Increasing amounts of H1975 genomic DNA (from 7 up to about 7000 copies) were used in the Selector Assay in the presence of Selector and about 14000 copies ABR16965genomic DNA (wild-type control). As can be seen from the amplification data graphs, the presence of the wild-type control DNA minimally affects the amplification of the T790M mutant (compare H1975 to H1975+ABR16965 graph). It is evident that the Selector™ Assay shows linear regression over the tested concentrations indicating that the assay is quantitative over the tested range. Also, the melt curve analysis—which shows the mutant melt curve peak—and sequencing results indicate that the T790M mutation can be detected when 50 pg H1975 (7 copies T790M) are mixed with 50 ng of ABR16965 (14000 copies of EGFR). The T790M mutant can also be detected with the higher amounts of H1975 when mixed with wild-type DNA (data not shown). Thus, the data here show that the Selector™ Assay was able to detect the mutant DNA when it was mixed with wild-type DNA at a ratio of as much as 1:2000.

Methods:

Selector Assay reactions were done in a 10 µl volume with the following components: 0.2 µM forward primer (5'-C*A*CCGTGCAR*C*T*C-3' (SEQ ID NO: 10); R=A/G; * indicates phosphorothioate), 2 µM reverse primer (5'-T*G*TGTTCCCGGACAT*A*G*T-3' (SEQ ID NO: 11); *indicates phosphorothioate), 0.3 µM Selector 6 (5'-2'OMe(a*u)*cacgcagcu*c*a* (LCRed640)-3' (SEQ ID NO: 12); *indicates phosphorothioate; lower case indicates 2'-Fluoro Ribonucleoside), 0.6 µM Reporter 4 (5'-u*g*ccc (C7-NH) (6-FAM)TTCGGCTGCcuccu GGAGCCG*A*A* (Dabcyl)-3' (SEQ ID NO: 13); *indicates phosphorothioate; lower case indicates 2'-Fluoro Ribonucleoside), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 1 min, 69° C. for 15 s, followed by a dissociation curve analysis (95° C. for 1 min, 40° C. for 30 s then with a 1% ramp to 95° C.). Detection of amplification product was done by monitoring 6-FAM and LCRed640 fluorescence during the 52° C. cycle step. For melt curve analysis the LCRed640 signal was monitored during the 40° C. to 95° C. transition.

For Sanger sequencing, the PCR products were purified with the QIAquick PCR Purification Kit (Qiagen) and sequencing reactions were done using the BigDye® Terminator v1.1 Cycle Sequencing Kit (LifeTechnologies, Cat. No. 4337449) according to manufacturer instructions with sequencing primer T790M seq6 (CATAGCAGCTGTTTTC-CCAGTCATCGACGTTGTAGTCCAGGAGGCAGC-CGAA (SEQ ID NO: 14)). Sequencing reactions were purified using Centri-Sep™ Columns (LifeTechnologies, Cat. No. 401762) and analyzed on the 3730 DNA Analyzer.

Figure 10:
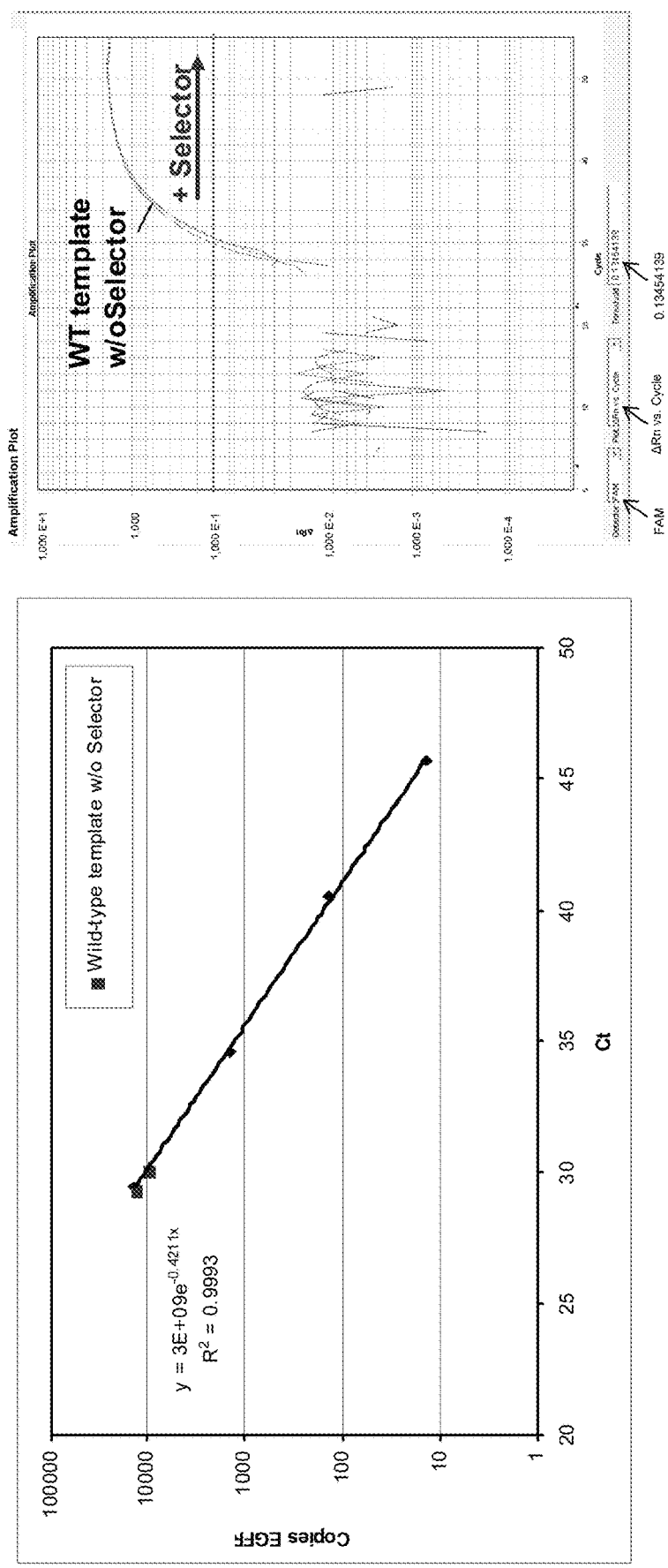
FIG. 10. Inhibition of wild-type amplification by Selector.

Example 7. Demonstration of Inhibition of Wild-Type Amplification Using the Selector Assay Selector Assay was done using a wild-type template from WGA material of a lung cancer blood sample. See FIG. 10. The amplification of wild-type template in the presence or absence of Selector is shown. The copies detected are plotted into a standard curve obtained by performing the Selector Assay with H1975 genomic DNA standards in the presence or absence of Selector (0.05 ng, 0.5 ng, 5 ng and 50 ng) (only the standard curve in reactions with Selector are shown).
Results:
WGA material from a lung cancer blood sample that was found negative for T790M was used to generate a wild-type template. To do this, the WGA material was pre-amplified for 15 cycles to generate a 228 bp PCR fragment containing the T790M mutation region which was then used for nested PCR in the Selector Assay. As can be seen from the amplification curve in FIG. 10, addition of Selector to the Selector Assay reaction blocks amplification of the wild-type template which is not detectable for up to 55 cycles. The number of wild-type copies was determined by a standard curve run on the same plate with H1975 genomic standards and was calculated as about 10800.
Methods:
The WGA material used in this experiment is from a lung cancer blood sample that was prepared using the CEE™ microchannel as described for FIGS. 13 and 14. The WGA material was pre-amplified with forward primer FP19 (A*C*CGTGCARCTCA*T*C*A (SEQ ID NO: 1); R=A/G; * indicates phosphorothioate) and reverse primer RP14 (G*C*ACGCACACACAT*A*T*C (SEQ ID NO: 33); * indicates phosphorothioate) under Selector Assay reaction conditions as described for FIG. 1, except that no Selector and Reporter was used, cycling was for done for 15 cycles and the melt curve analysis was omitted. The obtained material was diluted fifty-fold with 10 mM Tris-HCl pH 8.0, 0.1 mM EDTA and used in Selector Assay reactions in the presence or absence of Selector as described for FIG. 9.

Example 8. The Selector Assay with Nucleic Acid Isolated from Plasma of a Lung Cancer Patient Nucleic acid prepared from a lung cancer patient plasma sample was used in the T790M Selector Assay. The Selector Assay reactions were done in the presence or absence of Selector. The latter condition allows the amplification of wild-type sequences and serves as a control for the reaction conditions and presence of nucleic acid in the plasma preparation. The melt curve analysis of the Selector Assay PCR products is shown with the location of the mutant and wild-type melt curve peaks indicated. For the melt curve analysis of −Selector PCR reactions, Selector and Reporter were added post-amplification. The Selector Assay reaction products were sequenced to confirm the presence of mutant T790M (CAT) or wild-type sequences (CGT). The box labeled Selector below the sequence indicates location of Selector binding.
Results:
Nucleic acid was prepared from blood plasma of a lung cancer patient with the Selector Assay in the absence and presence of Selector. The Real-Time PCR results in the presence of Selector indicate, that mutant amplification as detected (see +Selector reactions in 6-FAM and LCRed640 channel). The amplification of mutant sequence was further confirmed by the melt curve analysis of the amplification product. The melt curve peak of the +Selector reaction showed a Tm of about 13° C. lower than the wild-type melt curve peak which is observed in the −Selector reaction. To confirm the presence of a mutation, the PCR product of the +Selector was sequenced and the mutation characteristic for T790M was identified. The sequencing of the −Selector PCR product lead to the identification of a wild-type sequence. Based on the standard curve (FIG. 11B) the number of T790M copies found in the 3 ml plasma was 577 and the number of EGFR copies found was 46348.
Methods:
Blood (about 8 ml) from a lung cancer patient (18299) was drawn into a CEE-Sure™ tube (Biocept, Inc.; containing anti-clumping reagent) and nucleic acid from the plasma portion was prepared within 48 hours of blood draw. To do this, the whole blood was spun for 5 minutes at 3000×g, RT, and the obtained plasma fraction respun 10 minutes at 16000×g, 4° C. About 3 ml of the plasma supernatant was used for nucleic acid preparation using the QIAamp Circulating Nucleic Acid Kit (Qiagen, Cat. No. 55114) according to manufacturer instructions with the following modifications: the Proteinase K digestion was done for 60 minutes at 60° C., addition of carrier RNA was omitted and the elution was done with 20 µl of the provided elution buffer.

One microliter of the nucleic acid preparation from plasma (total volume of about 17 µl) was used directly in a 10 µl T790M Selector Assay PCR reaction as described previously.

To determine the melt curve profile of the PCR product from Selector Assay reactions which were run in the absence of Selector (see above −Selector), Selector and Reporter were added post-amplification and the dissociation curve analysis was run under the same conditions as described before.

Figure 11A:
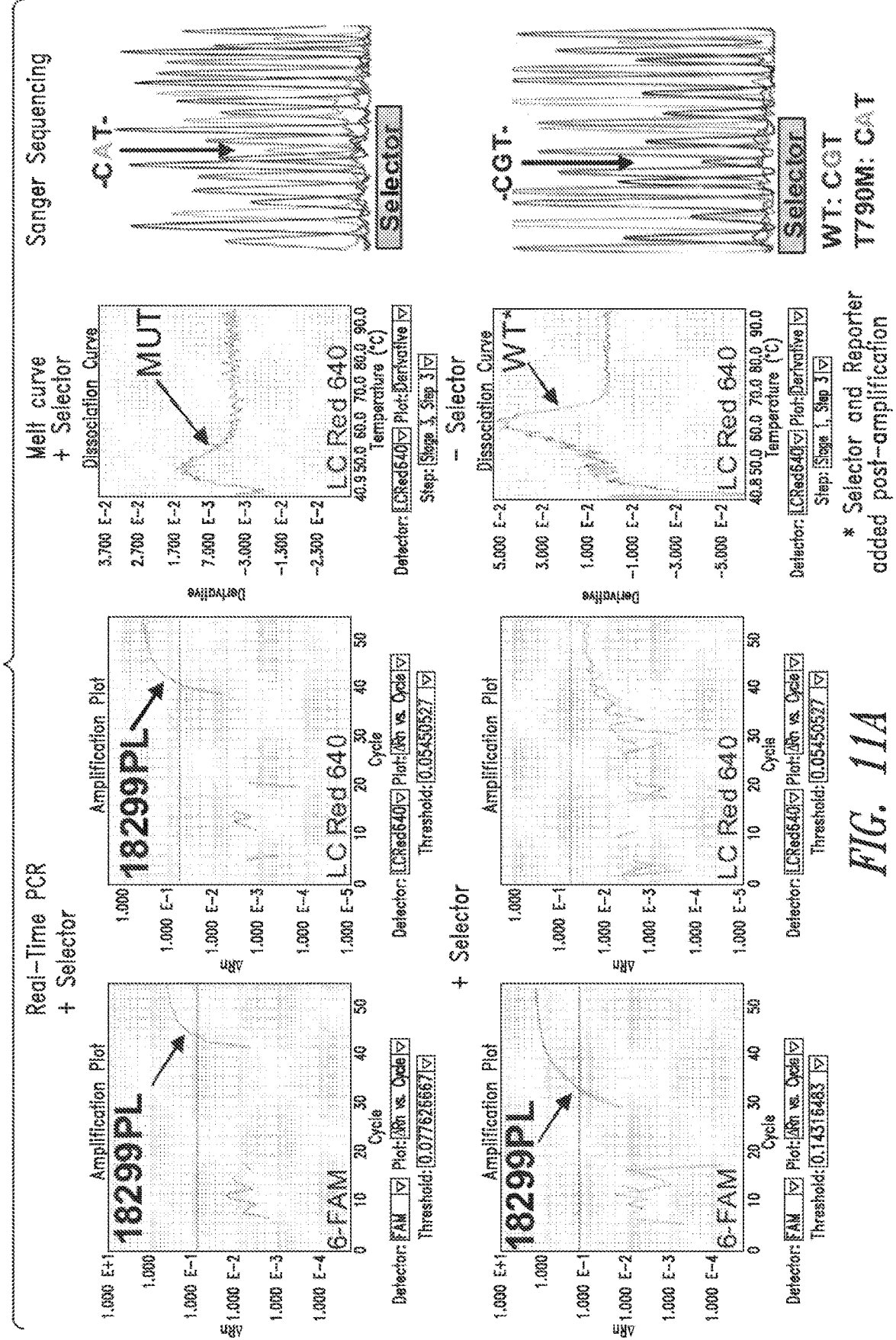
FIG. 11A: EGFR T790M identification in nucleic acid from clinical lung cancer plasma sample.
Figure 12:
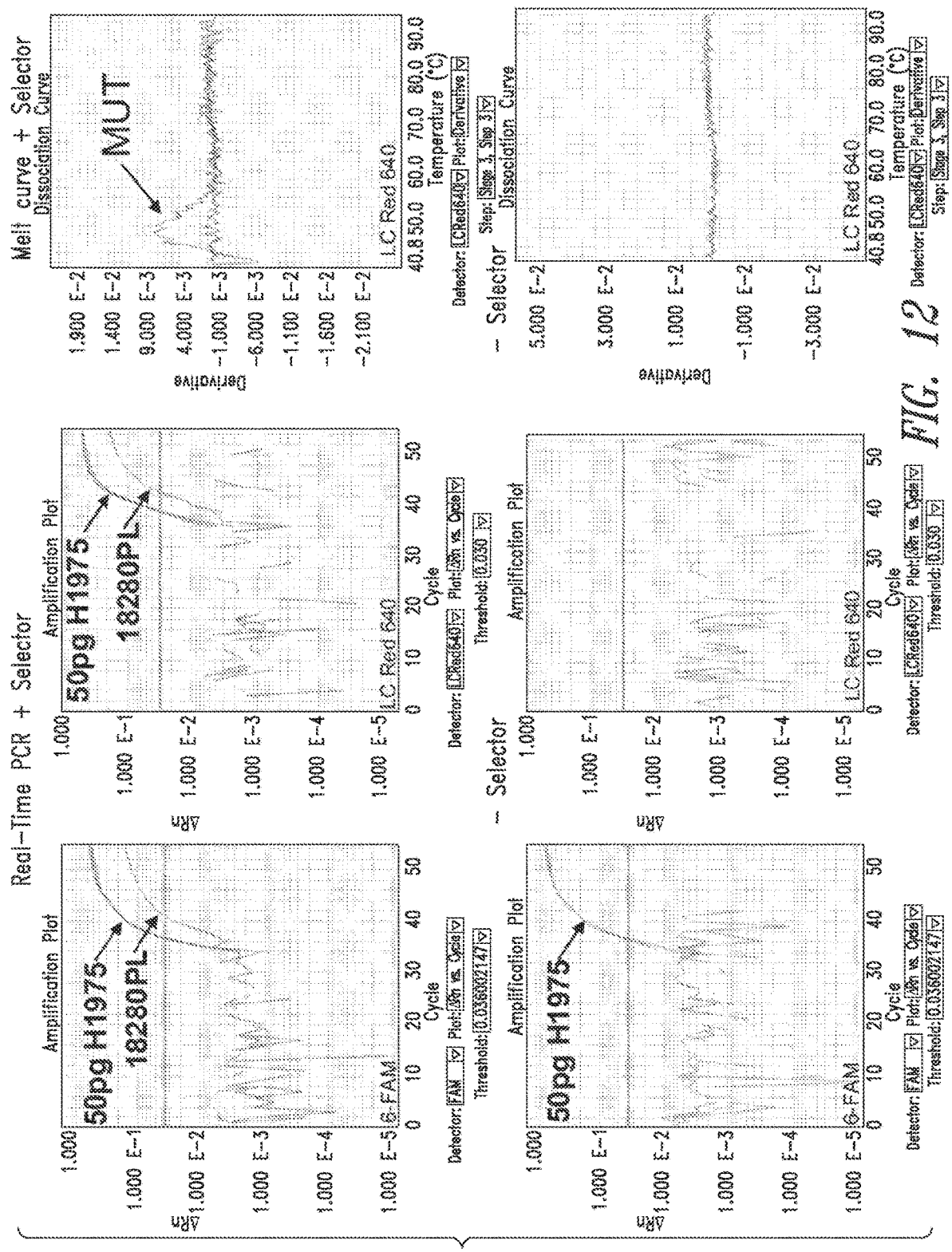
FIG. 12. Selector Assay with cDNA prepared from clinical lung cancer plasma samples.

The amplification data of the plasma nucleic acid reactions shown in FIG. 11A were plotted on a standard curve graph. The standard curve was obtained by performing the Selector™ Assay with increasing amounts of H1975 genomic DNA in the presence or absence of Selector. The reactions were run on the same plate as the plasma nucleic acid.

Example 9. Selector Assay for mRNA Derived from the Plasma of a Lung Cancer Patient cDNA prepared from a nucleic acid sample of a lung cancer patient (18280) was used in the Selector Assay run in the presence or absence of Selector as described previously (see Example 8). The reactions using the cDNA were run in duplicate. One of the reactions showed amplification in the presence of Selector. The amplification of 50 pg H1975 (about 7 copies of T790M in the presence of Selector) is shown on the same graph. The melt curve profile of the amplified product corresponds to a mutant and sequencing confirmed the presence of the T790M mutation in the amplified PCR product.
Methods:
cDNA was prepared from DNAse I-treated nucleic acid of a clinical lung cancer sample using the Superscript III First-Strand Synthesis System (LifeTechnologies Cat. No. 18080-051). Oligo(dT) provided by the kit was used and the synthesis performed according to the manufacturer's instructions.

Results:

We detected the presence of T790M mutant in the cDNA preparation from lung cancer plasma sample. About eight RNA copies of T790M were detected in the 3 ml plasma.

Example 10. Selector Assay of Cells Recovered from the Biocept CEE™ Microchannel The amplification data of a spike and recovery experiment with H1975 in whole blood is shown. See FIG. 13A. The data were plotted in standard curve graphs obtained from reactions with increasing amounts of H1975 genomic DNA control (upper panel). Reactions in the presence of Selector allow the quantification of spiked H1975 cells (Spike A, Spike B and Spike C in increasing number) whereas reactions in the absence of Selector allow the quantification of background cells (WBC's) found in the microchannel eluate.

Figure 13A:
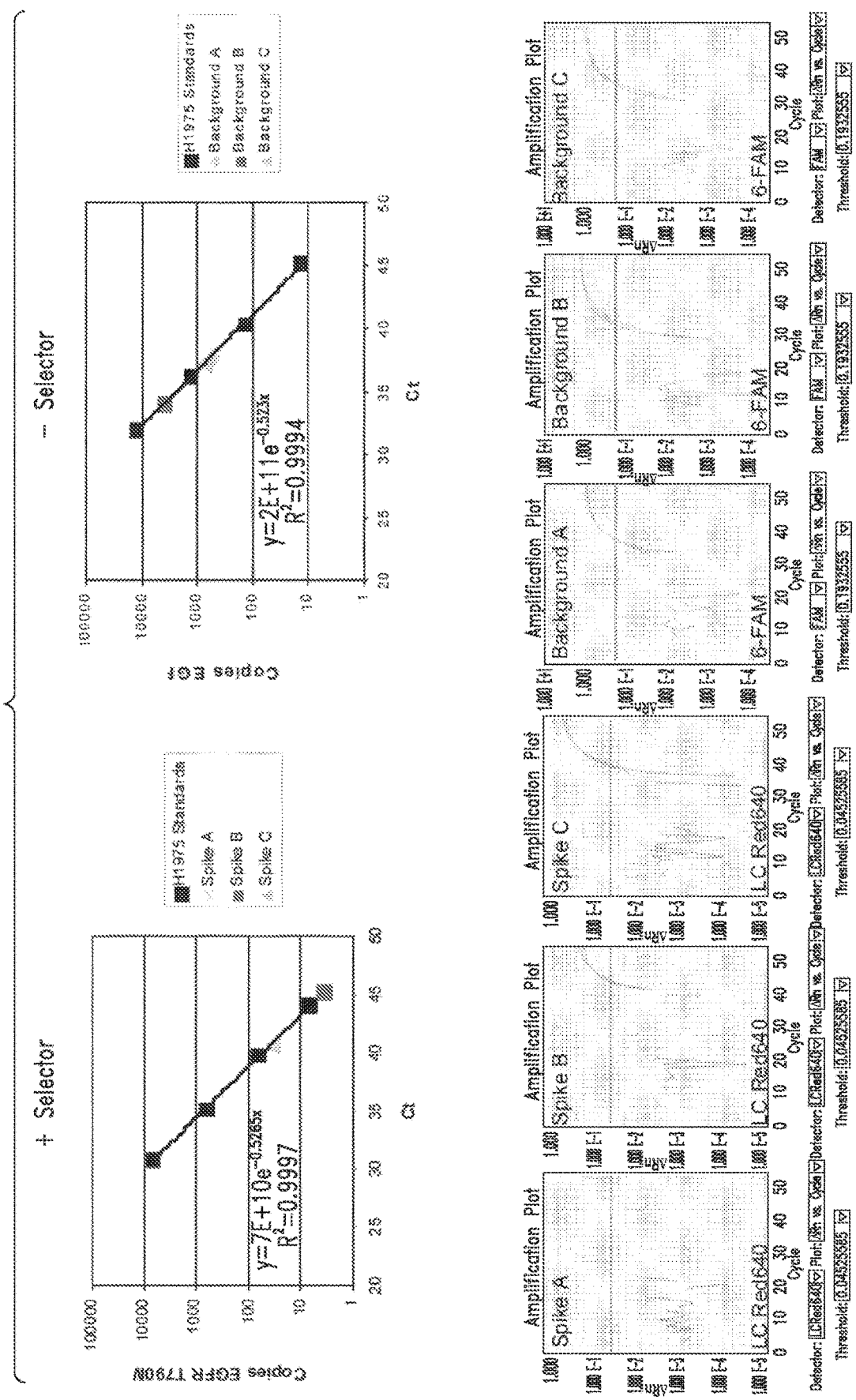
FIG. 13A: Selector Assay with material pushed off Biocept's CEE™ microchannel after spike and recovery of H1975 cells in whole blood.
Figure 13B:
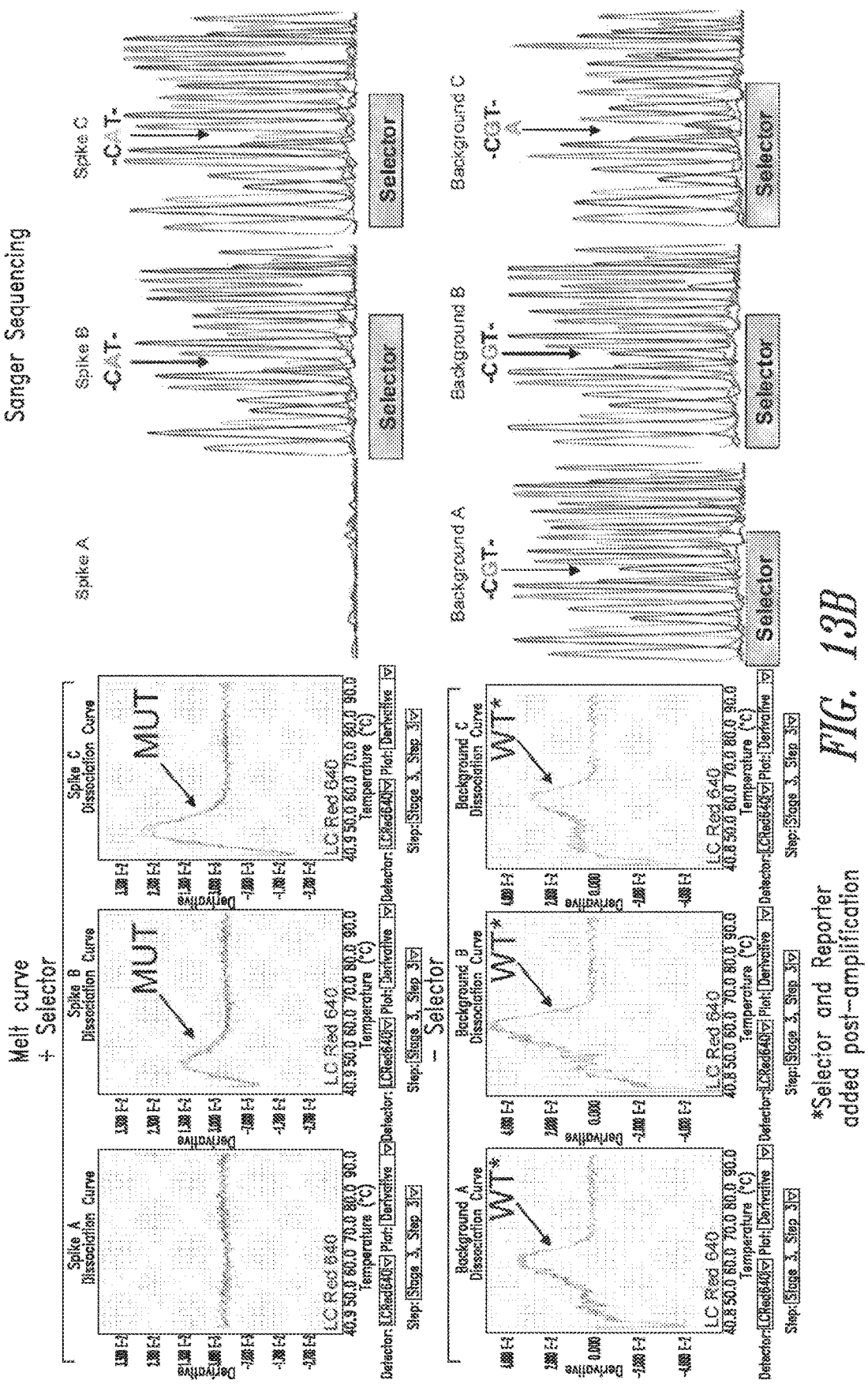
FIG. 13B: Melt curve analysis and Sanger sequencing of the Spike and Recovery Selector Assay reactions shown in FIG. 13A.

The amplification products from FIG. 13A were analysed by melt curve analysis. See FIG. 13B. For the melt curve analysis of −Selector PCR reactions, Selector and Reporter were added post-amplification. The location of mutant and wild-type melt curve peaks is indicated. The samples were used in Sanger sequencing reactions to confirm the presence of mutant or wild-type sequences. The location of Selector binding is shown below the sequence.

Methods:

Increasing numbers of H1975 cells were spiked into whole blood in CEE-Sure™ tubes. Buffy coats were prepared and incubated with a cocktail of biotinylated antibodies that specifically recognize markers on the surface of the cancer cells including EpCAM. Buffy coats were then run through a streptavidin coated-microchannel (CEE™ microchannel, Biocept, Inc.). Captured H1975 cells were visualized and enumerated by means of cytokeratin staining and subsequently eluted from the channel. Following digestion with a protease and inactivation of the enzyme, 1 µl was used in the Selector assay (as described in Example 9).

Results:

Spiked H1975 cells were recovered from whole blood using Biocept's CEE™ microchannel. Spike A, Spike B and Spike C contained 0, 3 and 16 cells per µl microchannel eluate respectively (as judged by CK+ staining of the microchannel before and after elution). After elution and protease digestion, the genomic DNA material was used in the Selector Assay in the presence or absence of Selector. Based on the standard curves the number of detected H1975 cells in Spike A, Spike B and Spike C is 0, 3 and 36 respectively per µl microchannel eluate. The Selector™ Assay results therefore match closely the microchannel results.

Figure 14A:
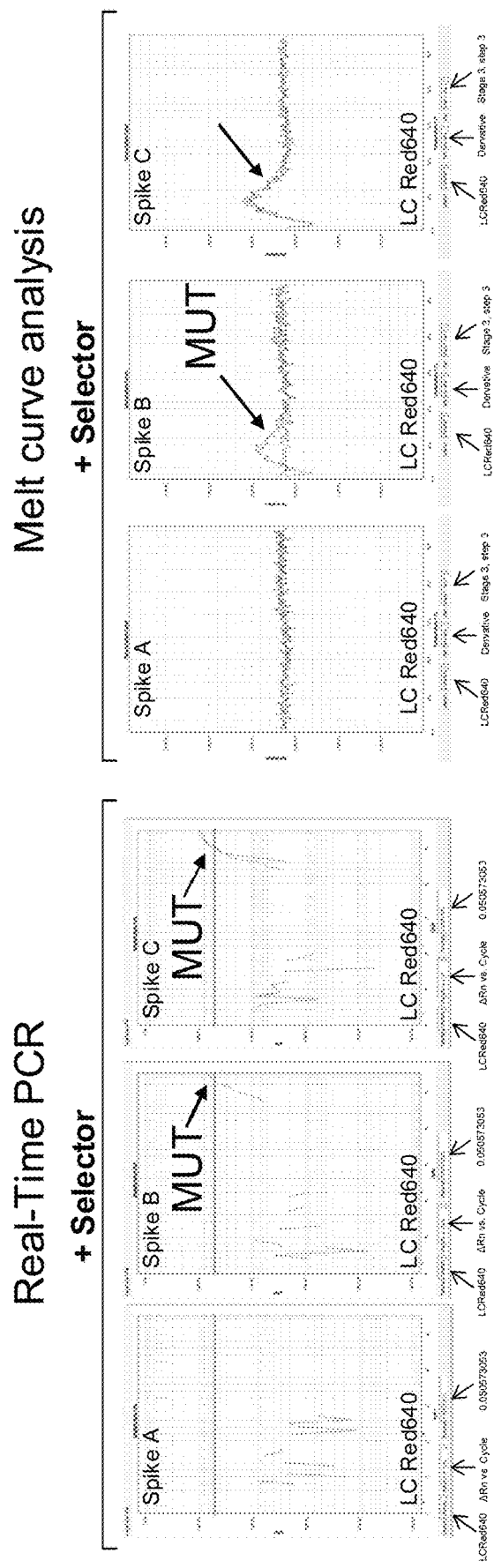
FIG. 14A: Selector Assay with whole genome amplified (WGA) material from a spike and recovery experiment of H1975 in whole blood.
Figure 14B:
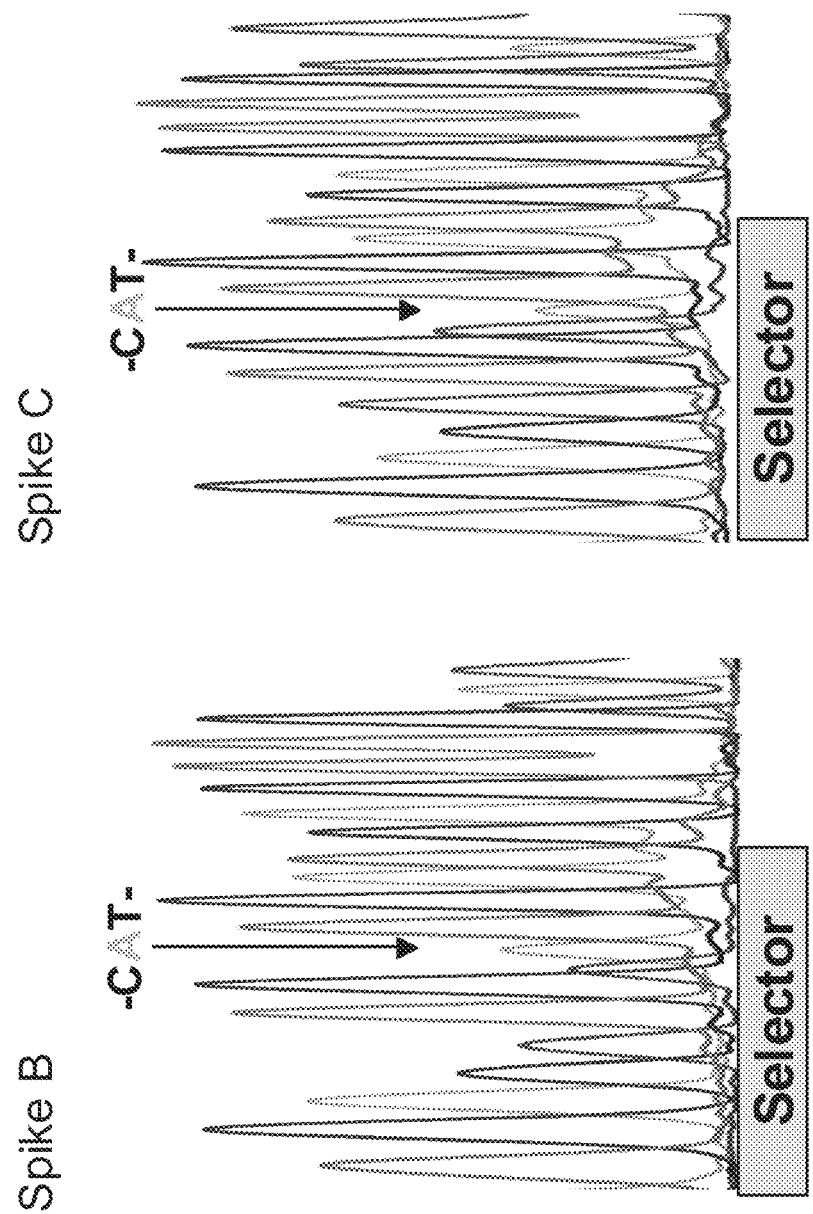
FIG. 14B: Sequencing of Selector Assay reactions with the WGA material.

Example 11. Selector Assay of Cells Recovered from the Biocept CEE™ Microchannel and Amplified Using WGA The same spike and recovery reactions that were analyzed in Example 9, were whole genome amplified and used in the Selector Assay reactions in the presence of Selector. The amplification data and melt curve analysis of WGA reactions from Spike A, Spike B and Spike C which contained 0, 3, and 16 cells/microchannel eluate respectively are shown in FIG. 14A. The Selector reactions were run in duplicate and the results for both reactions are shown.

Selector Assay reactions done with the WGA material which showed amplification (Spike B and Spike C) were sequenced to verify the presence of the mutation. The location of the T790M specific mutation (CAT) is shown. See FIG. 14B. The region of Selector binding is indicated by the box below the sequence.

Results:

The genomic DNA material from the Spike and recovery experiment described above was whole genome amplified (WGA) and tested in the Selector Assay for the presence of the T790M mutation. Amplification was detected with the Spike B and Spike C samples as template, with 6 H1975 cells or 32 H1975 cells respectively used for the WGA reaction (see Methods). As expected, the Spike A (0 H1975 cells) sample did not show amplification. The melt curve analysis and sequencing results confirmed the presence of the T790M mutation in the WGA material in Spike B and Spike C samples. The Selector Assay was therefore successfully used also with WGA material from microchannel eluted cells and as low as six cell equivalents were WGA amplified and detected with the Selector Assay.

Methods:

Whole genome amplification of the H1975 material eluted from the channel was done using the Repli-g mini kit (Qiagen) according to manufacturer's instructions. Two microliter of the H1975 material eluted from the microchannel was used (Spike A: 0 cells/µl, Spike B: 3 cells/µl, Spike C: 16 cells/µl) for the WGA reaction. The amplified DNA's were diluted to 40 ng/µl in 10 mM Tris-HCl pH 8.0, 0.1 mM EDTA before addition to the Selector Assay. The Selector™ Assay was done as described for Example 9, except that 1 mM EGTA was added to the reaction.

Example 12. Selector Assay with an Overlapping Forward Primer

Figure 15B:
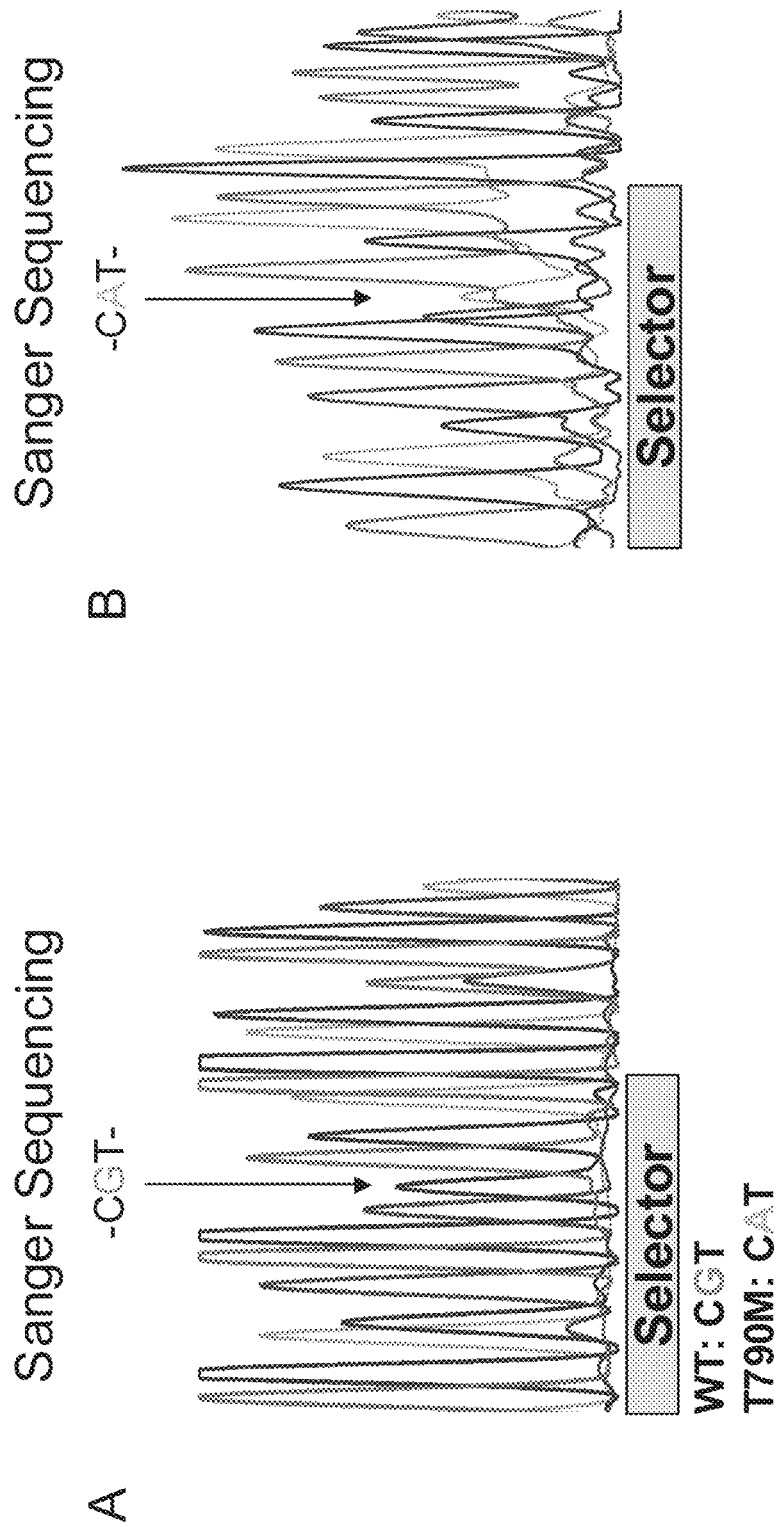
FIG. 15B: Sequencing results of the products from the Selector assay reactions shown in FIG. 15A. Panel A—Selector Assay reactions with wild-type template in the absence of Selector. Panel B—Selector Assay reactions with a mixture of wild-type template, Selector, and 50 pg H1975. The location of the T790M specific mutation (CAT) is shown. The region of Selector binding is indicated by the box below the sequences.

The Selector assay was done with a forward primer overlapping the Selector using wild-type template in the presence or absence of Selector. See FIG. 15A. Amplification of 50 pg H1975 in the presence of Selector and wild-type template was also tested. The Real-Time PCR and melt curve analyses of the Selector assay reactions are shown. For the melt curve analysis of −Selector PCR reactions, Selector and Reporter were added post-amplification.

Results:

Forward primer overlapping the Selector was used in the Selector assay. Different amounts of wild-type template were tested to determine the amount of wild-type template being blocked efficiently for amplification by Selector, but still allowing for efficient amplification of 50 pg H1975 mutant genomic DNA when present in the same reaction. Under the conditions used, it was determined that about 800 copies of wild-type template (calculation based on standard curve run in the absence of Selector; data not shown) are blocked for amplification and allow amplification of about 7 mutant copies (50 pg H1975) when present in the same mixture (See FIG. 15A). The Selector™ assay reactions of wild-type template in the absence of Selector (See FIG. 15B, panel A) and of a mixture of wild-type template and 50 pg H1975 mutant in the presence of Selector (See FIG. 15B, panel B) were sequenced to confirm the identity of the amplified template.

Methods:

Selector assay reactions and sequencing were done exactly as described for Example 9, except that forward primer FP14ovl (C*G*TGCARCTCA*T*C*A (SEQ ID NO: 15); R=A/G; * indicates phosphorothioate) was used for the Selector assay. The wild-type template was generated as described in Example 10 and the Selector assay data of the one thousand-fold dilution in 10 mM Tris-HCl pH 8.0, 0.1 mM EDTA are shown.

Figure 16:
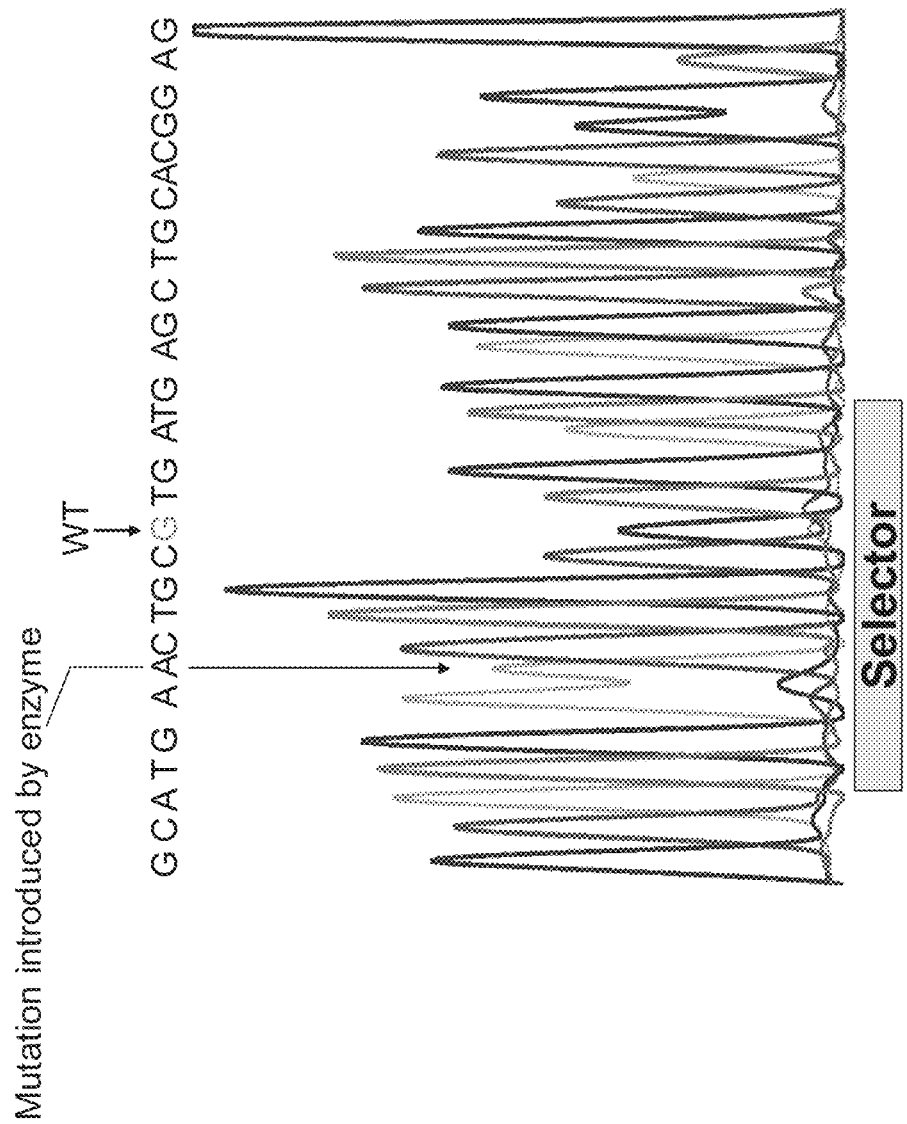
FIG. 16. Sanger sequencing of T790M Selector assay reaction done with AmpliTaq Gold DNA Polymerase using wild-type template in the presence of Selector. Regions of the EGFR gene that have mutations are shown (SEQ ID NO: 31).
Figure 17:
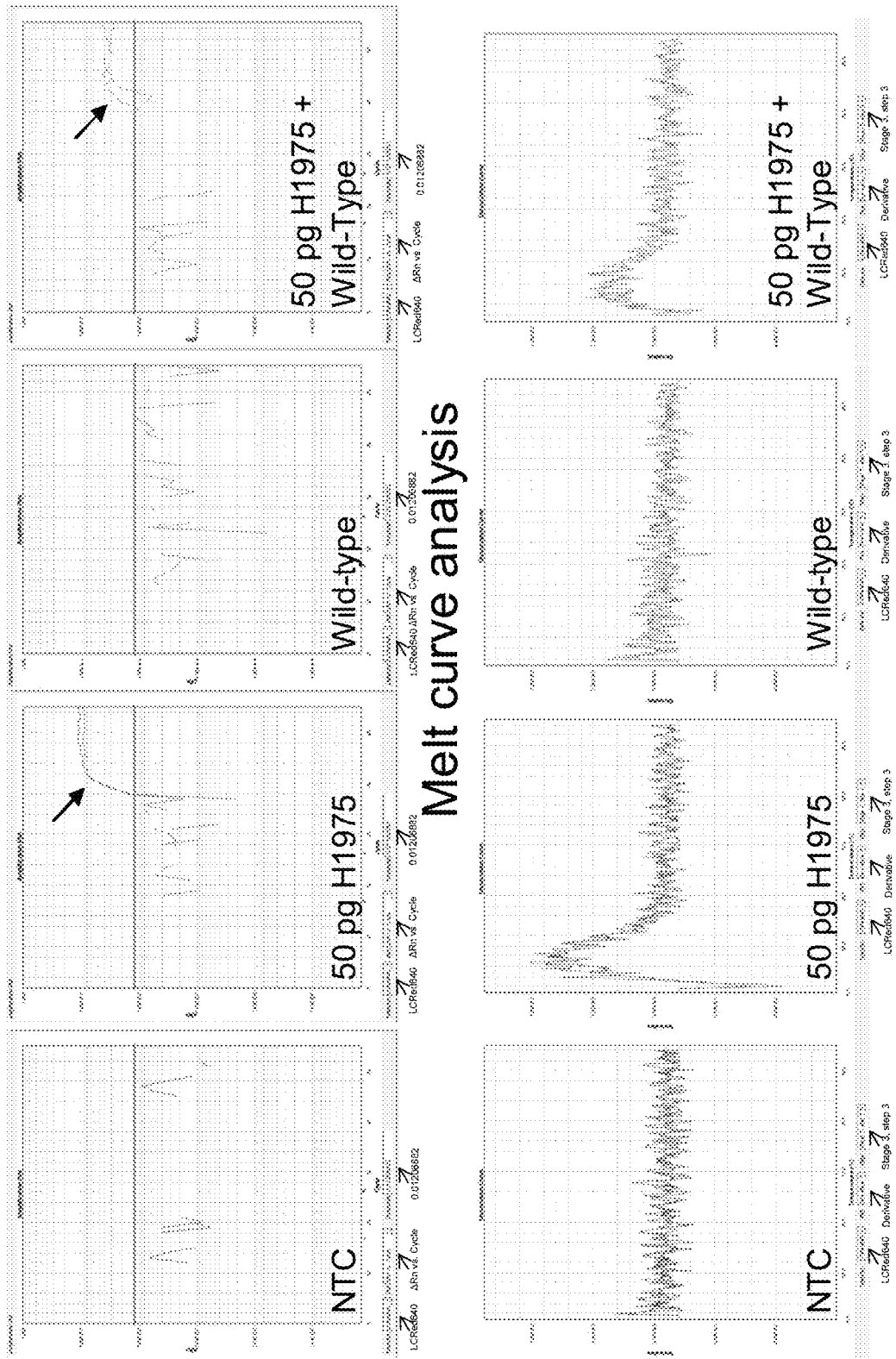
FIG. 17. Selector Assay with FAM-labeled blocker and LC-Red 640-labeled anchor.

Example 13. Enzymes with Low Fidelity Introduce Sequence Errors During Amplification and Reduce Performance In this example, AmpliTaq Gold DNA Polymerase was used in place of the high-fidelity/repair enzyme Kapa HiFi Hotstart DNA polymerase, as used in the previous examples. Other than a change in enzyme, the reaction conditions were equivalent to those in Example 6, with the exception of a slight reduction in denaturation to 95° C. and the use of 3 mM $Mg^{++}$ in the amplification buffer. Both changes were made to accommodate the requirements of the AmpliTaq enzyme. In FIG. 16, the arrow shows a G> A error introduced in the sequence associated with the low fidelity of the AmpliTaq Gold. The G nucleotide (marked as WT) altered in the T790M mutation to an A is also shown. The region of Selector binding is indicated by the box below the sequence. When this same assay is carried out using the Kapa HiFi enzyme, no significant amplification occurs, nor is there evidence for the introduction of any significant incorporation errors (see Example 7).

This example illustrates two key factors. First, the Selector assay gave better performance when carried out with high-fidelity enzymes like the Kapa HiFi enzyme, which has 3'exonuclease repair activity. Since the Selector assay is employed to detect rare events, any errors introduced by the enzyme may undermine assay performance. Thus high-fidelity enzymes, in combination with nuclease protected primers, blockers, and probes can be employed. Secondly, in this example the use of Selector and its ability to suppress wild-type signals, while allowing mutations to be amplified, provides a sensitivity model for any polymerase driven amplification reaction. Thus, this example provides direct evidence that the combination of nuclease resistant primers and high-fidelity enzymes, or combinations of enzymes, that possess 3' exonuclease repair activity will improve the performance, and maintain to a greater extent the sequence fidelity, of any polymerase dependent amplification reaction. These methods can be employed in any PCR reaction, including emulsion PCR and solid phase PCR, as well as applications to next generation sequencing and platforms.

The Selector assay highly suppresses amplification by the forward primer of wild-type sequences. At the same time, the reverse primer still drives linear amplification. If during this combined very low level amplification phase, an incorporation error occurs within the foot-print of the Selector, blocking by the Selector will be reduced and exponential amplification will occur. Further to this, one or more mis-incorporation errors are routinely observed when using AmpliTaq Gold. As such, employing high-fidelity polymerases with the methods of the present invention can reduce or prevent such errors.

Results:

The Selector assay was done in the presence of Selector using AmpliTaq Gold 0 DNA Polymerase and about 680 copies of wild-type template (prepared as described in Example 7). The same amount of wild-type template when used in the Selector assay with Kapa HiFi Hotstart DNA Polymerase and in the presence of Selector did not give any detectable amplification product (after 55 cycles of amplification). However, using AmpliTaq DNA Polymerase under similar cycling conditions (and with 5 mM, 7 mM or 10 mM $MgCl_2$) in the presence of Selector an amplification product was observed in every case and a melt curve peak indicating the presence of a mutant product (data not shown beyond FIG. 16). The sequencing of the mutant product from individual wells reveals that there are different mutations in the region of Selector binding (FIG. 16). The example shown here is a G>A mutation. Another frequently observed mutation is the T790M nucleotide G> A change. This indicates that the presence of Selector can lead to the selective amplification of the mutation introduced by the enzyme. Again, employing high-fidelity polymerases with the methods of the present invention can reduce or prevent such errors.

Methods:

Selector Assay reactions using the AmpliTaq Gold® DNA Polymerase were done in a 10 µl volume with the following components: 0.2 µM forward primer (same as described in Example 6), 2 µM reverse primer (same as described in FIG. 1), 0.3 µM Selector 6 (same as described in Example 6), 0.6 µM Reporter 4 (same as described in Example 6), 5 mM $MgCl_2$, 0.2 mM dNTP's, 3 U AmpliTaq Gold® (LifeTechnologies, Cat. No. 4311814), 1×PCR gold buffer (15 mM Tris-HCl pH 8.0, 50 mM KCl), 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 95° C. for 20 s, 61° C. for 30 s, 52° C. for 1 min, 69° C. for 15 s, followed by a dissociation curve analysis (95° C. for 1 min, 40° C. for 30 s then with 1% ramp to 95° C.). Detection of amplification product was done by monitoring 6-FAM and LC-Red 640 fluorescence during the 52° C. cycle step. For melt curve analysis the LC-Red 640 signal was monitored during the 40° C. to 95° C. transition. Sanger sequencing was done exactly as described for Example 6.

Example 14. Selector Assay Using a Simple FRET Reporter System

The Selector Assay amplification and melt curve analysis were carried out and are shown for reactions which were performed in presence of a FAM-labeled blocker (Blocker 8), and an LC-Red 640-labeled anchor (Anchor 5). A forward primer overlapping the blocker was used (see Methods for details) in the experiment shown in combination with the reverse primer described in Example 6. The Selector Assay was done using either 50 pg H1975 genomic DNA (contains about 7 copies T790M mutant) or about 1100 copies of wild-type EGFR DNA templates (prepared as described in Example 7). Amplification product is indicated in the Real-Time PCR graph by an arrow. (NTC: No template control)

Results:

The Selector Assay was done with FAM-labeled blocker (Blocker 8), an LC-Red 640-labeled anchor (Anchor 5), forward primer overlapping the blocker and the reverse primer used in previous experiments. Mutant amplification in 50 pg H1975 genomic DNA was detected (about 7 copies of T790M mutant), however, about 1100 copies of wild-type EGFR DNA template was efficiently blocked and did not show any amplification. Combining 7 copies H1975 with the approximately 1100 copies of wild-type EGFR showed again mutant amplification.

Methods:

Selector Assay reactions were done in a 10 μl volume with the following components: 0.5 μM forward primer (5'-C*G*TGCARCTCA*T*C*A-3' (SEQ ID NO: 15); R=A/G; * indicates phosphorothioate; overlaps blocker), 2 μM reverse primer (5'-T*G*TGTTCCCGGACAT*A*G*T-3'(SEQ ID NO: 11); *indicates phosphorothioate), 0.4 μM Blocker 8 (5'-2'OMe(U*C)*aucacgcagcu*c*a*(6-FAM)-3' (SEQ ID NO: 3); *indicates phosphorothioate; lower case indicates 2'-Fluoro Ribonucleoside), 0.4 μM Anchor 5 (5'-LC-Red 640-C3-C3*T*GC CCT TCG GCT GCC TC*C*T*C3-3'(SEQ ID NO: 4); *indicates phosphorothioate; lower case indicates 2'-Fluoro Ribonucleoside: C3 is a three-carbon spacer), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 μl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 1 min, 69° C. for 15 s, followed by a dissociation curve analysis (95° C. for 1 min, 40° C. for 30 s then with 1% ramp to 95° C.). Detection of amplification product was done by monitoring LC-Red 640 fluorescence during the 52° C. cycle step. For melt curve analysis the LC-Red 640 signal was monitored during the 40° C. to 95° C. transition.

Example 15. Detection of the KRAS G12C Mutation Using the Selector Assay

Amplification, melt curve analysis and sequencing results using H2122 genomic DNA (homozygous for G12C mutation) in a mixture with wild-type genomic DNA (control blood 17004; about 14000 copies of KRAS) were carried-out in the presence or absence of a KRAS Selector. Amplification product is indicated in the Real-Time PCR graph by an arrow (See FIG. 18). The nucleotide specific for the KRAS G12C mutation is indicated by an arrow in the sequencing results (Wild-type:C, G12C: A). The region of Selector binding is indicated by the box below the sequence.

Figure 18:
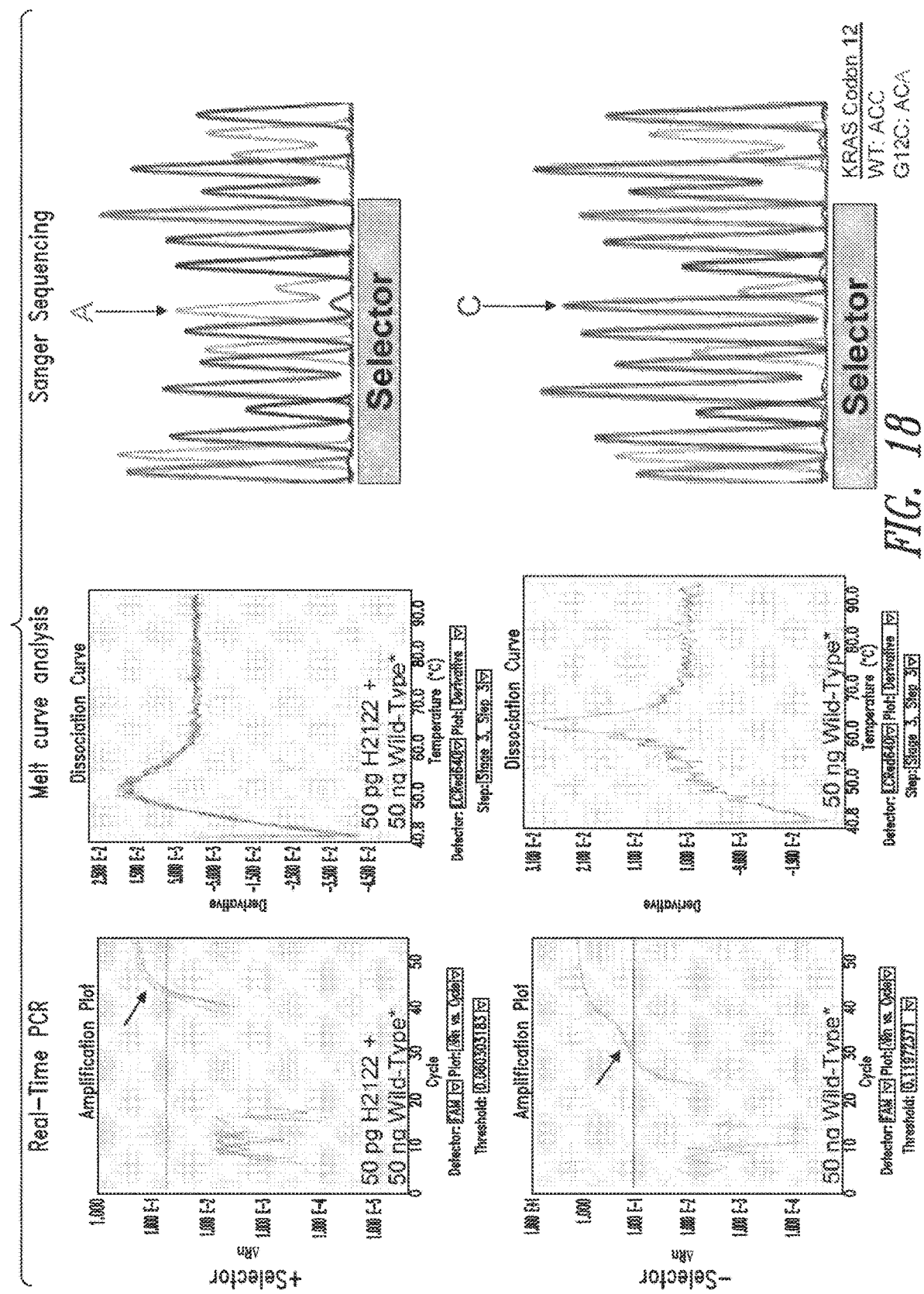
FIG. 18. Selector Assay for KRAS G12C mutation.

Results:

Selector Assay reactions for the KRAS G12C mutation were done using a mixture of 50 pg H2122 genomic DNA (homozygous for the G12C mutation; about 14 copies) and 50 ng wild-type genomic DNA (control blood 17004; about 14000 copies of KRAS) in the presence of Selector. We were able to detect mutant amplification, and the melt curve analysis of the amplification product showed a peak characteristic for the mutant (Tm of about 52° C.). This was confirmed by sequencing which showed the C>A nucleotide change specific for the G12C mutation (FIG. 18, upper panel). In contrast, the same amount of wild-type genomic DNA in the absence of Selector showed a melt curve peak shifted by about 12° C. to 64° C. when compared to the mutant. Sequencing confirmed the presence of the C nucleotide specific for KRAS wild-type in the amplified product (FIG. 18, lower panel).

Methods:

Selector Assay reactions were done in a 10 μl volume with the following components: 0.3 μM forward primer (5'-A*T*ATAAACTTGTGGTAGT*T*G*G-3'(SEQ ID NO: 16); * indicates phosphorothioate), 2 μM reverse primer (5'-G*C*ATATTAAAACAAGATTT AC*C*T*C-3'(SEQ ID NO: 17); *indicates phosphorothioate), 0.3 μM Selector 1 (5'-2'OMe(A*G)*cugguggcg*u*a*(LC Red 640)-3' (SEQ ID NO: 18); *indicates phosphorothioate; lower case indicates 2'-Fluoro Ribonucleoside), 0.5 μM Reporter 2 (5'-g*g*caa (6FAM) GAGTGCCuugacgauGGCAC*T*C* (Dabcyl)-3' (SEQ ID NO: 18); *indicates phosphorothioate; lower case indicates 2'-Fluoro Ribonucleoside), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 μl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 1 min, 69° C. for 15 s, followed by a dissociation curve analysis (95° C. for 1 min, 40° C. for 30 s then with 1% ramp to 95° C.). Detection of amplification product was done by monitoring 6-FAM and LC-Red 640 fluorescence during the 52° C. cycle step. For melt curve analysis the LC-Red 640 signal was monitored during the 40° C. to 95° C. transition. For Sanger sequencing, the PCR products were purified with the QIAquick PCR Purification Kit (Qiagen) and sequencing reactions were done using the BigDye® Terminator v1.1 Cycle Sequencing Kit (LifeTechnologies, Cat. No. 4337449) according to manufacturer instructions with sequencing primer (CATAGCAGCTGTTTTCCCA GTCATCGACGT-TGTACGTCCACAAAATGATTCTGAA (SEQ ID NO: 20)). Sequencing reactions were purified using Centri-Sep™ Columns (LifeTechnologies, Cat. No. 401762) and analyzed on the 3730 DNA Analyzer.

Genomic DNA from cell lines (H1975, H2122) was prepared using the QIAmp DNA Blood mini kit (Qiagen Cat. No. 51104) according to the protocol for cultured cells provided by the manufacturer. Genomic DNA from control blood samples (ABR16965, 17004) were prepared using the PAXgene Blood DNA kit (PreAnalytix Cat. No. 761133) and blood was collected in PAXgene Blood DNA tubes (PreAnalytix Cat. No. 761125).

Figure 19:
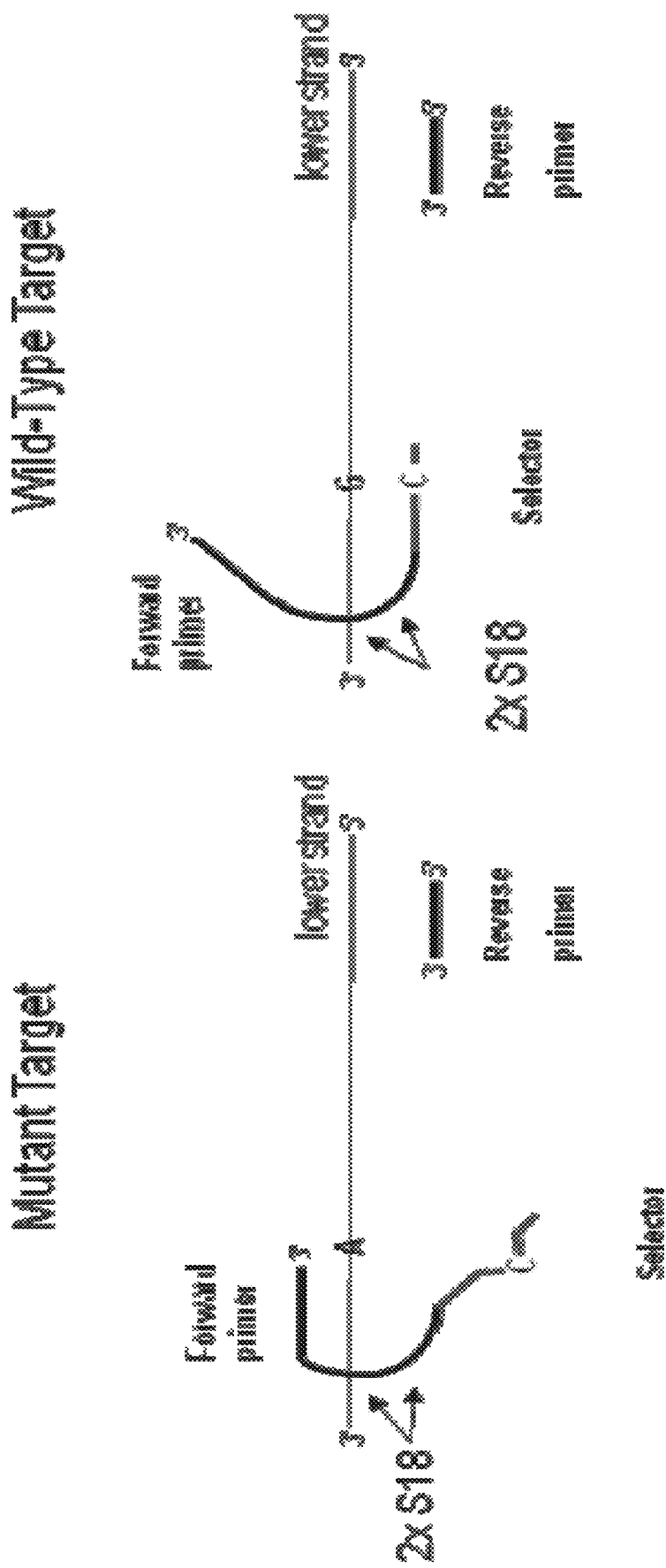
FIG. 19. A Switch-Blocker Construct Using Two S18 Spacers. This design is that described in Examples 15 and 16 for preferentially amplifying a T790M associated mutation.

Example 16. Point Mutation Discrimination by Use of a Primer Switch Oligonucleotide Construct in PCR Using Deep Vent (Exo−) DNA Polymerase Results:

The effect of the Primer-Switch oligonucleotide construct on the PCR discrimination between template sequences differing by a single point mutation was evaluated. A Primer-Switch construct for the detection of the T790M mutation was tested. This was done using synthetic wild-type and mutant target sequences. A Primer-Switch construction (see FIG. 19) was used for these studies and tested with the individual match and mismatch targets using real-time PCR analysis employing an intercalating SYTO® 9 dye (See Methods section). Results showed preferential amplification of the mutant T790M allele of about 4 delta Cq compared to the wild-type, giving respective real-time Cqs of 23 and 27 respectively.

Methods:

For these studies, two single stranded template sequences were prepared. The first sequence was named "wild type" (5'-TTGTGTTCCCGGACATAGTCCAGGAGGCAGC-CGAAGGGCATGAGCTGCGTGATG AGCTGCACG-GTGGAGGTGAGGCAGAT-3' (SEQ ID NO: 21)), and the second sequence was named "T790M" (5'-TTGTGTTC-CCGGACATAGTCCAGGAGGCAGCCGAAGGGCAT-GAGCTGCATGATG AGCTGCACGGTGGAGGTGAG-GCAGAT-3' (SEQ ID NO: 22)) were prepared. Each PCR mixture used the Switch-Blocker primer (3'-ACTACTC-GACGTGCCACCTCC-(5')-(S18)-(518)-cicATcAcGcA-GcTc-(C3)-3' (SEQ ID NOs: 23 and 24); lower case indicates 2'-Fluoro Ribonucleoside; C3 is a three-carbon spacer; S18 indicates a spacer 18 (hexaethylene glycol), and (5') indicates reverse synthesis of 5'-CCTCCACCGTGCAGCT-CATCA-3' (SEQ ID NO: 23)), as the forward primer, and an unmodified reverse primer (5'-CCGGACATAGTCCAG-GAGGCAG-3' (SEQ ID NO: 25)). Each primer was employed at 0.2 µM concentration in a 25 µL PCR set-up containing 0.2 mM dNTPs, 1× Thermopol buffer (New England Biolabs; 20 mM Tris-HCl, 10 mM (NH4)$_2$SO$_4$, 10 mM KCl, 2 mM MgSO4, 0.1% Triton X-100, pH 8.8 @ 25° C.), 1 Unit of Deep Vent (exo+) or Deep Vent (exo−) DNA polymerase (both from New England Biolabs); 2 µM SYTO® 9 (intercalating dye; Life Technologies); 1.5 µM ROX (reference dye; Agilent), and 105 copies of wild type or T790M template. Reactions were prepared in triplicate in 200 µL optical tubes and were run on an Agilent MX3005P real-time thermal cycler. Reactions were subjected to the following thermal cycling protocol: 95° C. @ 10 min; 40 cycles of [95° C. @40 sec, 58° C. @ 30 sec, 72° C. @ 1 min]; and 72° C. @ 7 min.

Example 17. Point Mutation Discrimination by Use of a Primer-Switch Oligonucleotide Construct in PCR—Comparison of Phusion® Hot Start II High-Fidelity DNA Polymerase and Deep Vent (Exo−) DNA Polymerases Results:

This study compared the Phusion® Hot Start II High-Fidelity DNA polymerase and Deep Vent (exo−) DNA polymerases when employed with the same Primer-Switch construction as well as the targets used in Example 16. PCR cycling conditions were slightly different than those used in Example 16 (see Methods), but beyond that reaction conditions were equivalent. Results gave about a delta Cq=3, favoring amplification of the mutant over wild-type with the Deep Vent (exo−) DNA polymerase (24.5 vs 27.5), while the Phusion Hot Start II polymerase favored mutant amplification over wild-type by about a delta Cq=6 (22 vs 28). This result indicates that the primer-switch construct works effectively with polymerases which posses 3'-exonuclease activity, as well as with polymerases that lack 3'exonuclease activity. It also indicates that enzymes with 3'exonuclease repair activity are preferred.

Methods:

Methods and primer-switch constructions were the same as in Example 16, with the following exceptions. The Phusion® Hot Start II High-Fidelity DNA polymerase reaction was carried out in 1× Phusion® HF Buffer (New England Biolabs), 1 Unit Phusion® Hot Start II High-Fidelity DNA was used (New England Biolabs). Additionally, cycling conditions were: 95° C. @ 3 min; 40 cycles of [95° C. @40 sec, 58° C. @ 30 sec, 72° C. @ 1 min]; and 72° C. @ 7 min.

Example 18. Switch-Blocker Designs for T790M Selective Amplification

Figure 20:
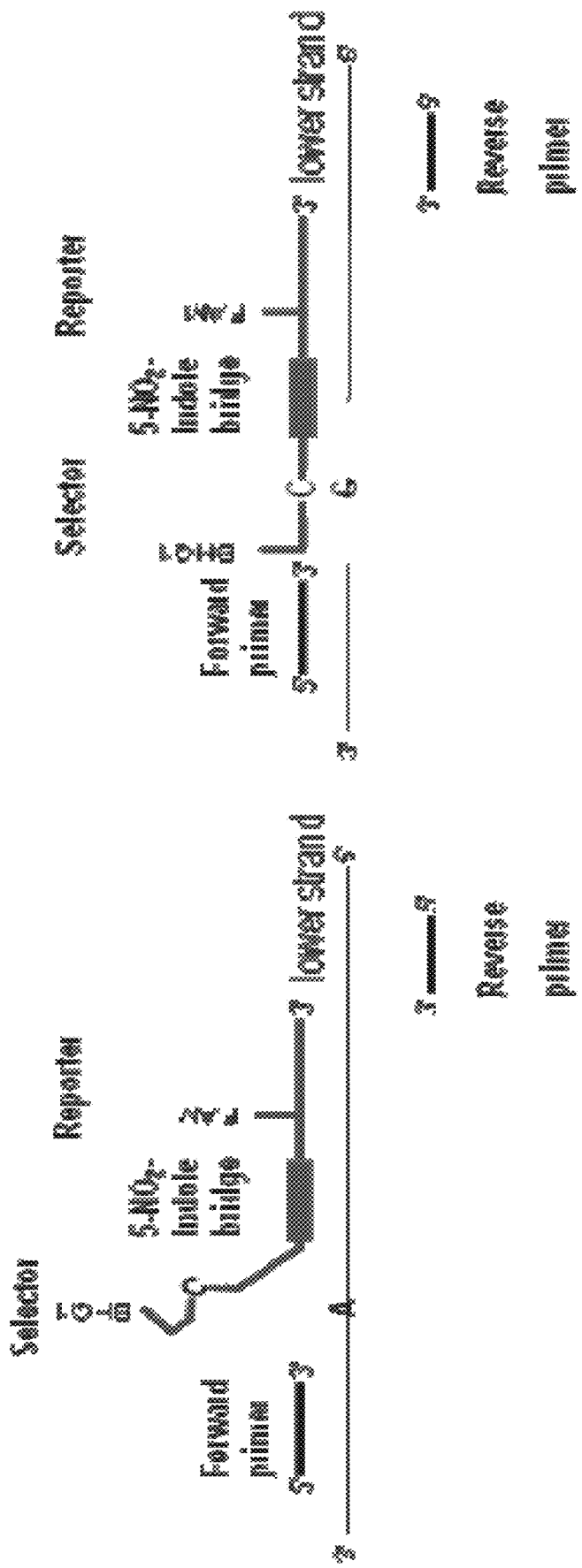
FIG. 20. A Switch-Blocker using a 5-nitroindole 'bridge" to increase variant allele discrimination. This design shows a preferential amplification for a variant allele associated with T790M. It also shows a self-reporting configuration using paired quencher and fluorescent label—fluorescence increasing upon hybridization.

Designs:

Oligonucleotides were designed and synthesized to study the selective amplification of the T790M allele compared to wild-type, using one of the Switch-Blocker approaches (See FIG. 20). Multiple forward primers were prepared to allow testing of the system over a range of annealing and extension temperatures. Additionally, the Switch-Blocker was synthesized to be "self-reporting" by placing a FAM fluorescent label seventeen nucleotides away from a 5' terminal BHQ1 (Black Hole Quencher 1) quencher. This placement was selected to create an optimal differential separation between the FAM fluorophore and BHQ1 quencher upon hybridization. Upon hybridization the seventeen nucleotide separation is equivalent to approximately one and one-half base turns which places the two labels on opposite sides of the duplex, aiding in achieving significant distance of the two labels from each other. Upon hybridization a marked increase in fluorescent associated with the FAM label will occur. Forward primer 1: 5'-TGCCTCACCTCCACCGTGCA*G*C*T-3' (SEQ ID NO: 26). Forward primer 2: 5'-CCTCACCTCCACCGTGCA*G*C*T-3' (SEQ ID NO: 27). Forward primer 3: 5'-CTCACCTCCACCGTGCA*G*C*T-3' (SEQ ID NO: 28). Switch blocker: 5'-BHQ1*2'OMe(G*A*U) CACGCA-GBBBBTGC(FAM)CCTTCGGCTGC-2'OMe(C*U*C) *C3-3' (SEQ ID NO: 29). Reverse primer: 5'-TTGTGTTCCCGGACATAGTCCA*G*G*A-3' (SEQ ID NO: 30) [*indicates phosphorothioate, B: 5-nitroindole, C3: three carbon spacer]

Evaluation of these constructs using the conditions set forth in the earlier examples, such as Examples 6 and 7, and testing over a range of annealing and extension temperatures should permit establishing optimized assay conditions for this Switch-Blocker T790M construct.

Example 19. Selector Assay with a Blunt Forward Primer and Switch Blocker

Figure 22A:
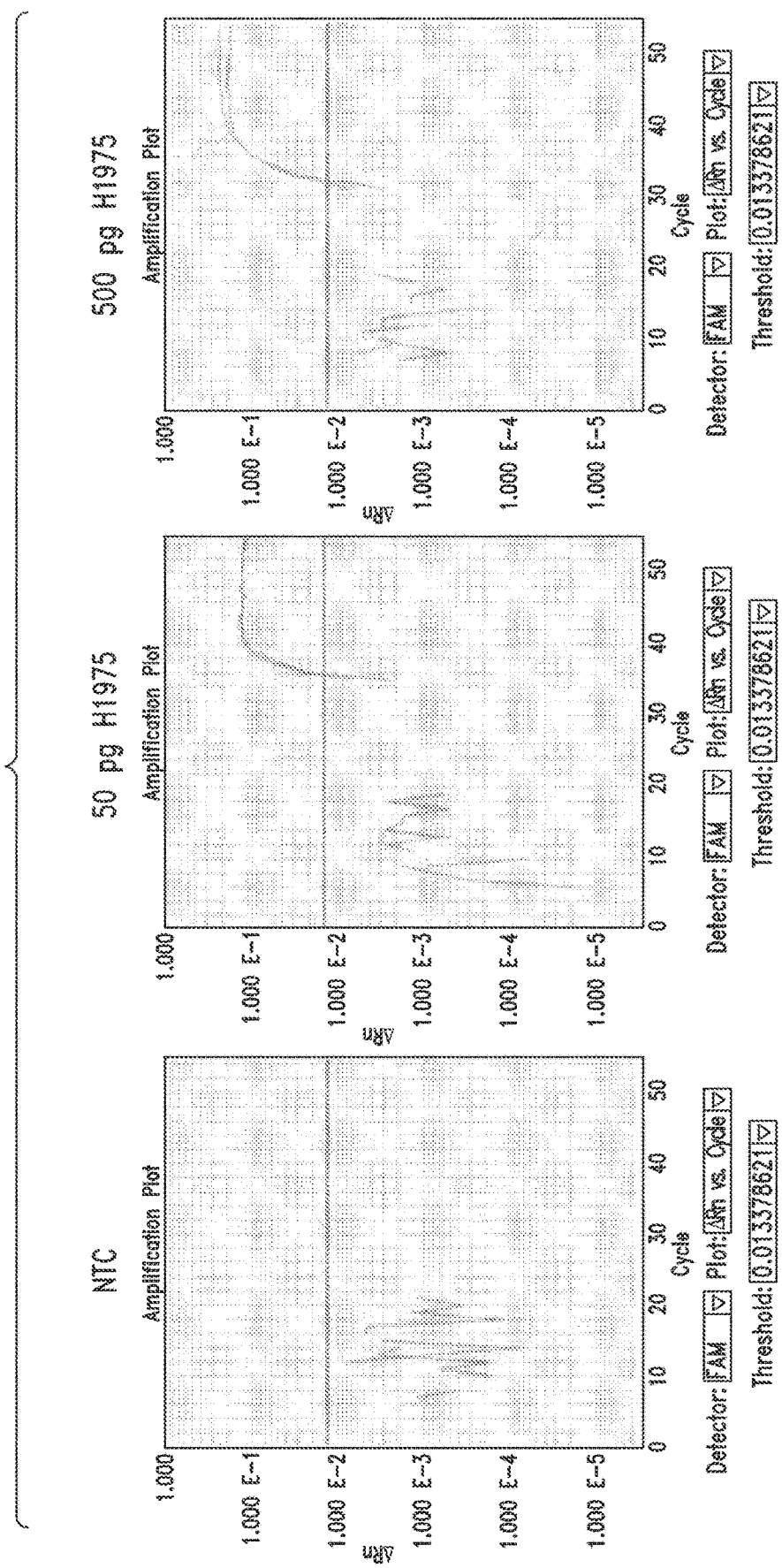
FIGS. 22A and 22B: T790M Selector assay with blunt forward primer and switch blocker.
Figure 22B:
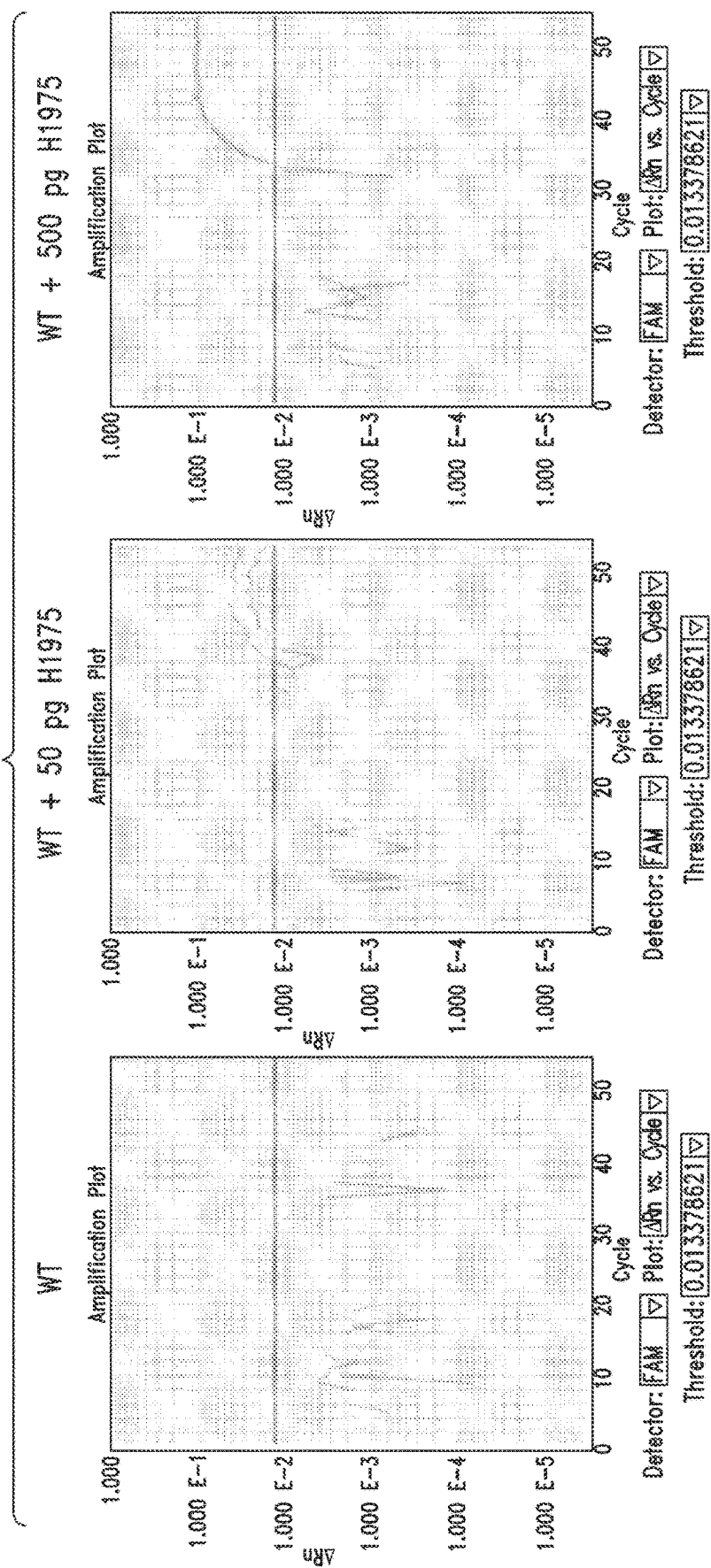
Figure 23:
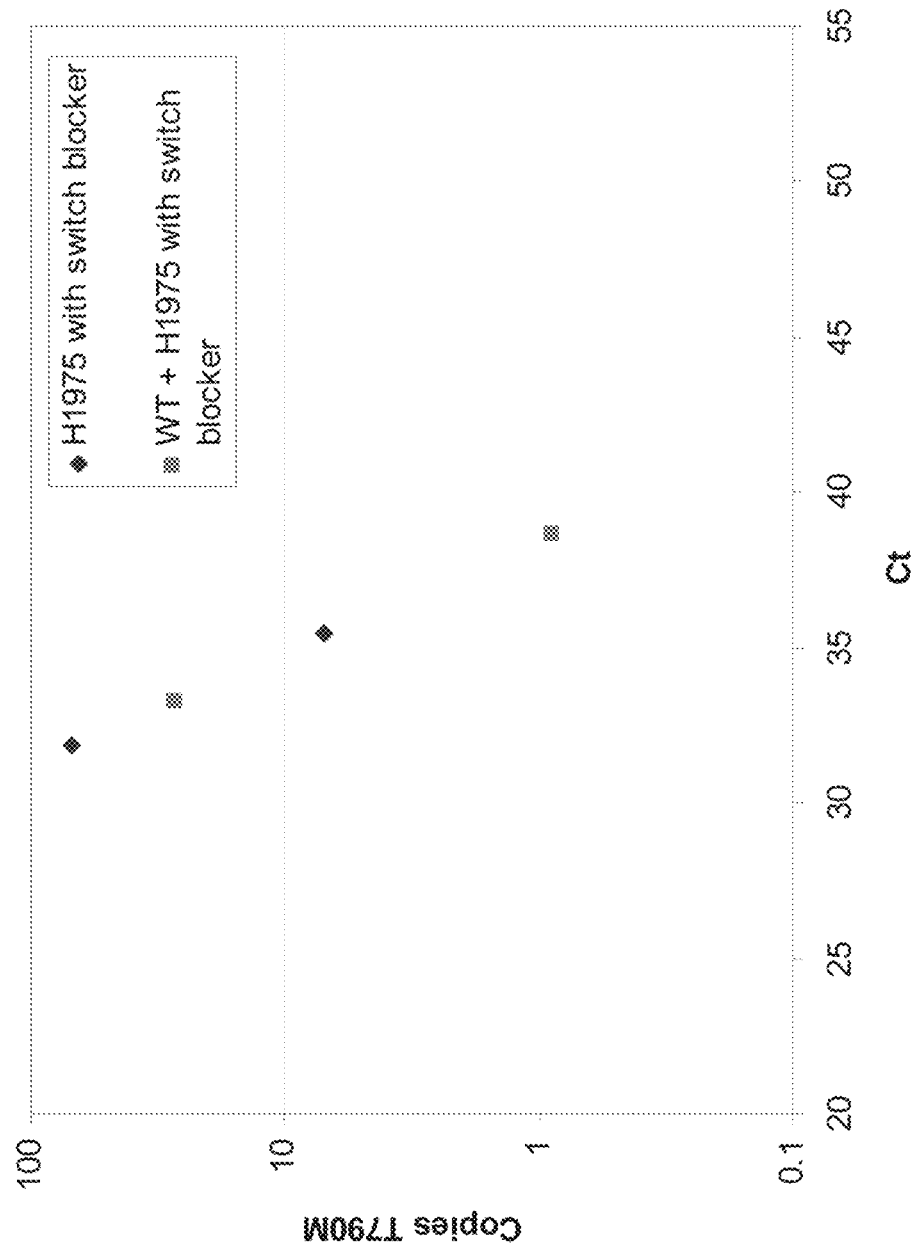
FIG. 23. T790M Selector assay with blunt forward primer and switch blocker.

Oligonucleotides were designed and synthesized to study the selective amplification of the T790M allele compared to wild-type, using one of the Switch-Blocker approaches (See FIGS. 22 and 23). Multiple forward primers were prepared to allow testing of the system over a range of annealing and extension temperatures. Additionally, the Switch-Blocker was synthesized to be "self-reporting" by placing a FAM fluorescent label seventeen nucleotides away from a 5' terminal BHQ1 (Black Hole Quencher 1) quencher. This placement was selected to create an optimal differential separation between the FAM fluorophore and BHQ1 quencher upon hybridization. Upon hybridization the seventeen nucleotide separation is equivalent to approximately one and one-half base turns which places the two labels on opposite sides of the duplex, aiding in achieving significant distance of the two labels from each other. Amplification of 50 pg or 500 pg H1975 was tested in the T790M Selector assay in the presence or absence of about 14000 copies of wild-type template. The amplification curves of duplicate reactions and a plot with the amplification data are shown (FIGS. 22 and 23). (NTC: no template control, WT: wild-type, H1975: T790M mutant).

Results:

The T790M Selector assay was done with blunt forward primer and switch blocker. The amplification of 50 pg or 500 pg H1975 can be detected in the presence of about 14000 copies of wild-type template.

Methods:

Selector Assay reactions with switch blocker were done in a 10 µl volume with the following components: 0.9 µM blunt forward primer (5'-C*A*CCGTGCA*R*C*T-3' (SEQ ID NO: 10); R=A/G; * indicates phosphorothioate), 2 µM reverse primer (5'-T*G*TGTTCCCGGACAT*A*G*T-3' (SEQ ID NO: 11); *indicates phosphorothioate), 0.5 switch blocker 2 BHQ1*2'OMe(G*A*U)CACGCAGBBBBTGC(FAM)CCTTCGGCTGC-2'OMe(C*U*C)*C3-3' (SEQ ID NO: 29); *indicates phosphorothioate; B indicates 5-nitroindole, C3 indicates three carbon spacer), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 10 s, 52° C. for 50 s, 69° C. for 15 sec, followed by a dissociation curve analysis (95° C. for 1 min, 40° C. for 30 s then with a 1% ramp to 95° C.). Detection of amplification product was done by monitoring 6-FAM fluorescence during the 10 s 50° C. cycle step and for melt curve analysis during the 40° C. to 95° C. ramp.

Example 20. Allele Specific Detection of T790M Using a Selector Blocker

Figure 24:
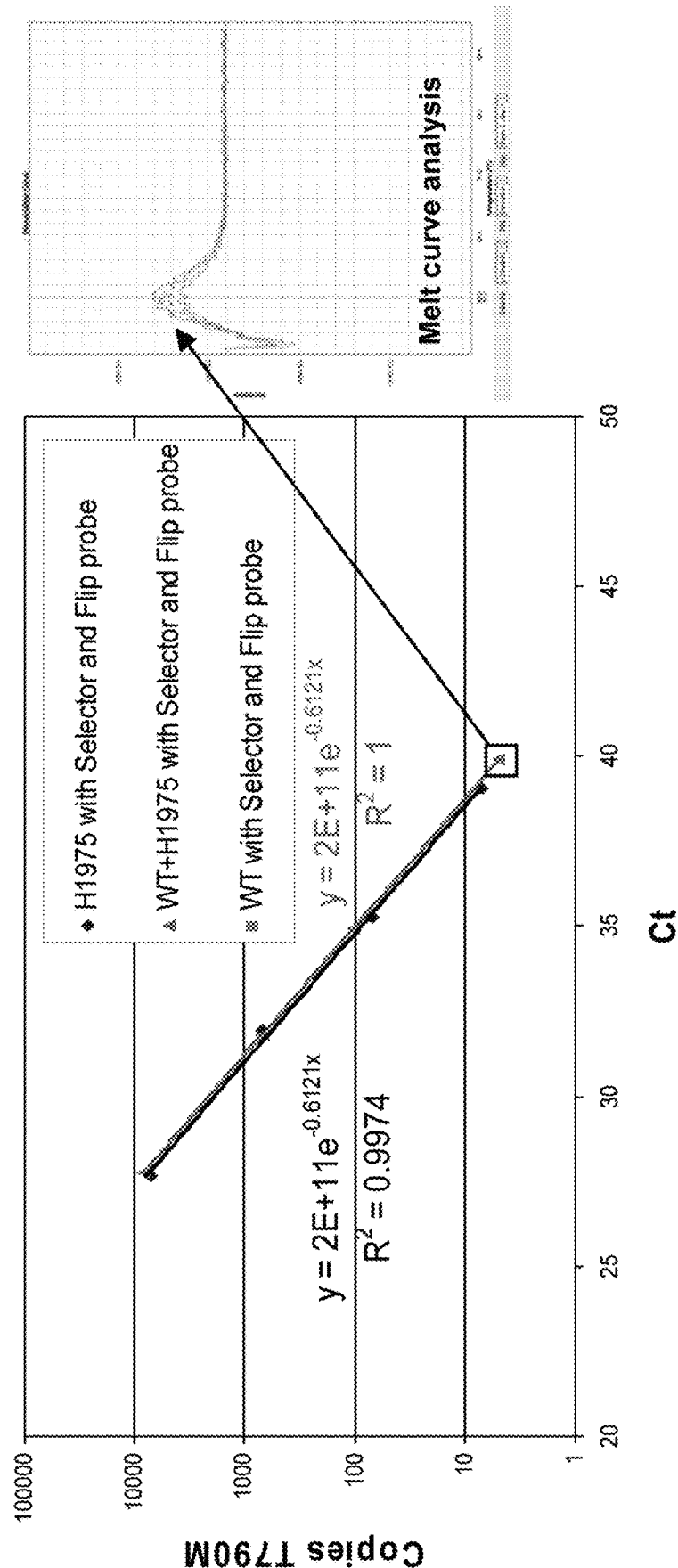
FIG. 24. T790M Selector assay with mutation-specific forward primer and Selector/Flip-probe pair in the presence or absence of excess wild-type template FIGS. 25A-25C. T790M Selector assay with mutation-specific forward primer with a wild-type target in the presence (FIG. 25A) or absence of a Selector blocker (FIG. 25B).

To demonstrate the degree to which a Selector blocker could improve an allele specific assay, the Selector blocker was used in combination with an allele specific forward primer for T790M. A T790M Selector assay amplification assay was carried out with increasing amounts of H1975 genomic DNA (50 pg, 500 pg, 5 ng or 50 ng) in the presence or absence of about 11300 copies of wild-type (WT) template. The melt curve analysis for the reaction product of the 50 pg H1975/wild-type mixture is also shown (FIG. 24; indicated by an arrow).
Results:
Increasing amounts of H1975 genomic DNA (from 7 up to about 7000 copies) were used in the Selector Assay in the presence of Selector and the presence or absence of about 11300 copies of wild-type template DNA. As can be seen from the amplification data graphs (FIG. 24), the presence of the wild-type control DNA minimally affects the amplification of the T790M mutant (compare H1975 to WT+H1975 graph). The amplification of the wild-type template in the presence of Selector and Flip probe is completely inhibited. Also, the melt curve analysis of the 7 copy H1975/11300 copy WT mixture shows a melt curve peak characteristic for the mutant.
Methods:
Selector Assay reactions were done as described for Example 6 except that 0.2 µM mutation-specific forward primer (5'-C*G*TGCARCTCAT*C*A*T-3' (SEQ ID NO: 36); R=A/G; * indicates phosphorothioate) was used. The wild-type template was prepared as described in Example 7.

Example 21. Demonstration that a Selector Blocker Significantly Increases the Sensitivity of Allele Specific Amplification Reactions Using an allele specific forward primer, the increased performance of the assay, due to the presence of a Selector blocker, was evaluated. Intrinsically, an allele specific forward primer should show a strong preference for selectively amplifying a specific target allele. In many cases, however, there is "break-through" of priming with non-specific target sequences. For example, an allele specific T790M forward primer can "break-through" in the presence of wild-type sequences. When this occurs a mutated sequence will be engrafted into the target sequence and additional amplification will erroneously indicate the presence of a T790M mutation, when in fact it is not there. To determine the amount of "break-through" and to determine the benefit of blocking the wild-type sequence using a Selector blocker, an allele specific amplification was performed for T790M in the presence of a wild-type sequence, with and without the Selector blocker.

Figure 25A:
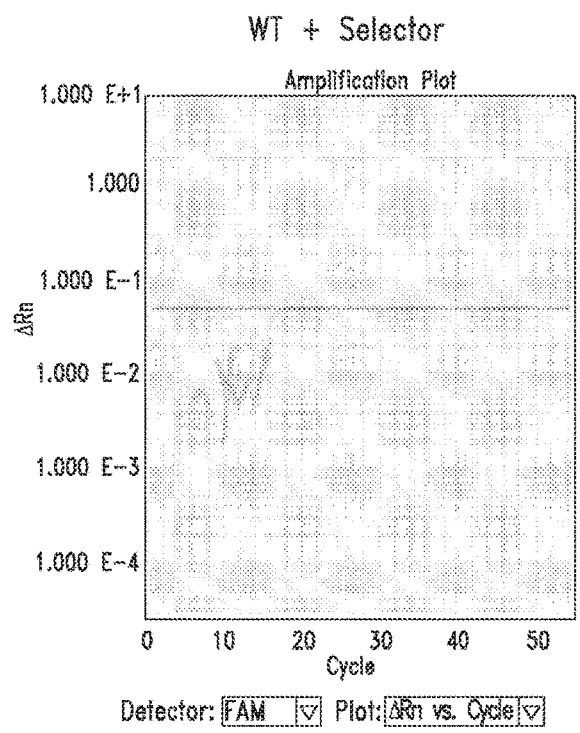
FIG. 25C is a plot of the T790M Selector assay results.
Figure 25B:
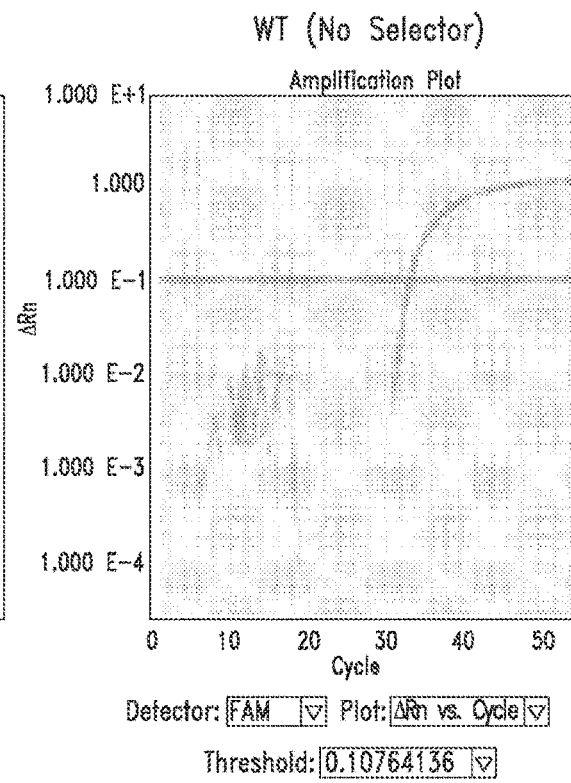
Figure 25C:
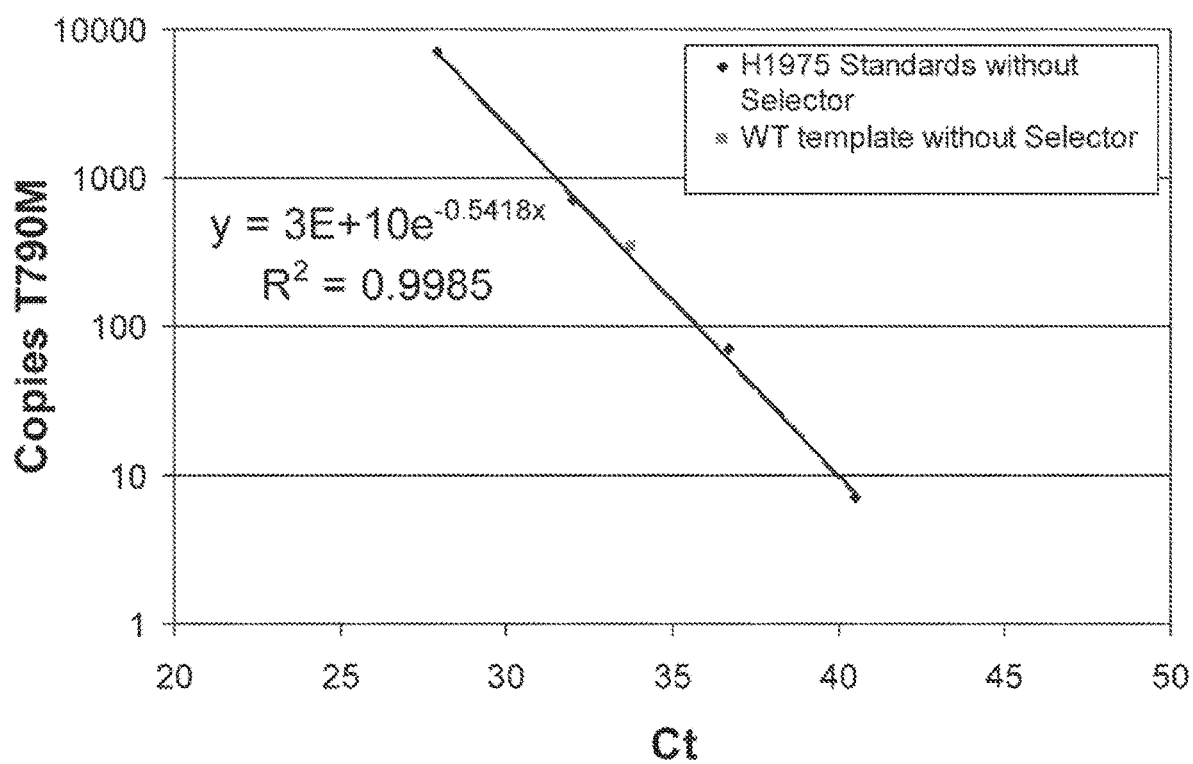

About 30,500 copies of wild-type (WT) template were used in the T790M Selector assay in the presence (A) or absence of Selector (B). In the absence of Selector the mutation-specific forward primer erroneously extends from the wild-type template.
Results:
The T790M Selector assay was done with mutation-specific forward primer in the presence or absence of Selector. As can be seen, addition of Selector completely inhibits amplification of wild-type template (see FIG. 25A). However, in the absence of Selector the mutation-specific forward primer is extended at a low level from the wild-type template (see FIG. 25B). From a standard curve run with H1975 genomic DNA in the absence of Selector it is estimated that the equivalent of about 340 mutation copies were obtained from the roughly 30500 copies of wild-type in the reaction. This is equivalent to an undesired "break-through" of about 1.1% which would significantly impair the sensitivity of the assay, if the Selector blocker was not present.
Methods:
Selector Assay reactions were done as described for Example 6 except that 0.2 µM mutation-specific forward primer (5'-C*G*TGCARCTCAT*C*A*T-3' (SEQ ID NO: 36); R=A/G; * indicates phosphorothioate) was used. The wild-type template was prepared as described in Example 7.

Figure 26:
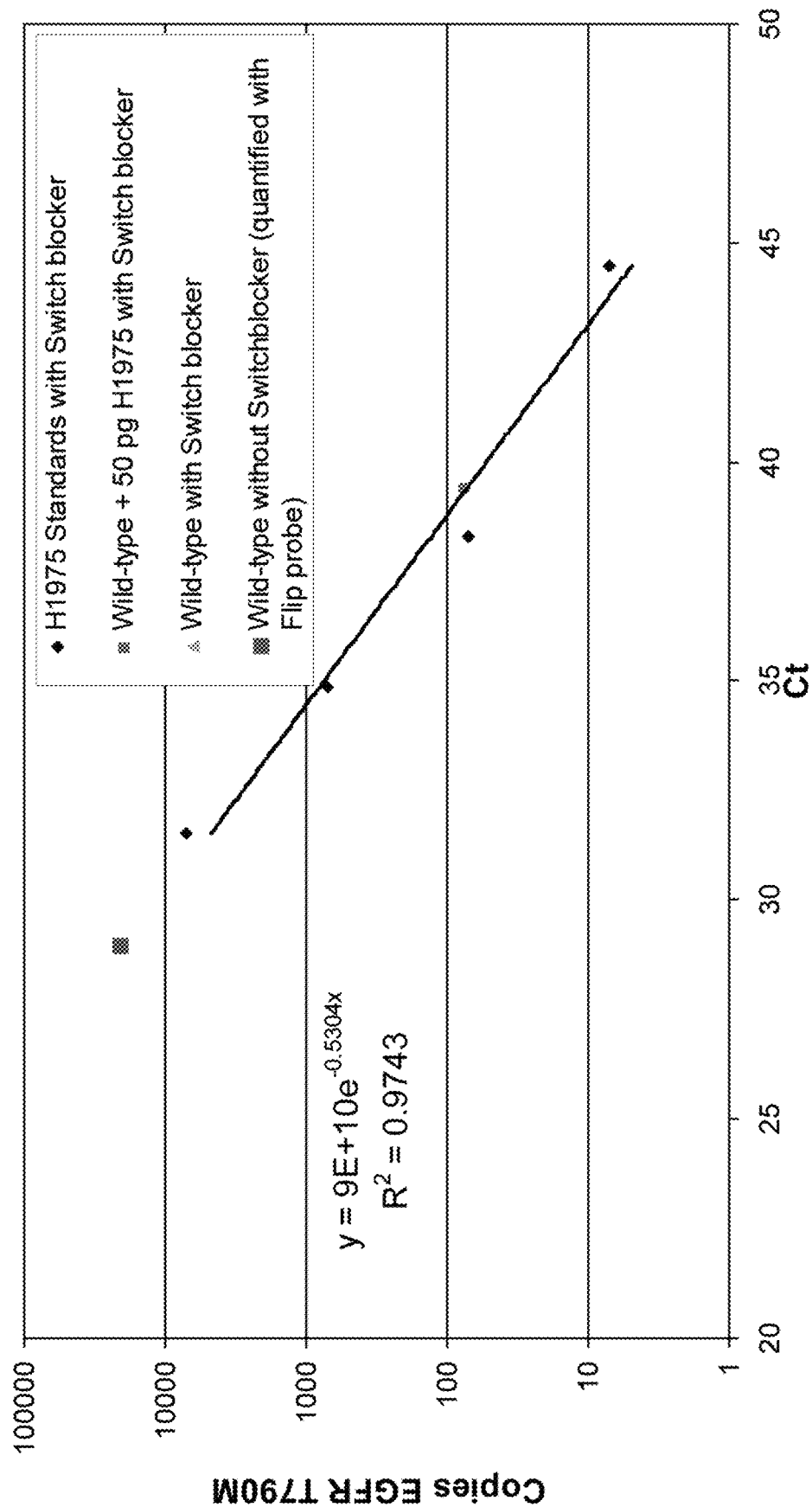
FIG. 26. Amplification of T790M mutant with mutation-specific forward primer in the presence or absence of excess wild-type EGFR and switch blocker.

Example 22. Selective Amplification of T790M Using a Switch Blocker #1 in the Presence and Absence of Excess Wild-Type EGFR To demonstrate the effectiveness of a switch-blocker #1 for inhibiting wild-type, while not effecting mutation amplification, wild-type template (about 20900 copies) was added to Selector reactions in the presence or absence of the switch blocker (see FIG. 26). A standard curve was created by running increasing amounts of H1975 genomic DNA (0.05 ng, 0.5 ng, 5 ng or 50 ng, which corresponds to 7, 70, 700 and 7000 copies T790M respectively) in the presence of switch blocker #1. The amplification data of 50 pg H1975 mutant in the mixture with wild-type template is shown (wild-type copies were quantified by doing the Selector Assay in the absence of switch blocker and using Reporter 4 in combination with the forward primer used as described in Example 6). The amplification data of the average of triplicate reactions are plotted.
Results:
In the presence of switch blocker the amplification of about 20900 copies of wild-type EGFR is completely inhibited. The addition of 50 pg H1975 (about 7 copies) can be detected in the excess wild-type background (see FIG. 26).
Methods:
Selector Assay reactions with switch blocker #1 were done in a 10 µl volume with the following components: 0.8 µM mutation-specific forward primer (5'-C*G*TGCARCTCAT*C*A*T (SEQ ID NO: 36); R=A/G; * indicates phosphorothioate), 3 µM reverse primer (5'-T*G*TGTTCCCGGACAT*A*G*T-3' (SEQ ID NO: 11); *indicates phosphorothioate), 0.5 µM switch blocker #1 BHQ1*2'OMe(G*A*U)CACGCAGBBBBTGC(FAM)CCTTCGGCTGC-2 'OMe(C*U*C)*C3-3' (SEQ ID NO: 29); *indicates phosphorothioate; B indicates 5-nitroindole, C3 indicates three carbon spacer), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). Selector Assay reactions without switch blocker were done with forward primer (5'-C*A*CCGTGCAR*C*T*C-3' (SEQ ID NO: 10), * indicates phosphorothioate, R=G/A), same reverse primer as above, 0.6 µM Reporter 4 (5'-u*g*ccc(C7-NH)(6-FAM) TTCGGCTGCcuccuGGAGCCG*A*A*(Dabcyl)-3' (SEQ ID NO: 37); *indicates phosphorothioate; lower case indicates 2'-Fluoro Ribonucleoside). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 10 s, 52° C. for 50 s, 69° C. for 15 s, followed by a dissociation curve analysis (95° C. for 1 min, 40° C. for 30 s then with a 1% ramp to 95° C.). Detection of amplification product was done by monitoring 6-FAM fluorescence during the 10 s 52° C. cycle step and for melt curve analysis during the 40° C. to 95° C. ramp. The Wild-type template used was prepared as described in Example 7.

Figure 27:
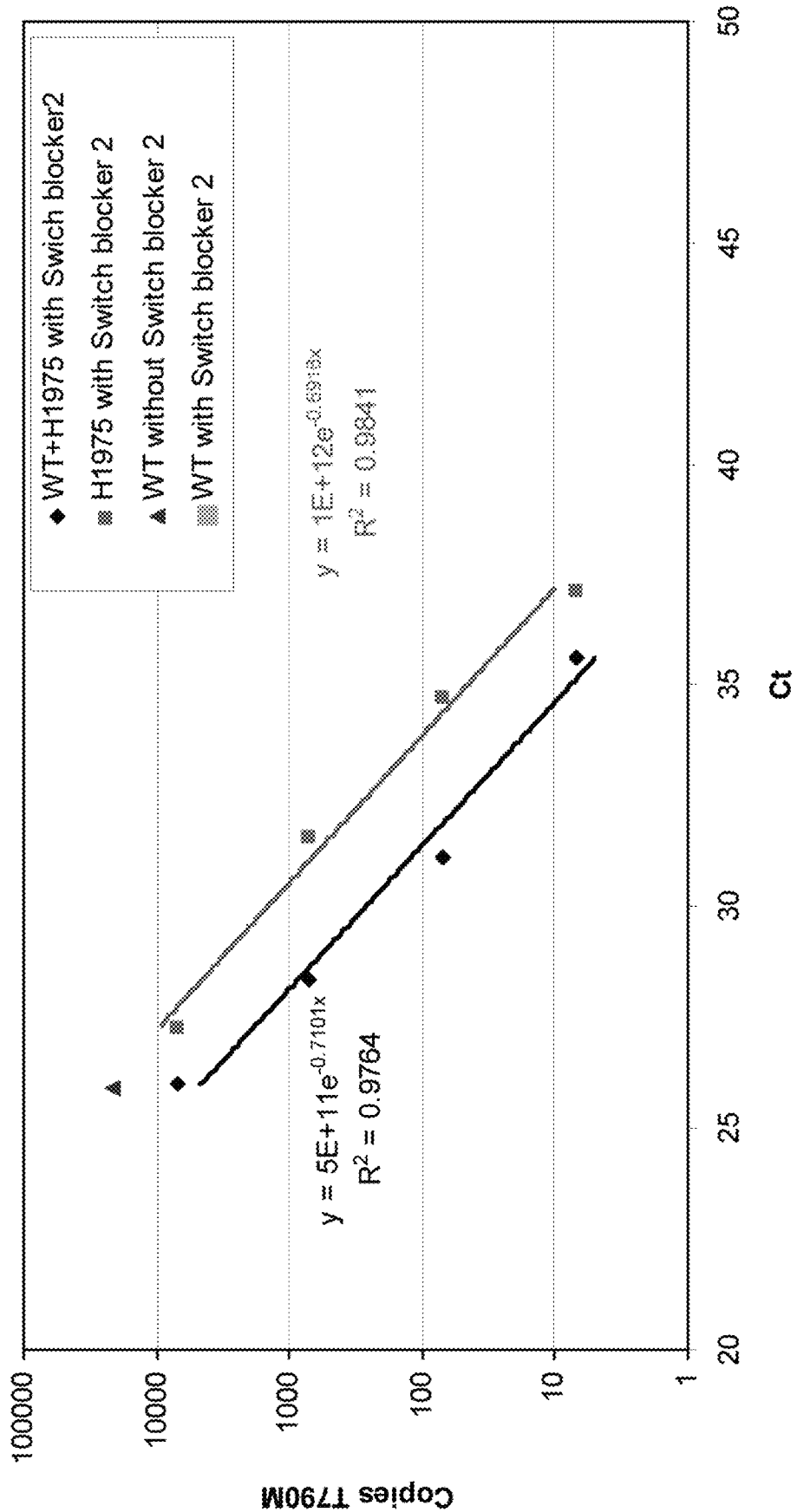
FIG. 27. Amplification of T790M mutant with mutation-specific forward primer in the presence or absence of excess wild-type EGFR and switch blocker #2.

Example 23. Selective Amplification of T790M Using a Switch Blocker #2 in the Presence and Absence of Excess Wild-Type EGFR To demonstrate the effectiveness of a switch-blocker #2 for inhibiting wild-type, while minimally effecting mutation amplification, wild-type template was added to Selector reactions in the presence or absence of the switch blocker #2 (see FIG. 27). Increasing amounts of H1975 genomic DNA (0.05 ng, 0.5 ng, 5 ng or 50 ng, which corresponds to 7, 70, 700 and 7000 copies T790M respectively) were used in the Selector Assay in the presence or absence of about 21640 copies of wild-type EGFR and switch blocker #2 (wild-type copies were quantified by doing the Selector Assay in the absence of switch blocker #2 and using Reporter 4 in combination with the forward primer used in Example 6). The amplification data of the average of triplicate reactions are plotted and used for the trendline in the graph (see FIG. 27).
Results:
In the presence of switch blocker #2 the amplification of about 21640 copies of wild-type EGFR is completely inhibited. The addition of increasing amounts of H1975 shows the quantitative nature of the assay. Amplification of the T790M mutant with switch blocker #2 is increased somewhat by the presence of wild-type EGFR sequences (FIG. 27).
Methods:
Selector Assay reactions with switch blocker #2 were done in a 10 µl volume with the following components: 0.8 µM mutation-specific forward primer (5'-C*G*TGCARCTCAT*C*A*T (SEQ ID NO: 36); R=A/G; * indicates phosphorothioate), 3 µM reverse primer (5'-T*G*TGTTCCCGGACAT*A*G*T-3' (SEQ ID NO: 11); *indicates phosphorothioate), 0.5 µM switch blocker #2 BHQ1*2'OMe(C*A*U)CACGCAGBBBBTGC(FAM) CCTTCGGCTGC-2'OMe(C*U*C)*C3-3 (SEQ ID NO: 29); *indicates phosphorothioate; B indicates 5-nitroindole, C3 indicates three carbon spacer), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). Selector Assay reactions without switch blocker #2 were done with forward primer (5'-C*A*CCGTGCAR*C*T*C-3' (SEQ ID NO: 10), * indicates phosphorothioate, R=G/A), same reverse primer as above and 0.6 µM Reporter 4 (5'-u*g*ccc(C7-NH)(6-FAM) TTCGGCTGCcuccuGGAGCCG*A*A*(Dabcyl)-3' (SEQ ID NO: 37); *indicates phosphorothioate; lower case indicates 2'-Fluoro Ribonucleoside). PCR reactions were loaded on a 384-well plate and PCR cycling was done in an ABI 7900HT instrument with the following cycling conditions: 95° C. for 5 min, 55 cycles of 98° C. for 20 s, 61° C. for 30 s, 52° C. for 1 min, 69° C. for 15 s, followed by a dissociation curve analysis (95° C. for 1 min, 40° C. for 30 s then with a 1% ramp to 95° C.). Detection of amplification product was done by monitoring 6-FAM fluorescence during the 52° C. cycle step and for melt curve analysis during the 40° C. to 95° C. ramp. The Wild-type template used was prepared as described in Example 7.

Example 24. Melt Profiles of the High Tm Switch Blocker

Figure 28A:
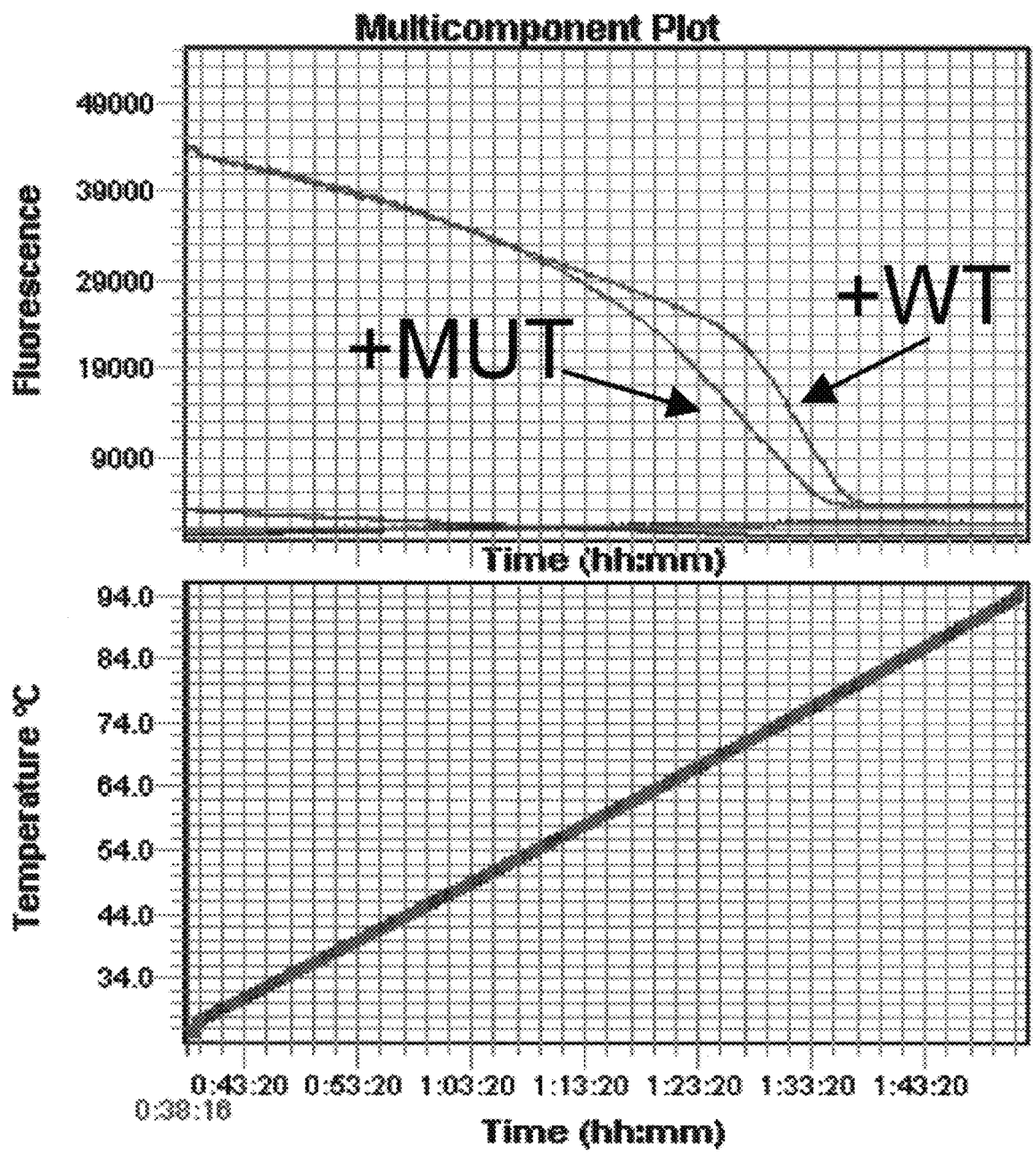
FIGS. 28A and 28B. Melt profile of high Tm switch blocker with wild-type (WT) or T790M mutation containing (MUT) synthetic target in the absence (FIG. 28A) or presence of spermidine (FIG. 28B).
Figure 28B:
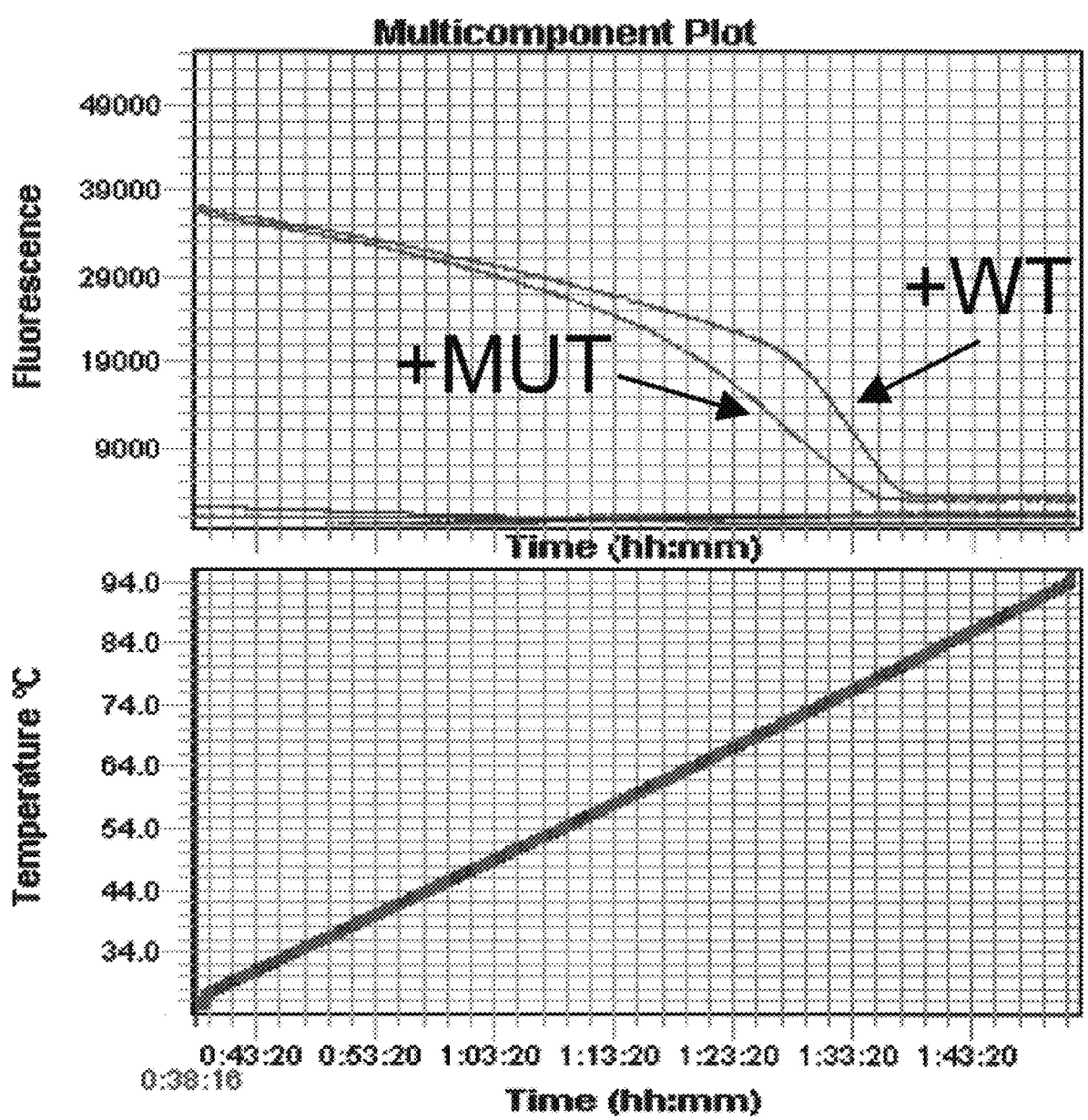

A high Tm switch-blocker was designed to incorporate a switch portion that could be highly responsive to the presence of a mutation. To determine that the switch portion was particularly responsive to the presence of a mismatch, melt profiles were conducted with mutant and wild-type targets. The melting profile of high Tm switch blocker in the presence of wild-type or T790M mutant synthetic target and the presence or absence of spermidine was tested (see FIG. 28). The FAM fluorescence (upper panel) and temperature gradient (lower panel) from 25° C. to 95° C. over time is shown.
Results:
Binding of the high Tm switch blocker to the target template leads to an increase in fluorescence (because of separation of the quencher from the fluorophore in the high Tm switch blocker), similarly release of the high Tm switch blocker from the target template leads to a decrease in fluorescence. To demonstrate the temperatures at which the high Tm switch blocker is released from wild-type or T790M mutant templates, changes in the fluorescence of high Tm switch blocker-target complexes was monitored over a temperature gradient from 25° C. to 95° C. The complexes were created by heating up the reactions to 95° C. and cooling them slowly to 25° C. As can be seen in the upper panels for control and spermidine reactions, the melting profile of the wild-type template shows a higher temperature dissociation compared to the mutant template. For the entire blocker it is apparent that the wild-type Tm is about 74° C. whereas for the T790M mutant it is about 68° C. Adding spermidine to the reaction leads to a slight increase of melting temperatures for wild-type and mutant templates of about 2° C. (with spermidine: wild-type Tm is about 76° C., T790M mutant about 70° C.). Significantly, however, in both cases, the presence of a mutant leads to a biphasic melt profile, whereas the melt profile with the wild-type is monophasic. This indicates that the switch portion is melting separately from the rest of the switch-blocker in response to a mutation. In the presence of a mutation, these biphasic profiles are consistent with the "switch-portion" melting at 50° C. to 60° C., while the entire blocker does not dissociate from the mutant targets until a temperature of 68° C.-70° C. is achieved. Similar but slightly less striking biphasic melt curves are seen in the absence of spermidine (see FIG. 28, control).
Methods:
The melting profile was done in a 10 µl volume with the following components: 0.4 µM high Tm switch blocker BHQ1*2'OMe(C*A*U)cacgcagBBBBTGC(FAM)CCTT CGGCTGCCTCCTGGACTATGTC-2'OMe(C*G*G)*C3-3' (SEQ ID NO: 29); *indicates phosphorothio-ate; B indicates 5-nitroindole, lower case indicates 2' Fluoro Ribonucleoside, C3 indicates three carbon spacer), 2 µM wild-type synthetic target 5'-GAGCAGGTACTGGGAGCCAATATTGTCTTTGTGT-TCCCGGACATAGTC CAGGAGGCAGC-CGAAGGGCATGAGCTGCGTGATGAGCTGCACG-GTGGAGGTGA-3' (SEQ ID NO: 38) or T790M mutant synthetic target 5'-GAGCAGGTACTGGGA GCCAATATT-GTCTTTGTGTTCCCGGACATAGTCCAGGAGGCAGC-CGAAGGGCATG AGCTGCATGATGAGCTGCACG-GTGGAGGTGA-3', (SEQ ID NO: 39), 3 mM MgCl$_2$, 1×HiFi buffer, 0.2 µl ROX reference dye (LifeTechnologies, Cat. No. 12223-012). Spermidine (SIGMA S-0266) was added where indicated at a final concentration of 0.5 mM. PCR reactions were loaded on a 384-well plate and PCR cycling was done in an ABI 7900HT instrument with the following cycling conditions: 95° C. for 1 min, 2% ramp to 25° C. then hold for 30 s, and 1% ramp to 95° C. and hold for 30 s. Detection of the melt profile was done by monitoring 6-FAM fluorescence during the 25° C. to 95° C. transition.

Example 25. Allele Specific Assay with High Tm Switch Blocker

Figure 29:
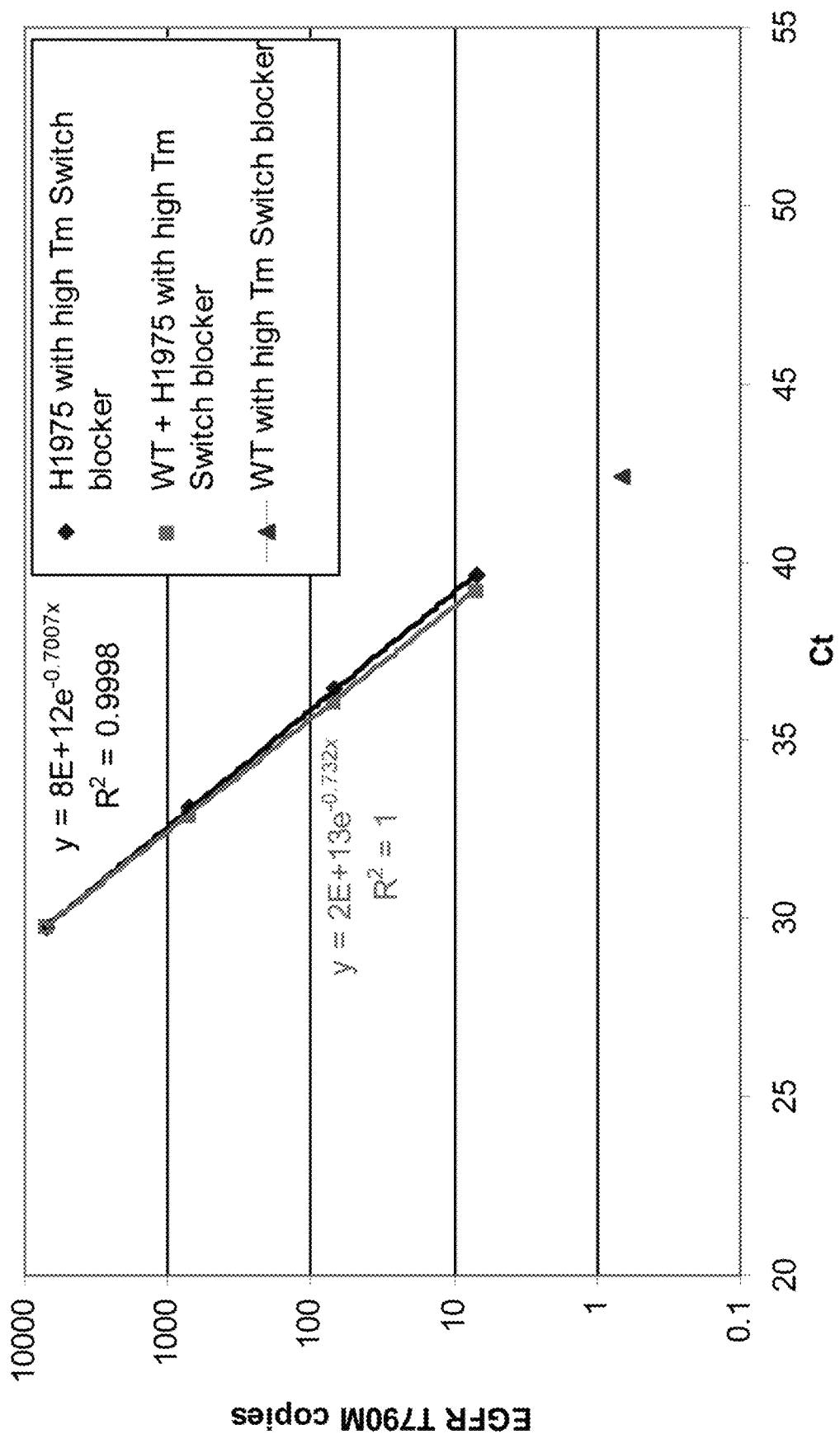
FIG. 29. T790M Selector assay with high Tm switch blocker and mutation-specific forward primer.

An allele specific assay was carried out using the high Tm switch blocker. Increasing amounts of H1975 genomic DNA (0.05 ng, 0.5 ng, 5 ng or 50 ng, which corresponds to 7, 70, 700 and 7000 copies T790M respectively) were used in the Selector Assay in the presence or absence of about 14000 copies of wild-type EGFR and high Tm switch blocker (see FIG. 29). The amplification data of the average of triplicate reactions are plotted and used for the trendline in the graph (average of six for reactions containing 50 pg H1975).
Results:
Increasing amounts of H1975 genomic DNA (equivalent from 7 to up to about 7000 copies of T790M) were used in the Selector Assay in the presence of high Tm switch blocker and about 14000 copies of wild-type EGFR (added in the form of 50 ng LnCAP genomic DNA). The data here show that the presence of wild-type DNA minimally affects mutant amplification over a wide range of concentrations.
Methods:
Selector Assay reactions with high Tm switch blocker were done in a 10 µl volume with the following components: 0.3 µM mutation-specific forward primer (5'-C*T*CCACCGTGCARCTCAT*C*A*T-3' (SEQ ID NO: 40); R=A/G; * indicates phosphorothioate), 0.3 µM reverse primer (5'-T*G*AGCAGGTACTGGGAGCC-AATATTGTCTTTGTGT*T*C*C-3' (SEQ ID NO: 41); *indicates phosphorothioate), 0.5 µM high Tm switch blocker 2 (5'-BHQ1*2'OMe(C*A*U)cacgcagBBBBTGC (FAM)CCTTCGGCTGCCTCCTGGACTATGT C-2'OMe (C*G*G)*C3-3' (SEQ ID NO: 42); *indicates phosphoro-thioate; B indicates 5-nitroindole, lower case indicates 2' Fluoro Ribonucleoside, C3 indicates three carbon spacer), 3 mM MgCl$_2$, 0.4 mM dNTP's, 0.2 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 55 cycles of 98° C. for 20 s, 71° C. for 10 s, 50° C. for 8 s, 66° C. for 1 min, followed by a dissociation curve analysis (95° C. for 1 min, 40° C. for 30 s then with a 1% ramp to 95° C.). Detection of amplification product was done by monitoring 6-FAM fluorescence during the 50° C. cycle step and for melt curve analysis during the 40° C. to 95° C. ramp.

Figure 30:
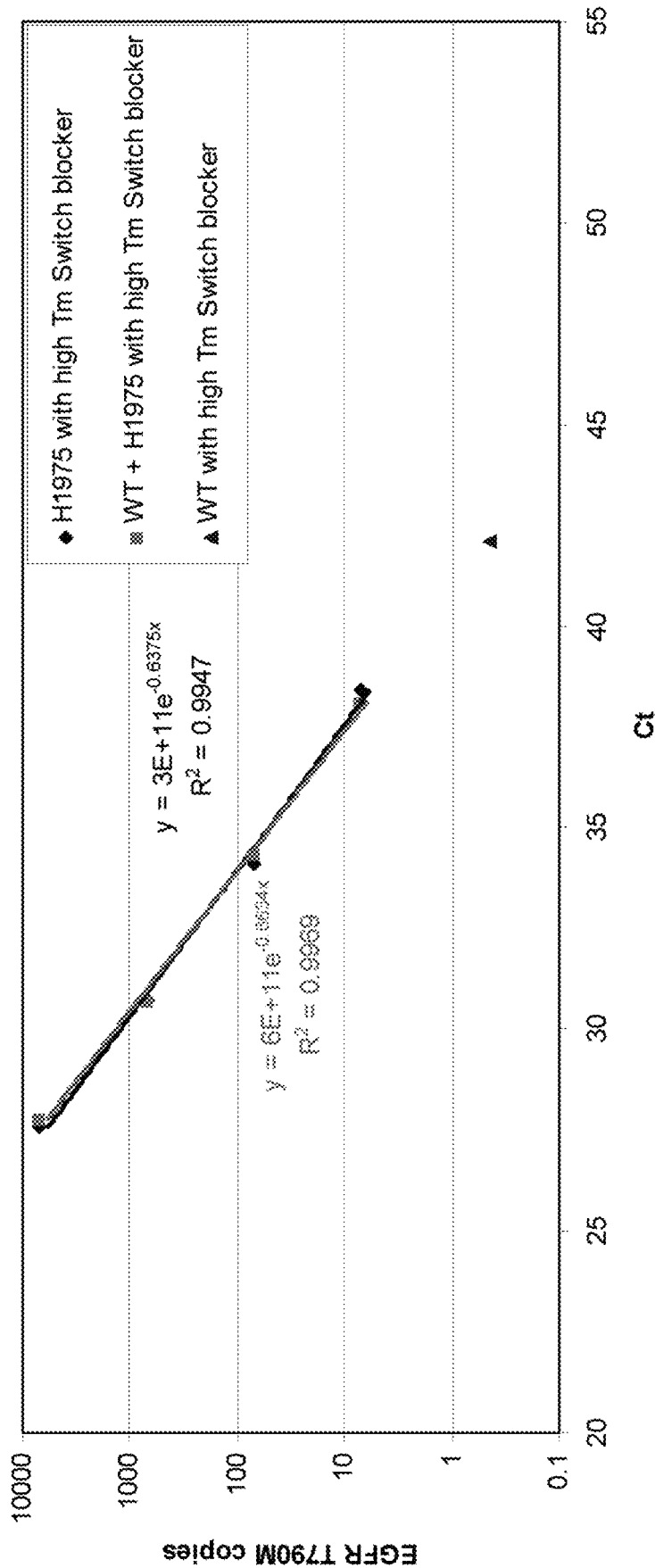
FIG. 30. T790M Selector assay with high Tm switch blocker and blunt forward primer.

Example 26. Detection of T790M Using the High Tm Switch Blocker and a Blunt Forward Primer To demonstrate the limited effect of the presence of wild-type on the detection of a T790M mutation, an assay was performed with and without the presence of wild-type. Increasing amounts of H1975 genomic DNA (0.05 ng, 0.5 ng, 5 ng or 50 ng, which corresponds to 7, 70, 700 and 7000 copies T790M respectively) were used in the Selector Assay in the presence or absence of about 14000 copies of wild-type EGFR and high Tm switch blocker. The amplification data of the average of triplicate reactions are plotted and used for the trendline in the graph (see FIG. 30).
Results:
Increasing amounts of H1975 genomic DNA (equivalent from 7 to up to about 7000 copies of T790M) were used in the Selector Assay in the presence of high Tm switch blocker and about 14,000 copies of wild-type EGFR (added in the form of 50 ng LnCAP genomic DNA). As can be seen from the amplification data graphs, the presence of the wild-type control DNA minimally affects the amplification of the T790M mutant (compare H1975 to WT+H1975 graph).
Methods:
Selector Assay reactions with high Tm switch blocker were done in a 10 µl volume with the following components: 0.3 µM blunt forward primer (5'-C*A*CCTCCACCGTGCA*R*C*T-3' (SEQ ID NO: 43); R=A/G; * indicates phosphorothioate), 0.3 µM reverse primer (5'-T*G*AGCAGGTACTGGGA-GCCAATATTGTCTTTGTGT*T*C*C-3' (SEQ ID NO: 41); *indicates phosphorothioate, 0.5 µM high Tm switch blocker (5'-BHQ1*2'OMe(C*A*U)cacgcagBBBBTGC (FAM)CCTTCGGCTGCCTCCTGGACTATGT C-2'OMe (C*G*G)*C3-3' (SEQ ID NO: 42); *indicates phosphoro-thioate; B indicates 5-nitroindole, lower case indicates 2' Fluoro Ribonucleoside, C3 indicates three carbon spacer), 3 mM MgCl$_2$, 0.4 mM dNTP's, 0.2 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 96-well plate and PCR cycling was done in an ABI 7900HT instrument with the following cycling conditions: 95° C. for 5 min, 55 cycles of 98° C. for 20 s, 71° C. for 10 s, 50° C. for 8 sec, 66° C. for 1 min, followed by a dissociation curve analysis (95° C. for 1 min, 40° C. for 30 s then with a 1% ramp to 95° C.). Detection of amplification product was done by monitoring 6-FAM fluorescence during the 50° C. cycle step and for melt curve analysis during the 40° C. to 95° C. ramp.

Figure 31:
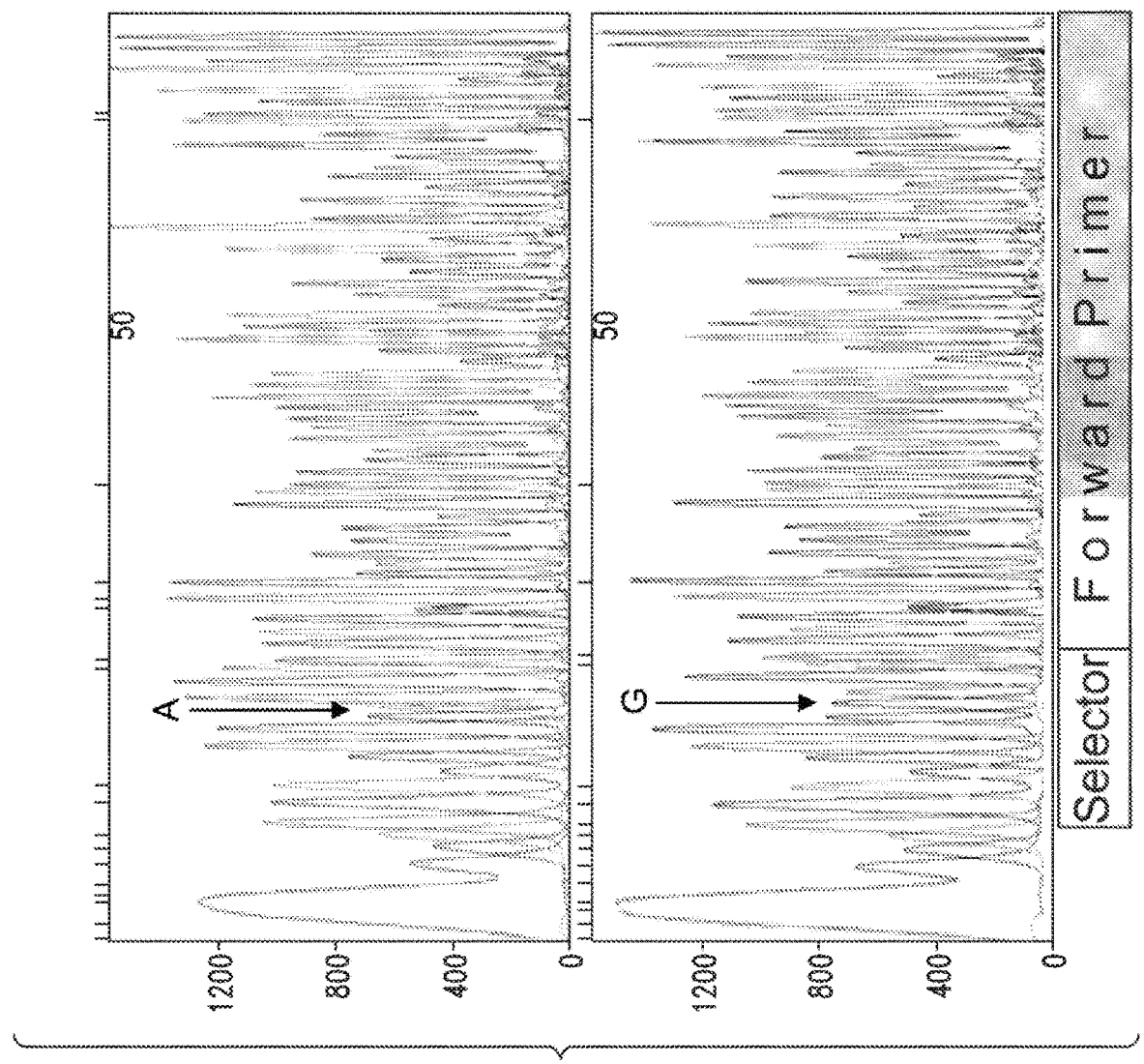
FIG. 31. Sanger sequencing of T790M Selector assay products grafted with Ion torrent adapters.

Example 27. Demonstration of Combining Selector Amplification with Sequencing Reactions To demonstrate the utility of Selector amplification in combination with sequencing, a Selector amplification reaction was followed by a tailing reaction to graft in the adapters for Ion Torrent sequencing. Selector assay reactions of a wild-type/mutant mixture (14000 copies wild-type/7 copies T790M mutant) were done in the presence (upper panel) or absence (lower panel) of Selector blocker and were used in a subsequent amplification reaction with adapter primers for Ion Torrent sequencing (see FIG. 31). Sanger sequencing was performed to verify the ability to detect T790M mutation in excess of wild-type sequences and incorporation of adapter sequences in upper panel (see FIG. 31). The nucleotide specific for the T790M mutation is indicated by an arrow (wild-type: G, T790M: A). The location of the Selector and forward primer sequences containing the Ion Torrent barcode and adapter sequences is shown below the chromatograms.

Results:

A Selector assay of an approximately 2000:1 wild-type/T790M mixture was done in the presence (upper panel) or absence (lower panel) of a Selector blocker. The amplified products were used in a second amplification reaction with forward and reverse primer containing Ion Torrent adapter sequences. Sanger sequencing in the upper panel using an internal sequencing primer indicates that the product of the reaction contain the adapter sequences in the forward primer. Also, it can be seen that the reaction product in the presence of the Selector is the T790M mutant (upper panel) whereas in the absence of the Selector it is wild-type (lower panel). Based on the approximately 10% resolution of Sanger sequencing for detecting rare alleles, this indicates that the T790M mutation selectively amplified by >20,000 fold.

Methods:

Selector assay reactions were done exactly as described in Example 6. 50 ng LnCAP was used as a wild-type template (corresponds to about 14000 copies EGFR). The PCR products were purified with the QIAquick PCR Purification Kit (Qiagen) and equal amounts (about 14 ng) of Selector reactions were used in a second amplification reaction. The second amplification reaction was done in a 10 µl volume with 0.3 µM forward primer adapter A (5'-C*C*ATCTCATCCCTGCGTGTCTCCGACTCAGCTA-AGGTAACGATC ACCGTGCAR*C*T*C-3' (SEQ ID NO: 44); R=A/G; * indicates phosphorothioate), 0.3 reverse primer adapter P (5'-C*C*TCT-CTATGGGCAGTCGGT-GATTGTTCCCGGACATAGT*
C*C*A-3' (SEQ ID NO: 45); *indicates phosphorothioate), 0.6 µM Reporter 4 (as described in Example 6), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 15 cycles of 98° C. for 20 s, 61° C. for 30 s, 52° C. for 1 min, 69° C. for 15 s followed by a dissociation curve analysis (95° C. for 1 min, 40° C. for 30 s then with a 1% ramp to 95° C.). Detection of amplification product was done by monitoring 6-FAM fluorescence during the 52° C. cycle step and for melt curve analysis during the 40° C. to 95° C. ramp. The products of the second PCR were purified with the QIAquick PCR Purification Kit. About 70 ng of purified PCR product was mixed with 0.1 µM sequencing primer (CATAGCAGCTGTTTTCCCAGTCATCGACGTT-GTAGTCCA GGAGGCAGCCGAA (SEQ ID NO: 14)) and submitted to Retrogen Inc. for Sanger sequencing. The sequencing results were visualized using dnaTools explorer (dnaTools, Inc.).

Example 28. Demonstration of Combining High Tm Switch Blocker Amplification with Sequencing Reactions To demonstrate the utility of the high Tm switch blocker amplification in combination with sequencing, a high Tm switch blocker amplification reaction was followed by a tailing reaction to graft in the adapters for Ion Torrent sequencing. Selector assay reactions of a wild-type/mutant mixture (14000 copies wild-type/7 copies T790M mutant) were done in the presence (upper panel) or absence (lower panel) of switch blocker and were used in a subsequent amplification reaction with adapter primers for Ion torrent sequencing (see FIG. 32). Sanger sequencing was performed to verify the ability to detect T790M mutation in an excess of wild-type sequences and incorporation of adapter sequences in the upper panel. The nucleotide specific for the T790M mutation is indicated by an arrow (wild-type: G, T790M: A). The location of the high Tm switch blocker and forward primer sequences containing the Ion torrent barcode and adapter sequences is shown below the chromatograms.

A high Tm switch blocker assay of an approximately 2000:1 wild-type/T790M mixture was done in the presence (upper panel) or absence (lower panel) of the high Tm switch blocker. The amplified products were used in a second amplification reaction with forward and reverse primer containing Ion Torrent adapter sequences. Sanger sequencing of the upper strand using an internal sequencing primer indicates that the product of the reaction contain the adapter sequences in the forward primer. Also, it can be seen that the reaction product in the presence of the Selector is the T790M mutant whereas in the absence of the Selector it is wild-type. Based on the approximately 10% resolution of Sanger sequencing for detecting rare alleles, this indicates that the T790M mutation has been selectively amplified by >20,000 fold.

Selector assay reactions with the high Tm switch blocker were done as described for FIG. 32. 50 ng LnCAP was used as a wild-type template (corresponds to about 14000 copies EGFR). Selector reactions without switch blocker were done essentially the same way, but omitting switch blocker and including 0.6 µM Reporter 4 (as described in Example 6). The PCR products were purified with the QIAquick PCR Purification Kit (Qiagen) and equal amounts (about 17 ng) of Selector reactions were used in a second amplification reaction. The second amplification reaction was done in a 10 µl volume with 0.3 µM forward primer adapter A (5'-C*C*ATCTCATCCCTGCGTGTCTCCGACTCAGCT-AAGGTAACGATC ACCGTGCAR*C*T*C-3' (SEQ ID NO: 44); R=A/G; * indicates phosphorothioate), 0.3 µM reverse primer adapter P(5'-C*C*TCTC-TATGGGCA-GTCGGTGATTGTTCCCGGACATAGT*
C*C*A-3' (SEQ ID NO: 45); *indicates phosphorothioate), 0.6 µM Reporter 4 (as described in Example 6), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 384-well plate and PCR cycling was done in an ABI 7900HT instrument with the following cycling conditions: 95° C. for 5 min, 15 cycles of 98° C. for 20 s, 61° C. for 30 s, 52° C. for 1 min, 69° C. for 15 s followed by a dissociation curve analysis (95° C. for 1 min, 40° C. for 30 s then with a 1% ramp to 95° C.). Detection of amplification product was done by monitoring 6-FAM fluorescence during the 52° C. cycle step and for melt curve analysis during the 40° C. to 95° C. ramp. The products of the second PCR were purified with the QIAquick PCR Purification Kit. About 70 ng of purified PCR product was mixed with 0.1 µM sequencing primer (CATAGCAGCTGTTTTCCCAGTCATCGACGTT-GTAGTCCA GGAGGCAGCCGAA (SEQ ID NO: 14)) and submitted to Retrogen Inc. for Sanger sequencing. The sequencing results were visualized using dnaTools explorer (dnaTools, Inc.).

Figure 33A:
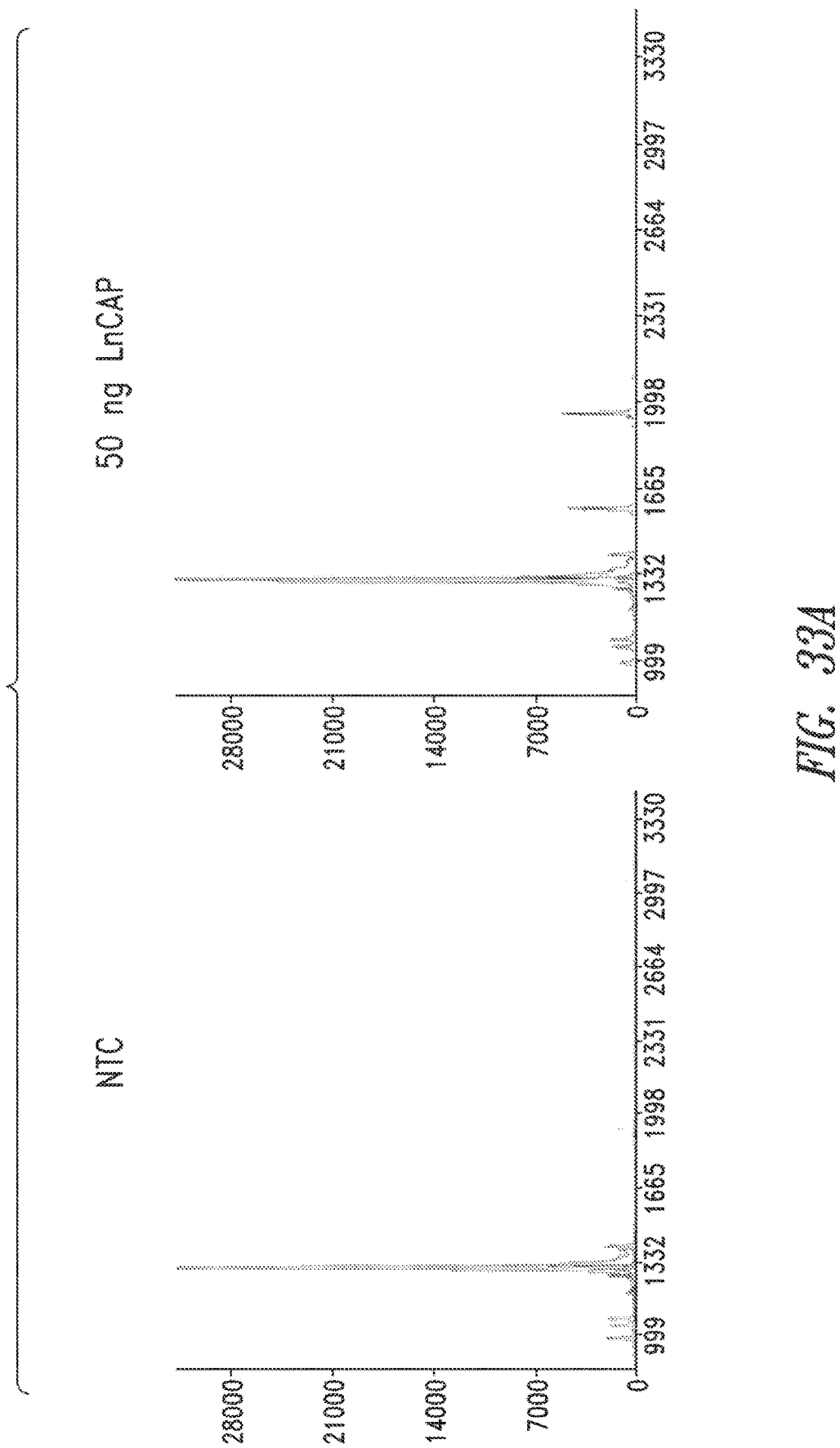
FIGS. 33A and 33B. Analysis of T790M Selector assay products by capillary electrophoresis.
Figure 33B:
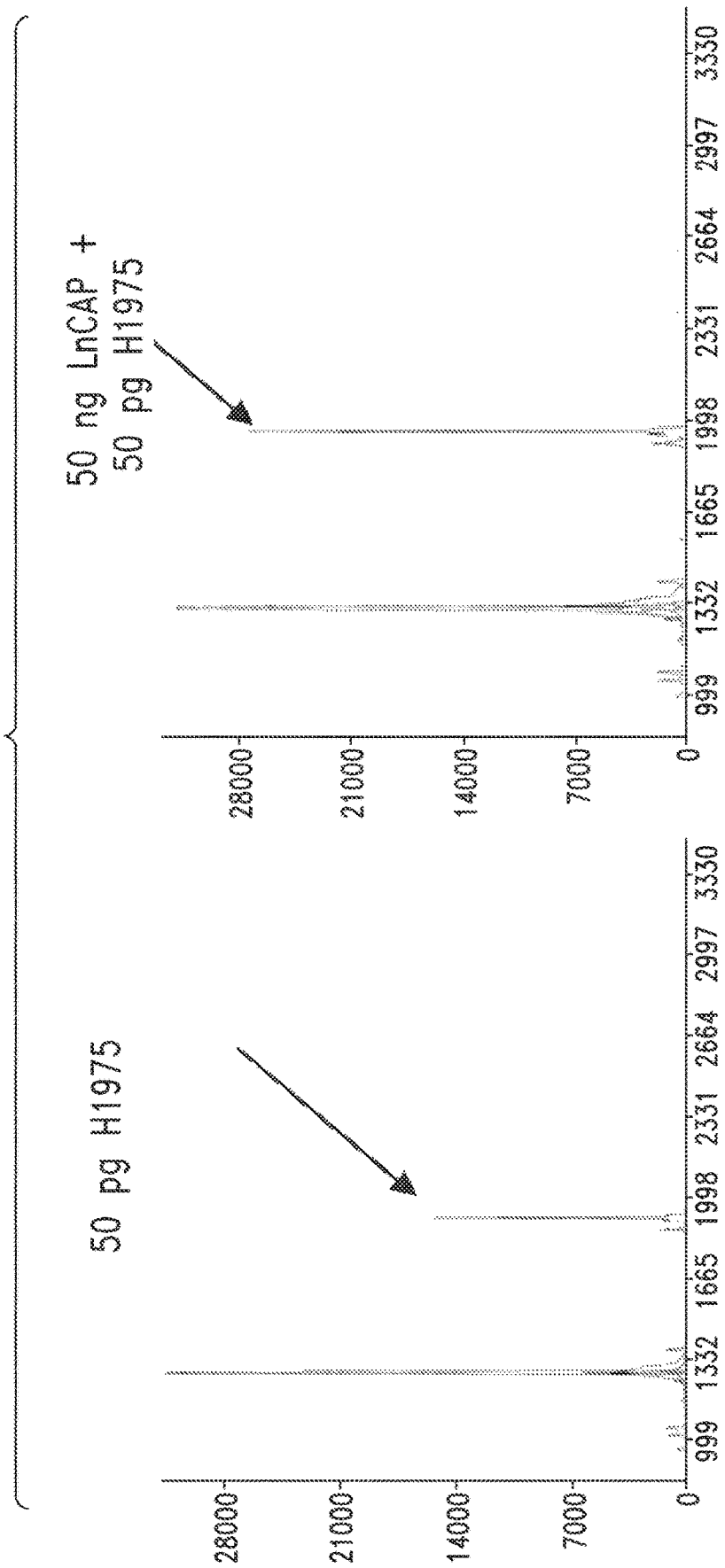
Figure 34A:
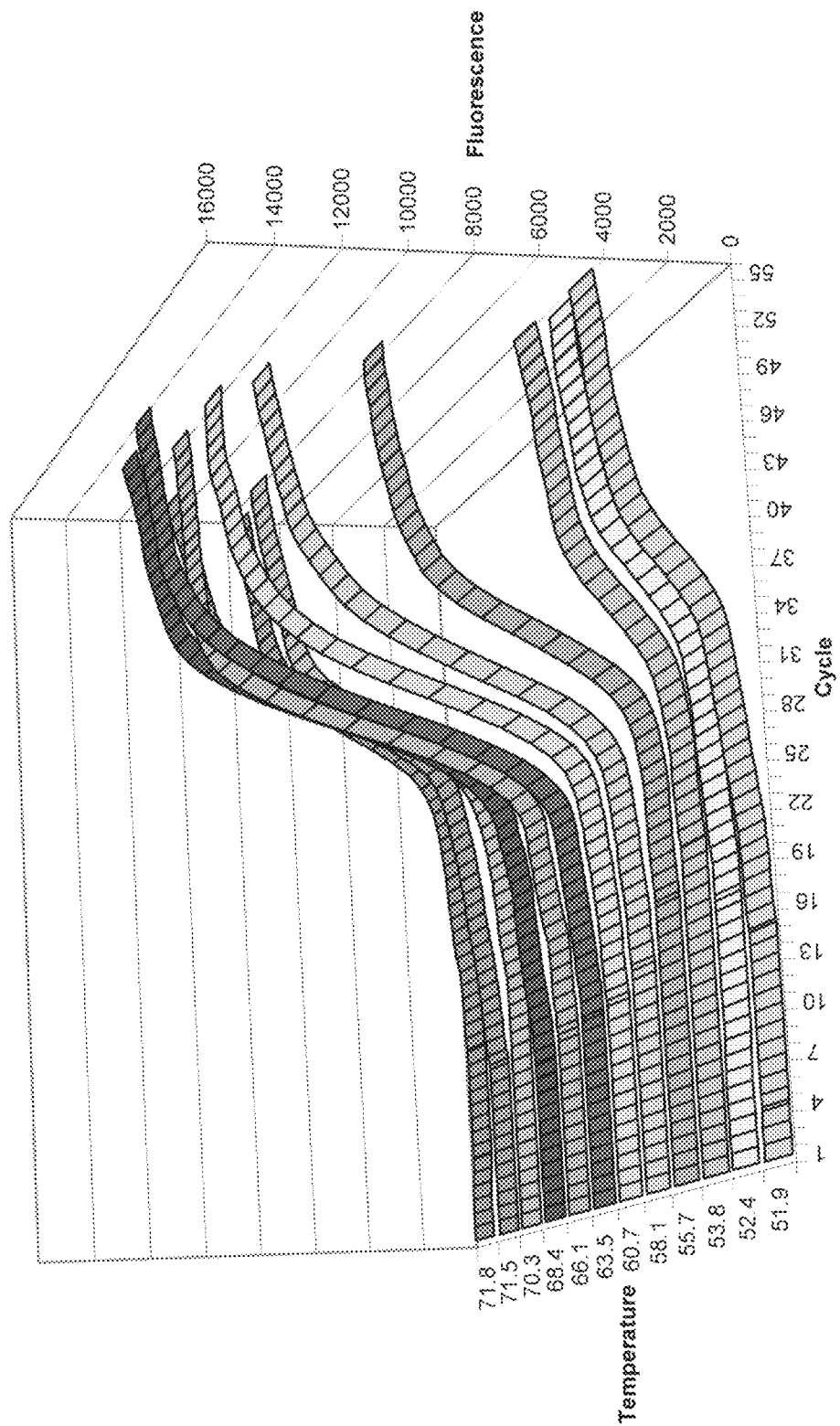
FIGS. 34A-34D. Selector assay Real-Time PCR results from a temperature gradient using high Tm switch blocker and either blunt forward primer (FIGS. 34A and 34B) or high Tm blunt forward primer (FIGS. 34C and 34D) with mutant (H1975, FIGS. 34A and 34C) or wild-type (LnCAP, FIGS. 34B and 34D) template.
Figure 34B:
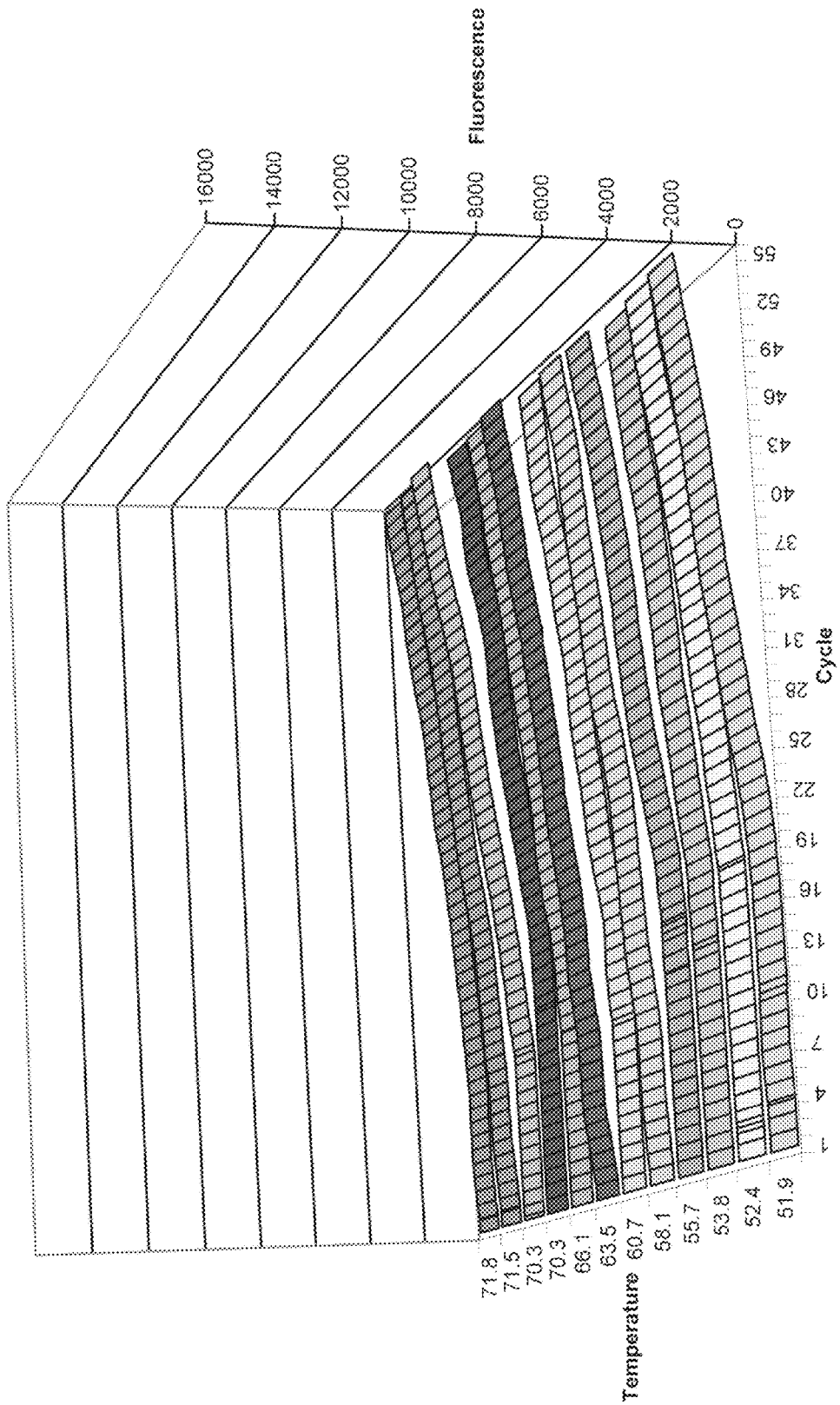
Figure 34C:
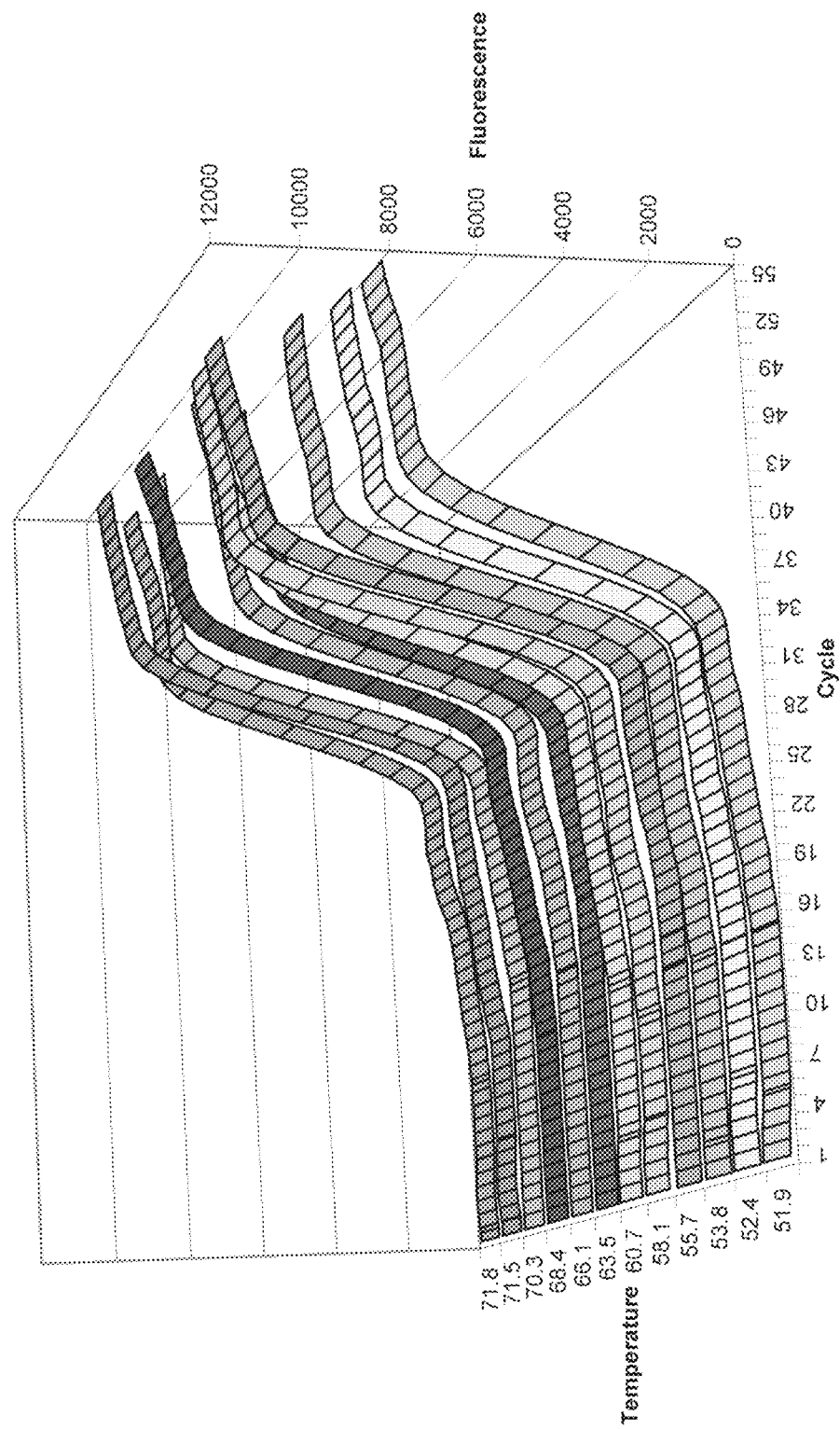
Figure 34D:
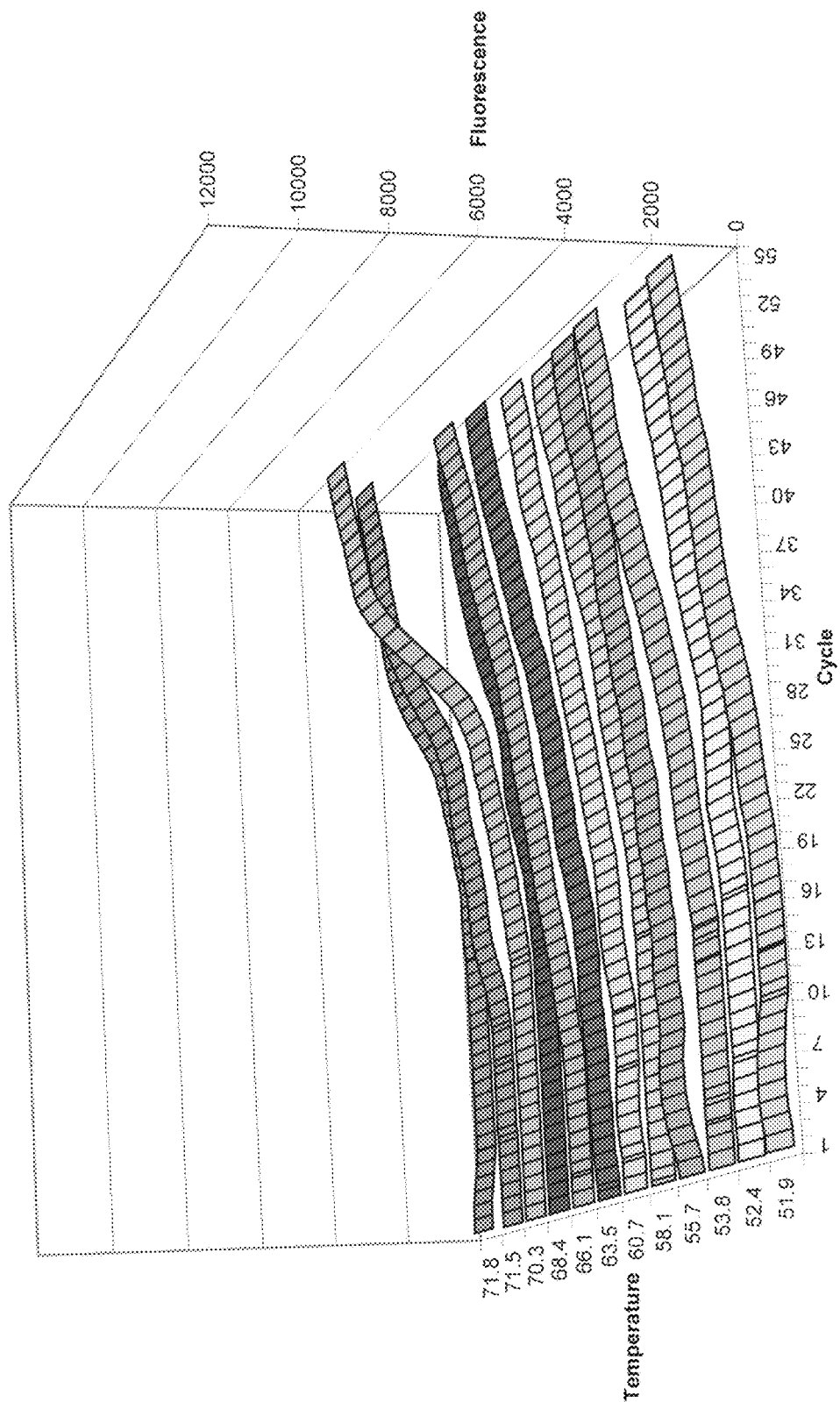

Example 29. Analysis of Amplification Products from a High Tm Switch Blocker Reaction To demonstrate the efficiency of a high Tm switch blocker amplification reaction, amplicons were labeled with a fluorescently tagged reverse primer and the amplification products analyzed. Selector Assay reactions were done with Cy3 labeled reverse primer and the products analyzed by capillary electrophoresis (see FIG. 33). The chromatograms show the Cy3 (in black), FAM (in blue) and GeneScan™-600 LIZ® standard (in yellow) fragments. The location of the full length PCR product (101 bp) is shown by an arrow. 50 ng LnCAP were used as a wild-type template (corresponds to 14000 copies) and 50 pg H1975 as T790M mutant template (corresponds to 7 copies). NTC indicates a no template control.

Results:

Selector assay was done using high Tm switch blocker with a blunt forward primer and a Cy3-labeled reverse primer. After the PCR the products were analyzed by capillary electrophoresis. The chromatograms indicate that reactions with 50 pg H1975 or a mixture of 50 pg H1975 with 50 ng LnCAP lead to a single product (with a minor smaller product fragment). The FAM peak (blue) corresponds to the switch blocker fragment.

Methods:

Selector assay reactions with high Tm switch blocker were done as described for FIG. 23 with the following modifications: the reverse primer used was Cy3 labeled at the 5' end (5'-Cy3*T*GAGCAGGTACTG-GGAGCCAATATTGTCTTTGTGT*T*C*C-3' (SEQ ID NO: 46), * indicates phosphorothioate) and cycling conditions were 95° C. for 5 min, 40 cycles of 98° C. for 20 s, 71° C. for 10 s, 66° C. for 1 min 30 s followed by a dissociation curve analysis (95° C. for 1 min, 40° C. for 30 s then with a 1% ramp to 95° C.). Detection of amplification product was done by monitoring 6-FAM fluorescence during the 66° C. cycle step and for melt curve analysis during the 40° C. to 95° C. ramp. Selector assay products were analysed by Retrogen Inc. by capillary electrophoresis on an ABI3730xl instrument. The .fsa files from Retrogen, Inc. were visualized using dnaTools explorer (dnaTools, Inc.).

Example 30. Demonstration of the Ability of the High Tm Switch Blocker to Discriminate a T790M Mutation from Wild-Type Over a Wide Temperature Range In order to demonstrate the ability of the switch portion of the high Tm switch blocker to further improve discrimination of mismatches, amplification reactions were carried out of a wide range of temperatures (see FIG. 34). High Tm switch blocker assay Real-Time PCR amplification results are shown of reactions using a temperature gradient from 52° C. to 72° C. The Selector assay was done with high Tm switch blocker, blunt forward primer (A, B) (used also in the previous experiments) or high Tm blunt forward primer (C, D) in combination with the same reverse primer.

Results:

The temperature gradient with the blunt primer (A, B) shows that the mutant template is amplified even at the starting temperature of about 52° C. and that the amplification efficiency reaches a maximum at about 64° C. Amplification can be detected up to the 72° C. In contrast, no amplification could be detected with the wild-type template (LnCAP), likely because the forward primer dissociates before the switch blocker dissociates and unblocks the wild-type template for amplification. Using a high Tm blunt forward primer shows that the wild-type is starting to get amplified at a temperature of about 70° C. This indicates that the low temperature melting of the switch portion in the presence of the mutation likely adds significantly to the discrimination of mutant and wild-type targets. When the switch is open in the presence of the mutant, the forward primer can extend to support amplification.

Methods:

Selector Assay reactions with high Tm switch blocker were done in a 10 µl volume with the following components: 0.3 µM blunt forward primer (5'-C*A*CCTCCACCGTGCA*R*C*T-3' (SEQ ID NO: 43); R=A/G; * indicates phosphorothioate) or 0.3 µM high Tm blunt forward primer (5'-TGCCTCACCTCCACCGTGCA*G*C*T-3' (SEQ ID NO: 26)) 0.3 µM reverse primer (5'-T*G*AGCAGGTACTGGGAGCCAATATTGTCT-TTGTGT*T*C*C-3' (SEQ ID NO: 41); *indicates phosphorothioate), 0.5 µM high Tm switch blocker 2 (5'-BHQ1*2'OMe(C*A*U)cacgcagBBBBTGC(FAM) CCTTCGGCTGCCTCCTGGACTATGT C-2'OMe (C*G*G)*C3-3' (SEQ ID NO: 42); *indicates phosphorothioate; B indicates 5-nitroindole, lower case indicates 2' Fluoro Ribonucleoside, C3 indicates three carbon spacer), 3 mM MgCl$_2$, 0.4 mM dNTP's, 0.4 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 96-well plate and PCR cycling was done in an Eppendorf Mastercycler®ep realplex instrument with the following cycling conditions: 95° C. for 5 min, 55 cycles of 98° C. for 20 s, 71° C. for 10 s, 50° C. for 8 sec, 52° C. to 72° C. gradient with 30 s at each temperature step, followed by a dissociation curve analysis (95° C. for 1 min, 40° C. for 30 s then with ramping to 95° C.). Detection of amplification product was done by monitoring 6-FAM fluorescence during the 50° C. cycle step and for melt curve analysis during the 40° C. to 95° C. ramp.

Example 31. Detection of T790M Using an Upstream Forward Primer and the High Tm Switch Blocker To demonstrate the ability of the high Tm switch blocker to serve as a steric blocker and to prevent the extension of a distant forward primer, a forward primer was tested that is approximately 50 nucleotides away from the high Tm switch blocker. Additionally, by comparing mutant to wild-type targets, the ability to sterically block amplification in targets differing by only a single nucleotide were determined (see FIG. 35).

Figure 35:
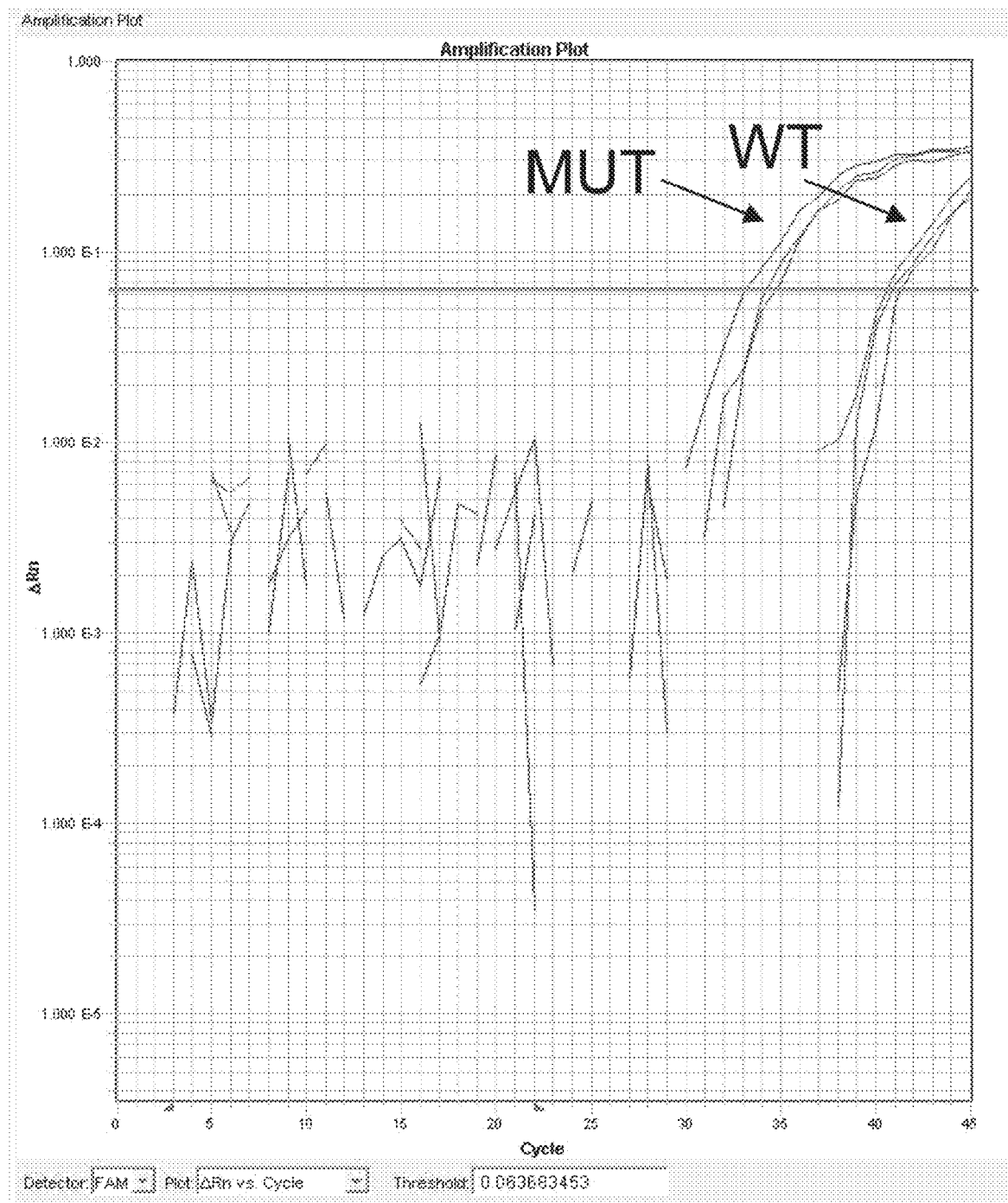
FIG. 35. Selector assay with upstream forward primer and high Tm switch blocker.

Results:

The T790M Selector assay was done with a forward primer which anneals 50 nucleotides upstream of the high Tm switch blocker annealing site. As shown in FIG. 35 the amplification of 140 copies of wild-type (500 pg LnCAP) have a Ct difference of about 7 compared to 70 copies of mutant (500 pg H1975). This indicates that under the tested conditions, where each Ct is equivalent to a 2-fold change in concentration, there is an approximately 256 fold reduction in wild-type amplification compared to mutant. This indicates that the high Tm selector blocker can be added to existing amplification systems or panels, regardless of primer location, to effectuate selective amplification of mutant sequences compared to wild-type, and to aid the enhanced detection of mutants.

Methods:

Selector Assay reactions with the high Tm switch blocker were done in a 10 µl volume with the following components: 0.3 µM forward primer (5'-G*T*GATGGCCAGCGTGGAC*A*A*C-3' (SEQ ID NO: 47); * indicates phosphorothioate), 0.3 µM reverse primer (5'-T*G*AGCAGGTACTG-GGAGCCAATATTGTCTTTGTGT*T*C*C-3' (SEQ ID NO: 41); *indicates phosphorothioate), 0.5 µM high Tm switch blocker #2 (5'-BHQ1*2'OMe(C*A*U)cacgcag-BBBBTGC(FAM)CCTTCGGCTGCCTCCTGGACTATGT C-2'OMe(C*G*G)*C3-3' (SEQ ID NO: 42); *indicates phosphorothioate; B indicates 5-nitroindole, lower case indicates 2' Fluoro Ribonucleoside, C3 indicates three carbon spacer), 3 mM MgCl$_2$, 0.5 mM spermidine, 0.4 mM dNTP's, 0.2 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 96-well plate and PCR cycling was done in an ABI 7900HT instrument with the following cycling conditions: 95° C. for 5 min, 55 cycles of 98° C. for 20 s, 74° C. for 10 s, 50° C. for 8 sec, 56° C. for 15 s, followed by a dissociation curve analysis (95° C. for 1 min, 40° C. for 30 s then with a 1% ramp to 95° C.). Detection of amplification product was done by monitoring 6-FAM fluorescence during the 50° C. cycle step and for melt curve analysis during the 40° C. to 95° C. ramp.

Example 32. Detection of T790M Using a Temperature Gradient with an Upstream Forward Primer and the High Tm Switch Blocker To demonstrate the ability of a high Tm switch blocker to block the amplification of wild-type without blocking amplification of mutant, when using a forward primer well upstream of the high Tm switch blocker, assays were carried out with a forward primer 50 nucleotide upstream of the high Tm switch blocker. Assays were also carried out over a wide range of temperatures.

Figure 36A:
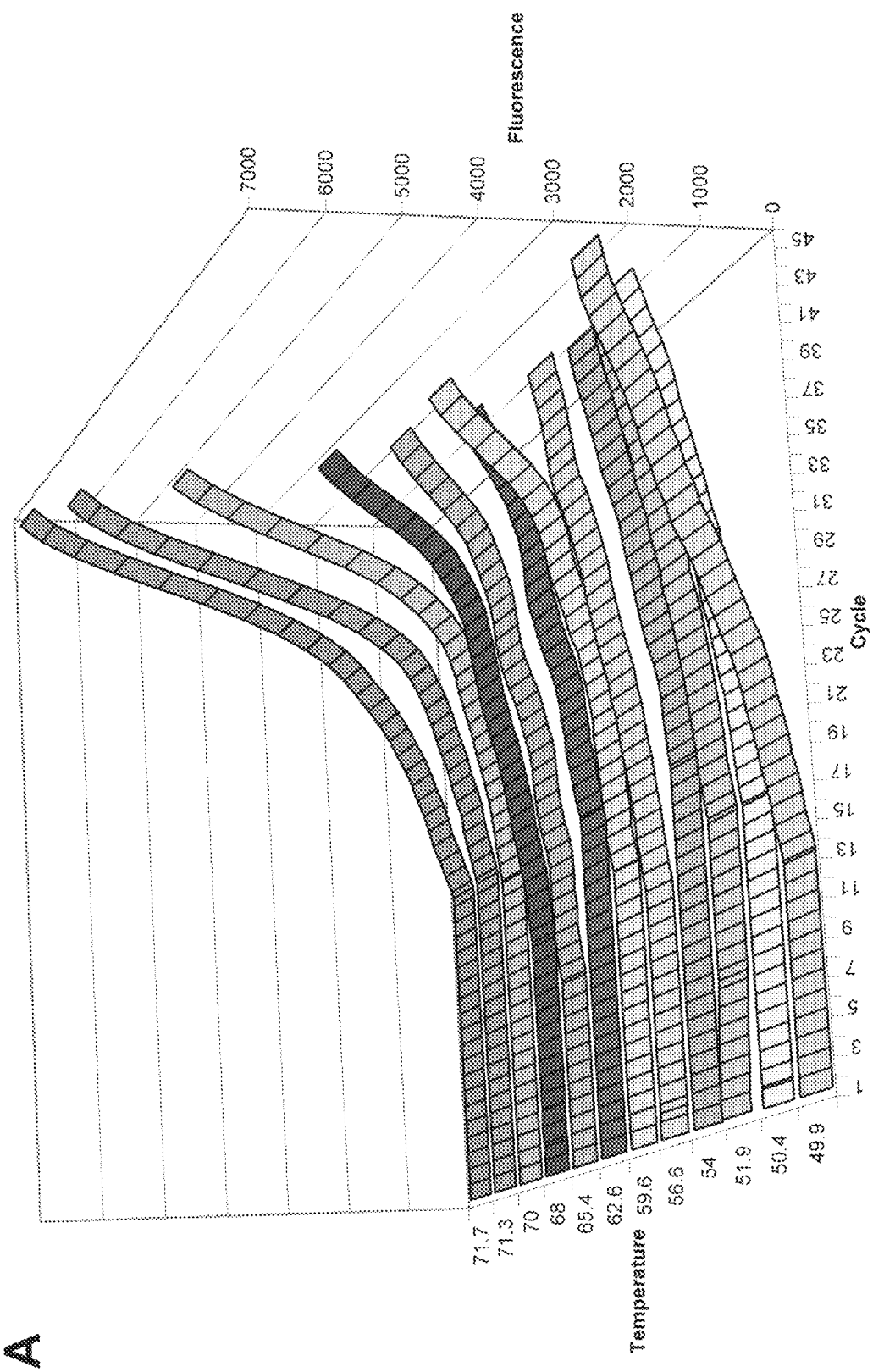
FIGS. 36A and 36B. Selector assay using a temperature gradient with upstream forward primer and high Tm switch blocker.
Figure 36B:
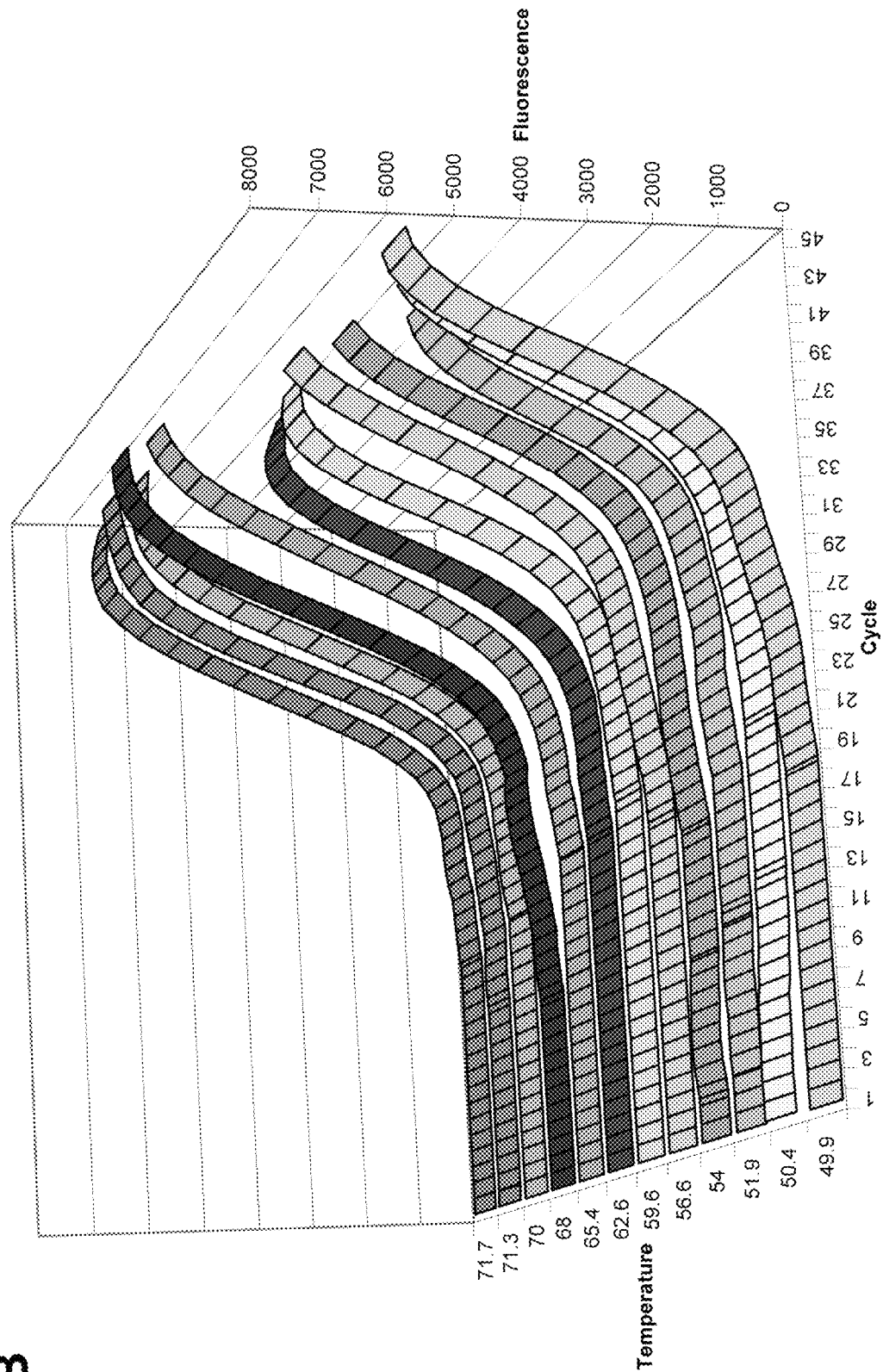

Results:

Assays were done using a temperature gradient from 50° C. to 72° C. on the Eppendorf Mastercycler®ep realplex instrument which has a higher ramp rate than the Life Technologies ABI7900HT instrument (4° C. versus 1.6° C.). FIG. 36 shows that the amplification of 140 copies of wild-type (500 pg LnCAP) (A) is completely inhibited at 56.6° C., whereas 70 copies of T790M mutant (500 pg H1975) (B) show a Ct of about 37. This demonstrates a delta Ct of mutant verses wild-type of at least 8 (there is no apparent emergence of wild-type at 45 Ct), which at a minimum, corresponds to a preferential amplification of mutant of >500 fold compared to wild-type. This further supports the findings in Example 30, and at the same time, demonstrates that the discrimination can be achieved over a temperature range of 12° C. to 15° C. or more, even when the forward primers are well removed from the high Tm switch blocker.

Methods:

Selector Assay reactions with high Tm switch blocker were done in a 10 µl volume with the following components: 0.3 µM upstream forward primer (5'-G*T*GATGGCCAGCGTGGAC*A*A*C-3' (SEQ ID NO: 47); * indicates phosphorothioate), 0.3 µM reverse primer (5'-T*G*AGCAGGTACTGGGAGCCAATA-TTGTCTTTGTGT*T*C*C-3' (SEQ ID NO: 41); *indicates phosphorothioate), 0.5 µM high Tm switch blocker 2 (5'-BHQ1*2'OMe(C*A*U)cacgcagBBBBTGC(FAM)CCT-TCGGCTGCCTCCTGGACTATGT C-2'OMe(C*G*G) *C3-3' (SEQ ID NO: 42); *indicates phosphorothioate; B indicates 5-nitroindole, lower case indicates 2' Fluoro Ribonucleoside, C3 indicates three carbon spacer), 3 mM MgCl$_2$, 0.5 mM spermidine, 0.4 mM dNTP's, 0.2 U Kapa HiFi Hotstart DNA Polymerase (Kapa Biosystems, Cat. No. KK2101), 1×HiFi buffer, 0.2 µl ROX reference dye (LifeTechnologies, Cat. No. 12223-012). PCR reactions were loaded on a 96-well plate and PCR cycling was done in an Eppendorf Mastercycler®ep realplex instrument with the following cycling conditions: 95° C. for 5 min, 45 cycles of 98° C. for 20 s, 74° C. for 10 s, 50° C. for 8 sec, 50° C. to 72° C. gradient with 15 s at each temperature step, followed by a dissociation curve analysis (95° C. for 1 min, 40° C. for 30 s then with ramping to 95° C.). Detection of amplification product was done by monitoring 6-FAM fluorescence during the 50° C. cycle step and for melt curve analysis during the 40° C. to 95° C. ramp.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A primer-switch comprising a forward primer linked or conjugated covalently or non-covalently to a selector blocker, wherein the forward primer and selector blocker are not linked or conjugated at the 3' end of the forward primer wherein the forward primer and selector blocker each comprise a sequence complementary to a sequence in a target region of a nucleic acid, wherein the target region comprises a region to which both the forward primer and the selector blocker are complementary, wherein the selector blocker is complementary to a sequence 5' of the sequence to which the forward primer is complementary or that overlaps with the sequence to which the forward primer is complementary, wherein the selector blocker is non-extendable, wherein the primer-switch is not attached to a solid support, and wherein (i) the selector blocker portion of the primer-switch functions as a steric blocker when bound to its target sequence, preventing extension of the forward primer, or (ii) the selector blocker portion of the primer-switch is not capable of binding tightly to the target region such that the forward primer can extend.

2. The primer-switch of claim 1, wherein the forward primer and selector blocker are linked non-covalently or conjugated via a crosslinker or S18 spacer.

3. The primer-switch of claim 1, wherein the selector blocker comprises a sequence complementary to a sequence in the target region in the absence of a nucleic acid variant.

4. The primer-switch of claim 1, wherein the forward primer and selector blocker target sequences that overlap by 5, 10, 15, or more nucleotides.

5. The primer-switch of claim 1, wherein the target region comprises one or more positions at which a nucleic acid variant may be present or absent, and wherein the forward primer and the selector blocker each have a sequence complementary to the same target region except that they differ from each other at one or more locations where the nucleic acid variant occurs.

6. The primer-switch of claim 5, wherein the forward primer has a sequence fully complementary to the target region when the nucleic acid variant is present and the selector blocker has a sequence fully complementary to the target region when the nucleic acid variant is absent.

7. The primer-switch of claim 5, wherein the forward primer has a sequence fully complementary to the target region when the nucleic acid variant is absent and the selector blocker has a sequence fully complementary to the target region when the nucleic acid variant is present.

8. The primer-switch of claim 1, wherein the primer-switch is generated by synthesizing the forward primer with 3' to 5' chemistry, inserting at least one S18 spacer, and reversing strand direction to synthesize the selector blocker with 5' to 3' chemistry.

9. The primer-switch of claim 1, wherein the primer-switch further comprises a detectable entity.

10. The primer-switch of claim 9, wherein the detectable entity is selected from the group consisting of fluorescent labels, chemiluminescent labels, and FRET pairs.

11. The primer-switch of claim 1, wherein the selector blocker has a higher Tm than the forward primer.

12. The primer-switch of claim 1, wherein the selector blocker has a lower Tm than the forward primer.

13. A method for detecting the presence or absence of a nucleic acid variant in a target region comprising:
amplifying the target region in the presence of the primer-switch of claim 3 and a reverse primer, wherein amplification of the target region is indicative of the presence of the nucleic acid variant in the target region, and wherein the absence of amplification is indicative of the absence of the nucleic acid variant in the target region.

14. The method of claim 13, wherein the nucleic acid variant includes a deletion, mutation, or insertion.

15. The method of claim 13, wherein the amplification is performed in the presence of an enzyme possessing 3' exonuclease repair activity.

16. A composition comprising: (i) a reverse primer, and (ii) a primer-switch comprising a forward primer linked or conjugated covalently or non-covalently to a selector blocker, wherein the forward primer and selector blocker are not linked or conjugated at the 3' end of the forward primer, wherein the forward primer and selector blocker each comprise a sequence complementary to a sequence in a target region of a nucleic acid, wherein the target region comprises a region to which both the forward primer and the selector blocker are complementary, wherein the selector blocker is complementary to a sequence 5' of the sequence to which the forward primer is complementary or that overlaps with the sequence to which the forward primer is complementary, wherein the selector blocker is non-extendable, and wherein (i) the selector blocker portion of the primer-switch functions as a steric blocker when bound to its target sequence, preventing extension of the forward primer, or (ii) the selector blocker portion of the primer-switch is not capable of binding tightly to the target region such that the forward primer can extend.

* * * * *

SEQUENCE LISTING

```
<160> NUMBER OF SEQ ID NOS: 47

<210> SEQ ID NO 1
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (13)..(16)
<223> OTHER INFORMATION: may be joined by phosphorothioate bonds

<400> SEQUENCE: 1
```

```
accgtgcarc tcatca                                              16

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
gcaggtactg ggagcc                                              16

<210> SEQ ID NO 3
<211> LENGTH: 15
<212> TYPE: DNA
<213> ORGANISM: Artificial Sequence
<220> FEATURE:
<223> OTHER INFORMATION: Selector A Oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(1)
<223> OTHER INFORMATION: 2'-OMe-uridine
<220> FEATURE:
<221> NAME/KEY: modified_base
<222> LOCATION: (2)..(2)
<223> OTHER INFORMATION: 2'-OMe-cytosine
<220> FEATURE:
<221> NAME/KEY: modified_base
<222> LOCATION: (3)..(15)
<223> OTHER INFORMATION: Bases are 2'-fluoro ribonucleosides
<220> FEATURE:
<221> NAME/KEY: misc_feature
<222> LOCATION: (13)..(15)
<223> OTHER INFORMATION: may be joined by phosphorothioate bonds
<220> FEATURE:
<221> NAME/KEY: misc_feature
<222> LOCATION: (15)..(15)
<223> OTHER INFORMATION: may be labeled with a 6-Fam moiety

<400> SEQUENCE: 3
ucaucacgca gcuca                                               15

<210> SEQ ID NO 4
<211> LENGTH: 19
<212> TYPE: DNA
<213> ORGANISM: Artificial Sequence
<220> FEATURE:
<223> OTHER INFORMATION: Reporter A Oligonucleotide
<220> FEATURE:
<221> NAME/KEY: misc_feature
<222> LOCATION: (1)..(1)
<223> OTHER INFORMATION: may be labeled with a LC Red 640 moiety and two
      3 carbon spacer moieties
<220> FEATURE:
<221> NAME/KEY: misc_feature
<222> LOCATION: (1)..(2)
<223> OTHER INFORMATION: may be joined by phosphorothioate bonds
<220> FEATURE:
<221> NAME/KEY: misc_feature
<222> LOCATION: (17)..(19)
<223> OTHER INFORMATION: may be joined by phosphorothioate bonds
<220> FEATURE:
<221> NAME/KEY: misc_feature
<222> LOCATION: (19)..(19)
<223> OTHER INFORMATION: may have a 3 carbon spacer moiety attached

<400> SEQUENCE: 4
tgcccttcgg ctgcctcct                                           19
```

<210> SEQ ID NO 5
<211> LENGTH: 15
<212> TYPE: DNA
<213> ORGANISM: Artificial Sequence
<220> FEATURE:
<223> OTHER INFORMATION: Reporter B oligonucleotide
<220> FEATURE:
<221> NAME/KEY: modified_base
<222> LOCATION: (1)..(1)
<223> OTHER INFORMATION: 2-OMe-uridine
<220> FEATURE:
<221> NAME/KEY: modified_base
<222> LOCATION: (2)..(2)
<223> OTHER INFORMATION: 2-OMe-guanosine
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (4)..(5)
<223> OTHER INFORMATION: may be joined by 7 carbon spacer moiety
<220> FEATURE:
<221> NAME/KEY: misc_feature
<222> LOCATION: (5)..(5)
<223> OTHER INFORMATION: may be labeled with an Alexa Fluor 546 moiety
<220> FEATURE:
<221> NAME/KEY: misc_feature
<222> LOCATION: (13)..(15)
<223> OTHER INFORMATION: may be joined by phosphorothioate bonds
<220> FEATURE:
<221> NAME/KEY: misc_feature
<222> LOCATION: (15)..(15)
<223> OTHER INFORMATION: may have a 3 carbon spacer moiety attached

<400> SEQUENCE: 5
cttcggctgc ctcct                                                    15

<210> SEQ ID NO 6
<211> LENGTH: 38
<212> TYPE: DNA
<213> ORGANISM: Artificial Sequence
<220> FEATURE:
<223> OTHER INFORMATION: Synthetic target WT

<400> SEQUENCE: 6
gctcatcacg cagctcatgc ccttcggctg cctcctgg                           38

<210> SEQ ID NO 7
<211> LENGTH: 38
<212> TYPE: DNA
<213> ORGANISM: Artificial Sequence
<220> FEATURE:
<223> OTHER INFORMATION: Synthetic target MUT

<400> SEQUENCE: 7
gctcatcatg cagctcatgc ccttcggctg cctcctgg                           38

<210> SEQ ID NO 8
<211> LENGTH: 28
<212> TYPE: DNA
<213> ORGANISM: Artificial Sequence
<220> FEATURE:
<223> OTHER INFORMATION: Reporter 1 oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(5)

<223> OTHER INFORMATION: Bases are 2'-fluoro ribonucleosides
<220> FEATURE:
<221> NAME/KEY: misc_feature
<222> LOCATION: (5)..(6)
<223> OTHER INFORMATION: may be joined by a 7 carbon spacer moiety
<220> FEATURE:
<221> NAME/KEY: misc_feature
<222> LOCATION: (6)..(6)
<223> OTHER INFORMATION: may be labeled with an 6-FAM moiety
<220> FEATURE:
<221> NAME/KEY: misc_feature
<222> LOCATION: (26)..(28)
<223> OTHER INFORMATION: may be joined by phosphorothioate bonds
<220> FEATURE:
<221> NAME/KEY: misc_feature
<222> LOCATION: (28)..(28)
<223> OTHER INFORMATION: may have a 3 carbon spacer moiety attached
<220> FEATURE:
<221> NAME/KEY: misc_feature
<222> LOCATION: (28)..(28)
<223> OTHER INFORMATION: may have a Dabcyl moiety attached

<400> SEQUENCE: 8
ugcccttcgg ctgcctcctg gagccgaa                                       28

<210> SEQ ID NO 9
<211> LENGTH: 34
<212> TYPE: DNA
<213> ORGANISM: Artificial Sequence
<220> FEATURE:
<223> OTHER INFORMATION: Reporte 2 oligonucleotide
<220> FEATURE:
<221> NAME/KEY: misc_feature
<222> LOCATION: (1)..(1)
<223> OTHER INFORMATION: may have a 6-FAM moiety attached
<220> FEATURE:
<221> NAME/KEY: misc_feature
<222> LOCATION: (1)..(1)
<223> OTHER INFORMATION: may have a 3 carbon spacer moiety attached
<220> FEATURE:
<221> NAME/KEY: misc_feature
<222> LOCATION: (1)..(2)
<223> OTHER INFORMATION: may be joined by phosphorothioate bonds
<220> FEATURE:
<221> NAME/KEY: misc_feature
<222> LOCATION: (32)..(34)
<223> OTHER INFORMATION: may be joined by phosphorothioate bonds
<220> FEATURE:
<221> NAME/KEY: misc_feature
<222> LOCATION: (34)..(34)
<223> OTHER INFORMATION: may have a 3 carbon spacer moiety attached
<220> FEATURE:
<221> NAME/KEY: misc_feature
<222> LOCATION: (34)..(34)
<223> OTHER INFORMATION: may have a Dabcyl moiety attached

<400> SEQUENCE: 9
ttcggctgcc tcctggacta tgtccggagc cgaa                                34

<210> SEQ ID NO 10
<211> LENGTH: 13
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (10)..(13)
<223> OTHER INFORMATION: may be joined by phosphorothioate bonds

<400> SEQUENCE: 10
caccgtgcar ctc                                                      13

<210> SEQ ID NO 11
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (15)..(18)
<223> OTHER INFORMATION: may be joined by phosphorothioate bonds

<400> SEQUENCE: 11
tgtgttcccg gacatagt                                                 18

<210> SEQ ID NO 12
<211> LENGTH: 13
<212> TYPE: DNA
<213> ORGANISM: Artificial Sequence
<220> FEATURE:
<223> OTHER INFORMATION: Selector 6 oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(1)
<223> OTHER INFORMATION: 2-OMe-adenosine
<220> FEATURE:
<221> NAME/KEY: modified_base
<222> LOCATION: (2)..(2)
<223> OTHER INFORMATION: 2-OMe-uridine
<220> FEATURE:
<221> NAME/KEY: modified_base
<222> LOCATION: (3)..(13)
<223> OTHER INFORMATION: Bases are 2'-fluoro ribonucleosides
<220> FEATURE:
<221> NAME/KEY: misc_feature
<222> LOCATION: (11)..(13)
<223> OTHER INFORMATION: may be joined by phosphorothioate bonds
<220> FEATURE:
<221> NAME/KEY: misc_feature
<222> LOCATION: (13)..(13)
<223> OTHER INFORMATION: may have a LC Red 640 moiety attached

<400> SEQUENCE: 12
aucacgcagc uca                                                      13

<210> SEQ ID NO 13
<211> LENGTH: 28
<212> TYPE: DNA
<213> ORGANISM: Artificial Sequence
<220> FEATURE:
<223> OTHER INFORMATION: Reporter 4 oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(5)
<223> OTHER INFORMATION: Bases are 2'-fluoro-ribonucleoside
<220> FEATURE:
<221> NAME/KEY: misc_feature
<222> LOCATION: (5)..(6)
<223> OTHER INFORMATION: may be joined by a 7 carbon spacer moiety
<220> FEATURE:

<220> FEATURE:
<221> NAME/KEY: misc_feature
<222> LOCATION: (6)..(6)
<223> OTHER INFORMATION: may be labeled with an 6-FAM moiety
<220> FEATURE:
<221> NAME/KEY: modified_base
<222> LOCATION: (15)..(19)
<223> OTHER INFORMATION: Bases are 2'-fluoro-ribonucleoside
<220> FEATURE:
<221> NAME/KEY: misc_feature
<222> LOCATION: (26)..(28)
<223> OTHER INFORMATION: may be joined by phosphorothioate bonds
<220> FEATURE:
<221> NAME/KEY: misc_feature
<222> LOCATION: (28)..(28)
<223> OTHER INFORMATION: may have a Dabcyl moiety attached

<400> SEQUENCE: 13
ugcccuucgg ctgccuccug gagccgaa                                              28

<210> SEQ ID NO 14
<211> LENGTH: 52
<212> TYPE: DNA
<213> ORGANISM: Artificial Sequence
<220> FEATURE:
<223> OTHER INFORMATION: Primer

<400> SEQUENCE: 14
catagcagct gttttcccag tcatcgacgt tgtagtccag gaggcagccg aa                   52

<210> SEQ ID NO 15
<211> LENGTH: 14
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (11)..(14)
<223> OTHER INFORMATION: may be joined by phosphorothioate bonds

<400> SEQUENCE: 15
cgtgcarctc atca                                                            14

<210> SEQ ID NO 16
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (18)..(21)
<223> OTHER INFORMATION: may be joined by phosphorothioate bonds

<400> SEQUENCE: 16
atataaactt gtggtagttg g                                                    21

<210> SEQ ID NO 17
<211> LENGTH: 24
<212> TYPE: DNA
<213> ORGANISM: Artificial Sequence
<220> FEATURE:
<223> OTHER INFORMATION: Primer -continued

```
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (21)..(24)
<223> OTHER INFORMATION: may be joined by phosphorothioate bonds

<400> SEQUENCE: 17
gcatattaaa acaagattta cctc                                           24

<210> SEQ ID NO 18
<211> LENGTH: 13
<212> TYPE: DNA
<213> ORGANISM: Artificial Sequence
<220> FEATURE:
<223> OTHER INFORMATION: Selector oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(1)
<223> OTHER INFORMATION: 2'-OMe-adenosine
<220> FEATURE:
<221> NAME/KEY: modified_base
<222> LOCATION: (2)..(2)
<223> OTHER INFORMATION: 2'-OMe-guanosine
<220> FEATURE:
<221> NAME/KEY: modified_base
<222> LOCATION: (3)..(13)
<223> OTHER INFORMATION: Bases are 2'-fluoro-ribonucleosides
<220> FEATURE:
<221> NAME/KEY: misc_feature
<222> LOCATION: (11)..(13)
<223> OTHER INFORMATION: may be joined by phosphorothioate bonds
<220> FEATURE:
<221> NAME/KEY: misc_feature
<222> LOCATION: (28)..(28)
<223> OTHER INFORMATION: may have a LC Red 640 moiety attached

<400> SEQUENCE: 18 agcuggugge gua                                                       13

<210> SEQ ID NO 19
<211> LENGTH: 27
<212> TYPE: DNA
<213> ORGANISM: Artificial Sequence
<220> FEATURE:
<223> OTHER INFORMATION: Reporter oligonucleotide
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(5)
<223> OTHER INFORMATION: Bases are 2'-fluoro-ribonucleosides
<220> FEATURE:
<221> NAME/KEY: misc_feature
<222> LOCATION: (5)..(6)
<223> OTHER INFORMATION: may have a 6-Fam moiety attached
<220> FEATURE:
<221> NAME/KEY: modified_base
<222> LOCATION: (13)..(20)
<223> OTHER INFORMATION: Bases are 2'-fluoro-ribonucleosides
<220> FEATURE:
<221> NAME/KEY: misc_feature
<222> LOCATION: (25)..(27)
<223> OTHER INFORMATION: may be joined by phosphorothioate bonds
<220> FEATURE:
<221> NAME/KEY: misc_feature
<222> LOCATION: (27)..(27)
```

<223> OTHER INFORMATION: may have a Dabcyl moiety attached

<400> SEQUENCE: 19
ggcaagagtg ccuugacgau ggcactc        27

<210> SEQ ID NO 20
<211> LENGTH: 55
<212> TYPE: DNA
<213> ORGANISM: Artificial Sequence
<220> FEATURE:
<223> OTHER INFORMATION: Primer

<400> SEQUENCE: 20
catagcagct gttttcccag tcatcgacgt tgtacgtcca caaaatgatt ctgaa        55

<210> SEQ ID NO 21
<211> LENGTH: 80
<212> TYPE: DNA
<213> ORGANISM: Homo sapiens

<400> SEQUENCE: 21
ttgtgttccc ggacatagtc caggaggcag ccgaagggca tgagctgcgt gatgagctgc        60
acggtggagg tgaggcagat        80

<210> SEQ ID NO 22
<211> LENGTH: 80
<212> TYPE: DNA
<213> ORGANISM: Artificial Sequence
<220> FEATURE:
<223> OTHER INFORMATION: T790 mutant EGFR

<400> SEQUENCE: 22
ttgtgttccc ggacatagtc caggaggcag ccgaagggca tgagctgcat gatgagctgc        60
acggtggagg tgaggcagat        80

<210> SEQ ID NO 23
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: may have a spacer 18 (hexaethylene glycol)
      moiety attached

<400> SEQUENCE: 23
cctccaccgt gcagctcatc a        21

<210> SEQ ID NO 24
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: may have a spacer 18 (hexaethylene glycol)
      moiety attached

<400> SEQUENCE: 24
ctcatcacgc agctc        15

-continued

```
<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
ccggacatag tccaggaggc ag                                               22

<210> SEQ ID NO 26
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(23)
<223> OTHER INFORMATION: may be joined by phosphorothioate bonds

<400> SEQUENCE: 26
tgcctcacct ccaccgtgca gct                                              23

<210> SEQ ID NO 27
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(21)
<223> OTHER INFORMATION: may be joined by phosphorothioate bonds

<400> SEQUENCE: 27
cctcacctcc accgtgcagc t                                                21

<210> SEQ ID NO 28
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(20)
<223> OTHER INFORMATION: may be joined by phosphorothioate bonds

<400> SEQUENCE: 28
ctcacctcca ccgtgcagct                                                  20

<210> SEQ ID NO 29
<211> LENGTH: 31
<212> TYPE: DNA
<213> ORGANISM: Artificial Sequence
<220> FEATURE:
<223> OTHER INFORMATION: Switch blocker olignucleotide
<220> FEATURE:
<221> NAME/KEY: misc_feature
<222> LOCATION: (1)..(1)
<223> OTHER INFORMATION: may have a BHQ1 moiety attached
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (1)..(3)
<223> OTHER INFORMATION: may be joined by phosphorothioate bonds
<220> FEATURE:
```

```
<221> NAME/KEY: modified_base
<222> LOCATION: (1)..(1)
<223> OTHER INFORMATION: 2-OMe-guanosine
<220> FEATURE:
<221> NAME/KEY: modified_base
<222> LOCATION: (2)..(2)
<223> OTHER INFORMATION: 2'-OMe-adenosine
<220> FEATURE:
<221> NAME/KEY: modified_base
<222> LOCATION: (3)..(3)
<223> OTHER INFORMATION: 2'-OMe-uridine
<220> FEATURE:
<221> NAME/KEY: modified_base
<222> LOCATION: (11)..(14)
<223> OTHER INFORMATION: n is 5-nitroindole
<220> FEATURE:
<221> NAME/KEY: misc_feature
<222> LOCATION: (18)..(18)
<223> OTHER INFORMATION: may have a Fam moiety attached
<220> FEATURE:
<221> NAME/KEY: modified_base
<222> LOCATION: (29)..(29)
<223> OTHER INFORMATION: 2'-OMe-cytosine
<220> FEATURE:
<221> NAME/KEY: modified_base
<222> LOCATION: (30)..(30)
<223> OTHER INFORMATION: 2'-OMe-uridine
<220> FEATURE:
<221> NAME/KEY: modified_base
<222> LOCATION: (31)..(31)
<223> OTHER INFORMATION: 2'-OMe-cytosine
<220> FEATURE:
<221> NAME/KEY: misc_feature
<222> LOCATION: (29)..(31)
<223> OTHER INFORMATION: may be joined by phosphorothioate bonds
<220> FEATURE:
<221> NAME/KEY: misc_feature
<222> LOCATION: (31)..(31)
<223> OTHER INFORMATION: may have a three carbon spacer attached

<400> SEQUENCE: 29
gaucacgcag nnnntgccct tcggctgccu c                                  31

<210> SEQ ID NO 30
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(25)
<223> OTHER INFORMATION: may be joined by phosphorothioate bonds

<400> SEQUENCE: 30
ttgtgttccc ggacatagtc cagga                                         25

<210> SEQ ID NO 31
<211> LENGTH: 25
<212> TYPE: DNA
<213> ORGANISM: Artificial Sequence
<220> FEATURE:
<223> OTHER INFORMATION: region of the EGFR gene that have mutations
<220> FEATURE:
<221> NAME/KEY: misc_feature
<222> LOCATION: (23)..(23)
<223> OTHER INFORMATION: n is a, c, g, or t

<400> SEQUENCE: 31
tcaaattttg agttgcatcc ccngg                                         25

<210> SEQ ID NO 32
<211> LENGTH: 29
```

```
<212> TYPE: DNA
<213> ORGANISM: Artificial Sequence
<220> FEATURE:
<223> OTHER INFORMATION: region of the EGFR gene that have mutations

<400> SEQUENCE: 32
gcatgaactg cgtgatgagc tgcacggag                                           29

<210> SEQ ID NO 33
<211> LENGTH: 17
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (14)..(17)
<223> OTHER INFORMATION: may be joined by phosphorothioate bonds

<400> SEQUENCE: 33
gcacgcacac acatatc                                                        17

<210> SEQ ID NO 34
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: 2-OMe-uridine
<220> FEATURE:
<221> NAME/KEY: modified_base
<222> LOCATION: (2)..(2)
<223> OTHER INFORMATION: 2-OMe-cytosine
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (3)..(15)
<223> OTHER INFORMATION: Bases are 2'-fluoro ribonucleosides
<220> FEATURE:
<221> NAME/KEY: misc_feature
<222> LOCATION: (13)..(15)
<223> OTHER INFORMATION: may be joined by phosphorothioate bonds
<220> FEATURE:
<221> NAME/KEY: misc_feature
<222> LOCATION: (15)..(15)
<223> OTHER INFORMATION: may be labeled with an LC Red 640 moiety

<400> SEQUENCE: 34
ucaucacgca gcuca                                                          15

<210> SEQ ID NO 35
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: (1)..(1)
<223> OTHER INFORMATION: 2-OMe-uridine
<220> FEATURE:
<221> NAME/KEY: modified_base
<222> LOCATION: (2)..(2)
```

```
<223> OTHER INFORMATION: 2-OMe-cytosine
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (3)..(15)
<223> OTHER INFORMATION: Bases are 2'-fluoro ribonucleosides
<220> FEATURE:
<221> NAME/KEY: misc_feature
<222> LOCATION: (13)..(15)
<223> OTHER INFORMATION: may be joined by phosphorothioate bonds
<220> FEATURE:
<221> NAME/KEY: misc_feature
<222> LOCATION: (15)..(15)
<223> OTHER INFORMATION: may be labeled with an Alexa Fluor 546 moiety

<400> SEQUENCE: 35
ucaucacgca gcuca                                                    15

<210> SEQ ID NO 36
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (12)..(15)
<223> OTHER INFORMATION: may be joined by phosphorothioate bonds

<400> SEQUENCE: 36
cgtgcarctc atcat                                                    15

<210> SEQ ID NO 37
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: modified_base
<222> LOCATION: (1)..(5)
<223> OTHER INFORMATION: Bases are 2'-fluoro ribonucleosides
<220> FEATURE:
<221> NAME/KEY: misc_feature
<222> LOCATION: (5)..(6)
<223> OTHER INFORMATION: may be joined by a 7 carbon spacer and 6-Fam
     moiety
<220> FEATURE:
<221> NAME/KEY: modified_base
<222> LOCATION: (15)..(19)
<223> OTHER INFORMATION: Bases are 2'-fluoro ribonucleosides
<220> FEATURE:
<221> NAME/KEY: misc_feature
<222> LOCATION: (26)..(28)
<223> OTHER INFORMATION: may be joined by phosphorothioate bonds
<220> FEATURE:
<221> NAME/KEY: misc_feature
<222> LOCATION: (28)..(28)
<223> OTHER INFORMATION: may have a Dabcyl moiety attached

<400> SEQUENCE: 37
ugcccttcgg ctgccuccug gagccgaa                                      28
```

<210> SEQ ID NO 38
<211> LENGTH: 101
<212> TYPE: DNA
<213> ORGANISM: Artificial Sequence
<220> FEATURE:
<223> OTHER INFORMATION: wild-type synthetic target

<400> SEQUENCE: 38
gagcaggtac tgggagccaa tattgtcttt gtgttcccgg acatagtcca ggaggcagcc    60
gaagggcatg agctgcgtga tgagctgcac ggtggaggtg a                      101

<210> SEQ ID NO 39
<211> LENGTH: 101
<212> TYPE: DNA
<213> ORGANISM: Artificial Sequence
<220> FEATURE:
<223> OTHER INFORMATION: T790M mutant synthetic target

<400> SEQUENCE: 39
gagcaggtac tgggagccaa tattgtcttt gtgttcccgg acatagtcca ggaggcagcc    60
gaagggcatg agctgcatga tgagctgcac ggtggaggtg a                      101

<210> SEQ ID NO 40
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(21)
<223> OTHER INFORMATION: may be joined by phosphorothioate bonds

<400> SEQUENCE: 40
ctccaccgtg carctcatca t                                             21

<210> SEQ ID NO 41
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (35)..(38)
<223> OTHER INFORMATION: may be joined by phosphorothioate bonds

<400> SEQUENCE: 41
tgagcaggta ctgggagcca atattgtctt tgtgttcc                           38

<210> SEQ ID NO 42
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: may have a BHQ1 moiety attached
<220> FEATURE:
<221> NAME/KEY: misc_feature
<222> LOCATION: (1)..(3)
<223> OTHER INFORMATION: may be joined by phosphorothioate bonds

```
<220> FEATURE:
<221> NAME/KEY: modified_base
<222> LOCATION: (1)..(1)
<223> OTHER INFORMATION: 2-OMe-cytosine
<220> FEATURE:
<221> NAME/KEY: modified_base
<222> LOCATION: (2)..(2)
<223> OTHER INFORMATION: 2'-OMe-adenosine
<220> FEATURE:
<221> NAME/KEY: modified_base
<222> LOCATION: (3)..(3)
<223> OTHER INFORMATION: 2'-OMe-uridine
<220> FEATURE:
<221> NAME/KEY: modified_base
<222> LOCATION: (4)..(10)
<223> OTHER INFORMATION: Bases are 2'-fluoro ribonucleosides
<220> FEATURE:
<221> NAME/KEY: modified_base
<222> LOCATION: (11)..(14)
<223> OTHER INFORMATION: n is 5-nitroindole
<220> FEATURE:
<221> NAME/KEY: misc_feature
<222> LOCATION: (18)..(18)
<223> OTHER INFORMATION: may have a Fam moiety attached
<220> FEATURE:
<221> NAME/KEY: modified_base
<222> LOCATION: (44)..(44)
<223> OTHER INFORMATION: 2'-OMe-cytosine
<220> FEATURE:
<221> NAME/KEY: modified_base
<222> LOCATION: (45)..(45)
<223> OTHER INFORMATION: 2'-OMe-guanosine
<220> FEATURE:
<221> NAME/KEY: modified_base
<222> LOCATION: (46)..(46)
<223> OTHER INFORMATION: 2'-OMe-guanosine
<220> FEATURE:
<221> NAME/KEY: misc_feature
<222> LOCATION: (44)..(46)
<223> OTHER INFORMATION: may be joined by phosphorothioate bonds
<220> FEATURE:
<221> NAME/KEY: misc_feature
<222> LOCATION: (46)..(46)
<223> OTHER INFORMATION: may have a three carbon spacer attached
<220> FEATURE:
<221> NAME/KEY: misc_feature
<222> LOCATION: (11)..(14)
<223> OTHER INFORMATION: n is a, c, g, t or u

<400> SEQUENCE: 42
caucacgcag nnnntgccct tcggctgcct cctggactat gtccgg         46

<210> SEQ ID NO 43
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (15)..(18)
<223> OTHER INFORMATION: may be joined by phosphorothioate bonds

<400> SEQUENCE: 43
cacctccacc gtgcarct         18

<210> SEQ ID NO 44
<211> LENGTH: 56
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (53)..(56)
<223> OTHER INFORMATION: may be joined by phosphorothioate bonds

<400> SEQUENCE: 44
ccatctcatc cctgcgtgtc tccgactcag ctaaggtaac gatcaccgtg carctc         56

<210> SEQ ID NO 45
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (39)..(42)
<223> OTHER INFORMATION: may be joined by phosphorothioate bonds

<400> SEQUENCE: 45
cctctctatg ggcagtcggt gattgttccc ggacatagtc ca                       42

<210> SEQ ID NO 46
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: may have a Cy3 moiety attached
<220> FEATURE:
<221> NAME/KEY: misc_feature
<222> LOCATION: (1)..(2)
<223> OTHER INFORMATION: may be joined by phosphorothioate bonds
<220> FEATURE:
<221> NAME/KEY: misc_feature
<222> LOCATION: (35)..(38)
<223> OTHER INFORMATION: may be joined by phosphorothioate bonds

<400> SEQUENCE: 46
tgagcaggta ctgggagcca atattgtctt tgtgttcc                            38

<210> SEQ ID NO 47
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(3)
<223> OTHER INFORMATION: may be joined by phosphorothioate bonds
<220> FEATURE:
<221> NAME/KEY: misc_feature
<222> LOCATION: (18)..(21)
<223> OTHER INFORMATION: may be joined by phosphorothioate bonds

<400> SEQUENCE: 47
gtgatggcca gcgtggacaa c                                              21
```